US012708886B2

(12) United States Patent
Abate et al.

(10) Patent No.: US 12,708,886 B2
(45) Date of Patent: Aug. 18, 2026

(54) METHOD OF GENERATING MONODISPERSE EMULSIONS

(71) Applicant: The Regents of the University of California, Oakland, CA (US)

(72) Inventors: Adam R. Abate, Daly City, CA (US); Makiko N. Hatori, Oakland, CA (US); Leqian Liu, Oakland, CA (US); Samuel Kim, Palo Alto, CA (US); Cyrus Modavi, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/649,068

(22) PCT Filed: Sep. 28, 2018

(86) PCT No.: PCT/US2018/053598
§ 371 (c)(1),
(2) Date: Mar. 19, 2020

(87) PCT Pub. No.: WO2019/139650
PCT Pub. Date: Jul. 18, 2019

(65) Prior Publication Data

US 2020/0261879 A1 Aug. 20, 2020

Related U.S. Application Data

(60) Provisional application No. 62/565,976, filed on Sep. 29, 2017.

(51) Int. Cl.

*C12Q 1/68* (2018.01)
*B01J 13/08* (2006.01)
*C09K 23/42* (2022.01)
*C12Q 1/6844* (2018.01)
*C12Q 1/6869* (2018.01)
*C09K 23/00* (2022.01)

(52) U.S. Cl.

CPC ............... *B01J 13/08* (2013.01); *C09K 23/42* (2022.01); *C12Q 1/6844* (2013.01); *C12Q 1/6869* (2013.01); *C09K 23/00* (2022.01)

(58) Field of Classification Search

None
See application file for complete search history.

(56) References Cited

U.S. PATENT DOCUMENTS 7,638,276 B2 12/2009 Griffiths et al.
RE41,780 E 9/2010 Anderson et al.
8,067,159 B2 11/2011 Brown et al.
8,257,925 B2 9/2012 Brown et al.
8,765,485 B2 7/2014 Link et al.
8,790,876 B2 7/2014 Leamon et al.
9,150,852 B2 10/2015 Samuels et al.
10,161,007 B2 12/2018 Abate et al.
10,745,762 B2 8/2020 Abate et al.
11,142,791 B2 10/2021 Abate
2002/0086042 A1 7/2002 Delrieu et al.
2003/0156993 A1 8/2003 Staats
2003/0180737 A1 9/2003 Gu et al.
2005/0019902 A1 1/2005 Mathies et al.
2005/0112639 A1 5/2005 Wang et al.
2005/0172476 A1 8/2005 Stone et al.
2007/0039866 A1 2/2007 Schroeder et al.
2007/0077572 A1 4/2007 Tawfik et al.
2007/0141593 A1 6/2007 Lee et al.
2007/0231880 A1 10/2007 Chang-yen et al.
2008/0014589 A1 1/2008 Link et al.
2009/0045064 A1 2/2009 Simmons et al.
2009/0098555 A1 4/2009 Roth et al.
2010/0015614 A1 1/2010 Beer et al.
2010/0028915 A1 2/2010 Gualberto et al.
2010/0055677 A1 3/2010 Colston, Jr. et al.
2010/0137163 A1 6/2010 Link et al.
2010/0173394 A1 7/2010 Colston, Jr. et al.
2010/0285975 A1 11/2010 Mathies et al.
2011/0053798 A1 3/2011 Hindson et al.

(Continued)

FOREIGN PATENT DOCUMENTS

AU 2013203624 A1 5/2013
AU 2013302867 A1 2/2015

(Continued)

OTHER PUBLICATIONS

Tamminen et al. Single gene-based distiction of individual microbial genomes from a mixed population of microbial cells. Frontiers in Microbiology, vol. 6, Article 195, p. 1-10, 2015.*
Spencer, SJ., et al. Massively parallele sequencing of single cells by epicPCR links functional genes with phylogenetic markers. The ISME Journal, vol. 10, p. 427-436, (2016).*
Extended European Search Report received for European Patent Application Serial No. 17840230.1 dated Apr. 30, 2020, 12 pages.
Extended European Search Report received for European Patent Application Serial No. 17885180.4 dated Jul. 20, 2020, 11 pages.
Extended European Search Report received for European Patent Application Serial No. 13829925.0 dated Feb. 8, 2016, 7 pages.

(Continued)

*Primary Examiner* — Suryaprabha Chunduru
(74) *Attorney, Agent, or Firm* — Edward J. Baba; Michael J. Blessent; Bozicevic, Field & Francis LLP

(57) ABSTRACT

The methods described herein, referred to as particle-templated emulsification (PTE), provide an improved approach for generating a monodisperse emulsion that encapsulates target particles of interest without requiring the use of a microfluidic device. Monodisperse droplets may be effectively obtained by using monodisperse particles to template the formation of droplets, which can include, e.g., monodisperse single-emulsion droplets, multiple-emulsion droplets, or Giant Unilamellar Vesicles (GUV), without destroying the integrity of the droplets.

16 Claims, 20 Drawing Sheets

Specification includes a Sequence Listing.

(56) References Cited

U.S. PATENT DOCUMENTS

2011/0056575 A1 3/2011 Hong et al.
2011/0059556 A1 3/2011 Strey et al.
2011/0086352 A1 4/2011 Bashir et al.
2011/0103176 A1 5/2011 Van Dam et al.
2011/0104816 A1 5/2011 Pollack et al.
2011/0118151 A1 5/2011 Eshoo et al.
2011/0160078 A1 6/2011 Fodor et al.
2011/0201526 A1* 8/2011 Berka .................. C12Q 1/6867 506/26
2011/0217736 A1 9/2011 Hindson
2011/0311978 A1 12/2011 Makarewicz, Jr. et al.
2012/0010086 A1 1/2012 Froehlich et al.
2012/0045765 A1 2/2012 Curran et al.
2012/0122714 A1 5/2012 Samuels et al.
2012/0132288 A1 5/2012 Weitz et al.
2012/0190032 A1 7/2012 Ness et al.
2012/0190033 A1 7/2012 Ness et al.
2012/0196288 A1 8/2012 Beer
2012/0219947 A1 8/2012 Yurkovetsky et al.
2012/0220494 A1 8/2012 Samuels et al.
2012/0222748 A1* 9/2012 Weitz .................... B01F 3/0807 137/1
2012/0258870 A1 10/2012 Schwartz et al.
2012/0264646 A1 10/2012 Link et al.
2012/0270739 A1 10/2012 Rava et al.
2012/0309002 A1 12/2012 Link
2012/0316074 A1 12/2012 Saxonov
2013/0032235 A1 2/2013 Johnstone et al.
2013/0046030 A1 2/2013 Rotem et al.
2013/0084572 A1 4/2013 Hindson et al.
2013/0095469 A1 4/2013 Koltay et al.
2013/0116130 A1 5/2013 Fu et al.
2013/0130919 A1 5/2013 Chen et al.
2013/0189700 A1 7/2013 So et al.
2013/0203605 A1 8/2013 Shendure et al.
2013/0210639 A1 8/2013 Link et al.
2013/0236901 A1 9/2013 Potier et al.
2013/0295567 A1 11/2013 Link et al.
2013/0295587 A1 11/2013 Sjobom
2014/0045712 A1 2/2014 Link et al.
2014/0057799 A1 2/2014 Johnson et al.
2014/0154695 A1 6/2014 Miller et al.
2014/0155295 A1 6/2014 Hindson et al.
2014/0179544 A1 6/2014 Steenblock et al.
2014/0194300 A1 7/2014 Song et al.
2014/0199730 A1* 7/2014 Agresti .................. C12Q 1/686 435/91.2
2014/0199731 A1 7/2014 Agresti et al.
2014/0200146 A1 7/2014 Xie et al.
2014/0272988 A1 9/2014 Zador et al.
2014/0323316 A1 10/2014 Drmanac et al.
2014/0378345 A1 12/2014 Hindson et al.
2014/0378349 A1 12/2014 Hindson et al.
2015/0225786 A1* 8/2015 Litterst ................ C12Q 1/6809 506/2
2015/0232942 A1 8/2015 Abate et al.
2015/0267261 A1 9/2015 Byrd et al.
2015/0298091 A1 10/2015 Weitz et al.
2016/0064755 A1 3/2016 Hubner et al.
2016/0177375 A1 6/2016 Abate et al.
2016/0265043 A1 9/2016 Geng et al.
2017/0009274 A1 1/2017 Abate et al.
2017/0022538 A1 1/2017 Abate et al.
2017/0121756 A1 5/2017 Abate et al.
2018/0056288 A1 3/2018 Abate et al.
2018/0216160 A1 8/2018 Abate et al.
2018/0237836 A1 8/2018 Abate et al.
2019/0127789 A1 5/2019 Weitz et al.
2019/0169700 A1 6/2019 Abate et al.
2019/0218594 A1 7/2019 Abate et al.
2019/0241965 A1 8/2019 Abate et al.
2019/0330701 A1 10/2019 Abate et al.

FOREIGN PATENT DOCUMENTS

AU 2016215298 A1 8/2017
AU 2016215304 A1 8/2017
AU 2017382905 A1 7/2019
AU 2019226236 A1 9/2019
CA 2881783 A1 2/2014
CA 3001986 A1 4/2016
CA 2974299 A1 8/2016
CA 2974306 A1 8/2016
CA 3047328 A1 6/2018
CN 1693478 A 11/2005
CN 104736725 A 6/2015
CN 107107058 A 8/2017
CN 107429426 A 12/2017
CN 107530654 A 1/2018
CN 108350488 A1 7/2018
CN 110088290 A1 8/2019
CN 110462053 A 11/2019
DE 10339452 A1 3/2005
EP 1547677 A1 6/2005
EP 2145955 B1 2/2012
EP 2565650 A1 3/2013
EP 2882872 A2 6/2015
EP 3160654 A2 5/2017
EP 3209419 A1 8/2017
EP 3253479 A2 12/2017
EP 3253910 A1 12/2017
EP 3337907 A1 6/2018
EP 3497228 A1 6/2019
EP 3571308 A1 11/2019
GB 2519906 A 5/2015
GB 2539836 A 12/2016
JP 2013503630 A 2/2013
JP 2014521334 A 8/2014
JP 2015533079 A 11/2015
JP 2016517281 A 6/2016
JP 2016163576 A 9/2016
JP 2017515469 A 6/2017
JP 2018505671 A 3/2018
JP 2018508198 A 3/2018
JP 2018525004 A 9/2018
WO WO1994012216 A1 6/1994
WO WO2007140015 A2 6/1994
WO WO2009050512 A2 4/2009
WO WO2009054870 A2 4/2009
WO WO2009111014 A2 9/2009
WO 2009148598 A1 12/2009
WO WO2010148039 A2 12/2010
WO WO2011047307 A1 4/2011
WO WO2012011091 A2 1/2012
WO WO2012048341 A1 4/2012
WO WO2012083225 A2 6/2012
WO WO2012109600 A2 8/2012
WO WO2012142213 A2 10/2012
WO WO2012162267 A2 11/2012
WO WO2013015793 A1 1/2013
WO WO2013095469 A1 6/2013
WO WO2013119753 A1 8/2013
WO WO2013126741 A1 8/2013
WO WO2013130512 A2 9/2013
WO WO2013134261 A1 9/2013
WO WO2013173394 A2 11/2013
WO 2014022210 A2 2/2014
WO WO2014028378 A2 2/2014
WO WO2014028537 A1 2/2014
WO WO2014047556 A1 3/2014
WO WO2014083435 A2 6/2014
WO WO2014093676 A1 6/2014
WO WO2014108323 A1 7/2014
WO 2014145555 A1 9/2014
WO WO2014138132 A2 9/2014
WO WO2014151658 A1 9/2014
WO WO2014153071 A1 9/2014
WO WO2015031691 A1 3/2015
WO WO2015069798 A1 5/2015
WO WO2015120398 A1 8/2015
WO 2015164212 A1 10/2015
WO WO2015157369 A1 10/2015

(56) References Cited

FOREIGN PATENT DOCUMENTS

| | | | |
|---|---|---|---|
| WO | 2015179848 | A1 | 11/2015 |
| WO | WO2015189336 | A1 | 12/2015 |
| WO | WO2015200717 | A2 | 12/2015 |
| WO | WO2016064755 | A2 | 4/2016 |
| WO | WO2016065056 | A1 | 4/2016 |
| WO | WO2016126865 | A1 | 8/2016 |
| WO | WO2016126871 | A2 | 8/2016 |
| WO | WO2017031125 | A1 | 2/2017 |
| WO | 2017075072 | A1 | 5/2017 |
| WO | WO2018031691 | A1 | 2/2018 |
| WO | WO2018119301 | A1 | 6/2018 |
| WO | 2019099908 | A1 | 5/2019 |

OTHER PUBLICATIONS

Extended European Search Report received for European Patent Application Serial No. 16837703.4 dated Nov. 29, 2018, 9 pages.
Extended European Search Report received for European Patent Application Serial No. 15853268.9 dated Sep. 3, 2018, 12 pages.
Extended European Search Report received for European Patent Application Serial No. 16747229.9 dated Sep. 10, 2019, 8 pages.
Extended European Search Report received for European Patent Application Serial No. 16747224.0 dated May 24, 2018, 9 pages.
Extended European Search Report received for European Patent Application Serial No. 15812857.9 dated Oct. 17, 2017, 7 pages.
First search received for Chinese Patent Application Serial No. 2013800532581 dated Feb. 22, 2016, 2 pages.
First search received for Chinese Patent Application Serial No. 2015800704110 dated Dec. 13, 2018, 2 pages.
International Preliminary Report on Patentability received for PCT Application Serial No. PCT/US2015/056743 dated May 4, 2017, 9 pages.
International Preliminary Report on Patentability received for PCT Application Serial No. PCT/US2015/037822 dated Jan. 5, 2017, 7 pages.
International Preliminary Report on Patentability received for PCT Application Serial No. PCT/US2013/054517 dated Feb. 26, 2015, 14 pages.
International Preliminary Report on Patentability received for PCT Application Serial No. PCT/US2016/047199 dated Mar. 1, 2018, 8 pages.
International Preliminary Report on Patentability received for PCT Application Serial No. PCT/US2017/046159 dated Feb. 21, 2019, 9 pages.
International Preliminary Report on Patentability received for PCT Application Serial No. PCT/US2016/016444 dated Aug. 17, 2017, 40 pages.
International Preliminary Report on Patentability received for PCT Application Serial No. PCT/US2016/016438 dated Aug. 17, 2017, 10 pages.
International Preliminary Report on Patentability received for PCT Application Serial No. PCT/US2017/068006 dated Jul. 4, 2019, 7 pages.
International Search Report and Written Opinion received for PCT Application Serial No. PCT/US2013/054517 dated Feb. 21, 2014, 19 pages.
International Search Report and Written Opinion received for PCT Application Serial No. PCT/US2015/056743 dated Mar. 3, 2016, 12 pages.
International Search Report and Written Opinion received for PCT Application Serial No. PCT/US2015/037822 dated Feb. 2, 2016, 9 pages.
International Search Report and Written Opinion received for PCT Application Serial No. PCT/US2016/047199 dated Dec. 12, 2016, 10 pages.
International Search Report and Written Opinion received for PCT Application Serial No. PCT/US2017/046159 dated Nov. 21, 2017, 12 pages.
International Search Report and Written Opinion received for PCT Application Serial No. PCT/US2016/016444 dated Jul. 27, 2016, 43 pages.
International Search Report and Written Opinion received for PCT Application Serial No. PCT/US2016/016438 dated Jun. 10, 2016, 14 pages.
International Search Report and Written Opinion received for PCT Application Serial No. PCT/US2017/068006 dated Mar. 26, 2018, 9 pages.
Integrated DNA Technologies "Molecular Facts and Figures", 2011, pp. 1-9.
Abate, Adam R., et al., (2011) "Efficient encapsulation with plug-triggered drop formation", Phys Rev E Stat Nonlin Soft Matter Phys., vol. 84(3), p. 03150209.
Abate, Adam R., et al., (2010) "Microfluidic sorting with high-speed single-layer membrane valves", Applied Physics Letters 96, pp. 203509-1-203509-3.
Abate, Adam R., et al., (2010) "One-step formation of multiple emulsions in microfluidics", Lab on a Chip, vol. 11(2), pp. 253-258.
Abate, Adam R., et al., (2008) "Photoreactive coating for high-contrast spatial patterning of microfluidic device wettability", Lab on a Chip, vol. 8(12), pp. 2157-2160.
Agresti, Jeremy J., et al., (2010) "Ultrahigh-throughput screening in drop-based microfluidics for directed evolution" Corrected Version—Proc Natl Acad Sci USA, 107(14), pp. 6550-6551.
Ali, M Monsur., et al., (2014) "Rolling circle amplification: a versatile tool for chemical biology, materials science and medicine", Chem Soc Rev., vol. 43(10), pp. 3324-3341.
Allen, Lisa Z., et al., (2011) "Single virus genomics: a new tool for virus discovery", PLoS ONE vol. 6(3), p. e17722.
Arriaga, Laura R., et al., (2014) "Ultrathin Shell Double Emulsion Templated Giant Unilamellar Lipid Vesicles with Controlled", Microdomain Formation, vol. 10(5), pp. 950-956.
Atten, P, (1993) "Electro coalescence of Water Droplets in an Insulating Liquid" vol. 30, pp. 259-269.
Barenholz, Y, et al., (1993) "A simple method for the preparation of homogeneous phospholipid vesicles", Biochemistry 16(12), pp. 2806-2810.
Baret, Jean C., et al., (2009) Fluorescence-activated droplet sorting (FADS): efficient microfluidic cell sorting based on enzymatic activity, Lab on a Chip, vol. 9(13), pp. 1850-1858.
Battaglia, Giuseppe, et al., (2006) "Polymeric vesicle permeability: a facile chemical assay", Langmuir, vol. 22(11), pp. 4910-4913.
Beer, NR, et al., (2008) "On-chip single-copy real-time reverse-transcription PCR in isolated picoliter droplets", Anal Chem., vol. 80(6), pp. 1854-1858.
Bernath, K, et al., (2004) "In vitro compartmentalization by double emulsions: sorting and gene enrichment by fluorescence activated cell sorting", Analytical Biochemistry, vol. 325(1), pp. 151-157.
Bird, R E., et al., (1988) "Single-chain antigen-binding proteins", Science, vol. 242 (4877), pp. 423-426.
Blainey, Paul C., (2013) "The future is now: single-cell genomics of bacteria and archaea", FEMS microbiology reviews 37(3), pp. 407-427.
Brown, Robert B., et al., (2008) "Current techniques for single-cell lysis", J R Soc Interface, 5 Suppl 2, pp. S131-S138.
Caron, G. Nebe-von., et al., (1997) "Assessment of bacterial viability status by flow cytometry and single cell sorting", Journal of Applied Microbiology, vol. 84(6), pp. 988-998.
Caruccio, et al., (2011) "Preparation of next-generation sequencing libraries using Nextera™ technology: simultaneous DNA fragmentation and adaptor tagging by in vitro transposition", Methods in Molecular Biology, 2011, vol. 733, pp. 241-255.
Chabert, M, et al., (2005) "Droplet fusion by alternating current (AC) field electrocoalescence in microchannels", Electrophoresis, vol. 26(19), pp. 3706-3715.
Chaffer, Christine L., et al., (2011) "A Perspective on Cancer Cell Metastasis", Science, vol. 331(6024), pp. 1559-1564.
Chen, Chin-Ming, et al., (2000) "Influence of pH on the stability of oil-in-water emulsions stabilized by a splittable surfactant", Colloids and Surfaces A: Physicochemical and Engineering Aspects, vol. 170 (2-3), pp. 173-179.

(56) References Cited

OTHER PUBLICATIONS

Chung, Changkwon, et al., (2010) "Droplet dynamics passing through obstructions in confined microchannel flow", Microfluidics and Nanofluidics, vol. 9(6), pp. 1151-1163.
Clausell-Tormos, J., et al., (2008) "Droplet-based microfluidic platforms for the encapsulation and screening of Mammalian cells and multicellular organisms", Chemistry and Biology, vol. 15(5), pp. 427-437.
Demaree, Benjamin, et al., (2018), "An Ultrahigh-throughput Microfluidic Platform for Single-cell Genome Sequencing", Journal of Visualized Experiments 135 (e57598), pp. 1-13.
Dietrich, G J., et al., (2005) "Effects of UV irradiation and hydrogen peroxide on DNA fragmentation, motility and fertilizing ability of rainbow trout (*Oncorhynchus mykiss*) spermatozoa", Theriogenology, vol. 64(8), pp. 1809-1822.
Duffy, David C., et al., (1998) "Rapid Prototyping of Microfluidic Systems in Poly(dimethylsiloxane)", Anal. Chem., vol. 70(23), pp. 4974-4984.
Eastburn, Dennis J., et al., (2013) "Picoinjection enables digital detection of RNA with droplet rt-PCR" PLoS One, vol. 8(4), p. e62961.
Eastburn, Dennis J., et al., (2013) "Ultrahigh-Throughput Mammalian Single-Cell Reverse-Transcriptase Polymerase Chain Reaction in Microfluidic Drops", Anal. Chem. 85(16), pp. 8016-8021.
Edd, Jon F., et al., (2008) Controlled encapsulation of single-cells into monodisperse picolitre drops Lab Chip, vol. 8(8), pp. 1262-1264.
Frenz, Lucas, et al., (2009) "Reliable microfluidic on-chip incubation of droplets in delay-lines", Lab on a Chip, vol. 9(10), pp. 1344-1348.
Garstecki, Piotr, et al., (2006) "Formation of droplets and bubbles in a microfluidic T-junction-scaling and mechanism of break-up", Lab on a Chip, vol. 6(3), pp. 437-446.
Gevensleben, Heidrun, et al., (2013) "Non-invasive Detection of HER2 Amplification with Plasma DNA Digital PCR" Clinical Cancer Research, vol. 19(12), pp. 3276-3284.
Gong, Jian, et al., (2006) "Characterization and Design of Digitizing Processes for Uniform and Controllable Droplet Volume in EWOD Digital Microfluidics", Solid-State Sensors, Actuators, and Microsystems Workshop, pp. 159-162.
Gribskov, M, et al., (1986) "Sigma factors from *E. coli,* B. subtilis, phage SP01, and phage T4 are homologous proteins" Nucleic Acids Res., vol. 14(16), pp. 6745-6763.
Grover, Alka, et al., (2009) "Multiple displacement amplification as a pre-polymerase chain reaction (pre-PCR) to detect ultra low population of Ralstonia solanacearum (Smith 1896) Yabuchi et al. (1996)", Letters in Applied Microbiology, vol. 49(5), pp. 539-543.
Hayward, Ryan C., et al., (2006) "Dewetting instability during the formation of polymersomes from block-copolymer-stabilized double emulsions", Langmuir, vol. 22(10), pp. 4457-4461.
Herminghaus, S., (1999) "Dynamical Instability of Thin Liquid Films Between Conducting Media", Physical Review Letter, vol. 83(12), pp. 2359-2361.
Horton, Robert M., et al., (2013) "Gene splicing by overlap extension: tailor-made genes using the polymerase chain reaction" Biotechniques, vol. 54, pp. 129-133.
Hu, Hoa, et al., (2009) "Mutation screening in 86 known X-linked mental retardation genes by droplet-based multiplex PCR and massive parallel sequencing", Hugo J., vol. 3 (1-4), pp. 41-49.
Huebner, Ansgar, et al., (2008) "Microdroplets: A sea of applications? ", Lab on a Chip, vol. 8(8), pp. 1244-1254.
Hunkapiller, Tim, et al., (1986) "Immunology: The growing immunoglobulin gene superfamily", Nature, vol. 323, pp. 15-16.
Hunt, Josephine A., et al., (1994) "Effect of pH on the stability and surface composition of emulsions made with whey protein isolate" Journal of Agricultural and Food Chemistry, vol. 42(10), pp. 2131-2135.
Huston, J S., et al., (1988) "Protein engineering of antibody binding sites: recovery of specific activity in an anti-digoxin single-chain Fv analogue produced in *Escherichia coli*", Proc. Natl. Acad. Sci. U.S.A., vol. 85(16), pp. 5879-5883.
Ichii, Tetsuo, et al., (2010) "Amplification of RNA in Growing and Dividing Micro-Droplets", 14th International Conf on Miniaturized Systems for Chemistry and Life Sciences, pp. 2089-2091.
Kawasaki, Ernest S., (1990) "Sample Preparation From Blood, Cells, and Other Fluids", Chapter 18 of PCR Protocols: A guide to methods and Applications, pp. 146-152.
Ki, Jang-Seu, et al., (2004) "Integrated Method for Single-Cell DNA Extraction, PCR Amplification, and Sequencing of Ribosomal DNA from Harmful Dinoflagellates Cochlodinium polykrikoides and Alexandrium catenella", Marine Biotechnology, vol. 6, pp. 587-593.
Kiss, Margaret M., et al., (2008) "High-Throughput Quantitative Polymerase Chain Reaction in Picoliter Droplets", Anal Chem, vol. 80(23), pp. 8975-8981.
Kritikou, Ekat, (2005) "It's cheaper in the Picolab", Nat Rev Genet, vol. 6, p. 668.
Küster, Simon K., et al., (2013) "Interfacing Droplet Microfluidics with Matrix-Assisted Laser Desorption/Ionization Mass Spectrometry: Label-Free Content Analysis of Single Droplets", Anal Chem, vol. 85(3), pp. 1285-1289.
Lagally, E T., et al., (2001) "Single-Molecule DNA Amplification and Analysis in an Integrated Microfluidic Device", Analytical Chemistry, vol. 73(3), pp. 565-570.
Lage, J. M.., et al., (2003) "Whole Genome Analysis of Genetic Alterations in Small DNA Samples Using Hyperbranched Strand Displacement Amplification and Array-CGH", Genome Res., 13, pp. 294-307.
Lan, Freeman, et al., (2017) "Single-cell genome sequencing at ultra-high-throughput with microfluidic droplet barcoding", Nature Biotechnology, vol. 35(7), pp. 640-646.
Lanzavecchia, Antonio, et al., (1987) "The use of hybrid hybridomas to target human cytotoxic T lymphocytes", Eur. J. Immunology, vol. 17(1), pp. 105-111.
Le Goff, et al., (2015) "Hydrogel microparticles for biosensing", Eur Polym J., vol. 72, pp. 386-412.
Leary, James F., (1994) "Strategies for rare cell detection and isolation", Methods Cell Biol., vol. 42, pp. 331-358.
Lim, Shaun W., et al., (2013) "Ultrahigh-throughput sorting of microfluidic drops with flow cytometry", Lab on a Chip, vol. 13, pp. 4563-4572.
Link, D R., et al., (2004) "Geometrically mediated breakup of drops in microfluidic devices", Phys. Rev. Lett., vol. 92(5), p. 054503.
Livak, K J., et al., (2001) "Analysis of Relative Gene Expression Data Using Real-Time Quantitative PCR and the 2(-Delta Delta C(T)) Method", Methods, vol. 25(4), pp. 402-408.
Longo, M C., et al., (1990) "Use of uracil DNA glycosylase to control carry-over contamination in polymerase chain reactions" Gene, vol. 93(1), pp. 125-128.
Malloggi, Florent, et al., (2007) "Electrowetting-controlled droplet generation in a microfluidic flow-focusing device", Journal of Physics Condensed Matter, vol. 19(46), 462101, pp. 1-7.
Marcus, Joshua S., et al., (2006) "Parallel Picoliter rt-PCR Assays Using Microfluidics", Analytical Chemistry, vol. 78(3), pp. 956-958.
Markou, Athina, et al., (2011) "Molecular Characterization of Circulating Tumor Cells in Breast Cancer by a Liquid Bead Array Hybridization Assay", Clinical Chemistry, vol. 57(3), pp. 421-430.
Mary, Pascaline, et al., (2011) "Controlling droplet incubation using close-packed plug flow", Biomicrofluidics, vol. 5(2), p. 24101.
McDonald, J C., et al., (2000) "Fabrication of microfluidic systems in poly(dimethylsiloxane)", Electrophoresis, vol. 21(1), pp. 27-40.
Medkova, Martina, et al., (2010) "Analyzing Cancer at Single Cell Resolution with Droplet Technology", American Association of Cancer Research (AACR), 1 page.
Metzker, Michael L., (2010) "Sequencing technologies—the next generation", Nature Reviews Genetics, vol. 11, pp. 31-46.
Miyazaki, Kentaro, (2002) "Random DNA fragmentation with endonuclease V: application to DNA shuffling", vol. 30(24), e139, 3 pages.

(56) References Cited

OTHER PUBLICATIONS

Miyazaki, Ryo, et al., (2013) "A new large-DNA-fragment delivery system based on integrase activity from an integrative and conjugative element", Appl Environ Microbiol, vol. 79(14), pp. 4440-4447.
Moon, Sangjun, et al., (2011) "Drop-on-Demand Single Cell Isolation and Total RNA Analysis", vol. 6, Issue 3, pp. 1-10.
Morton, Keith J., et al., (2008) "Crossing microfluidic streamlines to lyse, label and wash cells", Lab Chip vol. 8(9), pp. 1448-1453.
Mui, B. L., et al., (1993) "Osmotic properties of large unilamellar vesicles prepared by extrusion", vol. 64(2), pp. 443-453.
Nagrath, Sunitha, et al., (2007) "Isolation of rare circulating tumour cells in cancer patients by microchip technology", Nature, vol. 450, pp. 1235-1239.
Nakano, Michihiko, et al., (2005) "Single-molecule reverse transcription polymerase chain reaction using water-in-oil emulsion", Journal of Bioscience and Bioengineering, vol. 99(3), pp. 293-295.
Nikolova, Albena N., et al., (1996) "Effect of grafted PEG-2000 on the size and permeability of vesicles", vol. 1304(2), pp. 120-128.
Nunes, J K., et al., (2013) "Dripping and jetting in microfluidic multiphase flows applied to particle and fibre synthesis" Journal of Physics D: Applied Physics, vol. 46(11), pp. 1-39.
O'Donovan, Brian, et al., (2012) "Electrode-free picoinjection of microfluidic drops", Lab on a chip, vol. 12, pp. 4029-4032.
Oberholzer, Thomas, et al., (1995) "Polymerase chain reaction in liposomes", vol. 2(10), pp. 677-682.
Okochi, Mina, et al., (2010) "Droplet-based gene expression analysis using a device with magnetic force-based-droplet-handling system", Journal of Bioscience and Bioengineering, vol. 109(2), pp. 193-197.
Pekin, Deniz, et al., (2011) "Quantitative and sensitive detection of rare mutations using droplet-based microfluidics", Lab Chip 11, pp. 2156-2166.
Perry, David J., (1999) "Solid-Phase Sequencing of Biotinylated PCR Products with Streptavidin-Coated Magnetic Beads" Hemostasis and Thrombosis Protocols, vol. 31, pp. 49-54.
Piatek, Amy S., et al., (1998) "Molecular beacon sequence analysis for detecting drug resistance in *Mycobacterium tuberculosis*", Nature Biotechnology, vol. 16(4), pp. 359-363.
Priest, Craig, et al., (2006) "Controlled electrocoalescence in microfluidics: Targeting a single lamella" Appl Phys Lett, vol. 89, pp. 134101-1-134101-3.
Rakszewska, Agata, et al., (2014) "One drop at a time: toward droplet microfluidics as a versatile tool for single-cell analysis", NPG Asia Materials 6(10), pp. 1-11.
Roche, (2011) "emPCR Amplification Method Manual—Lib L LV", GS FLX+ Series—XL+, 454 Sequencing, Life Science Corp., pp. 1-12.
Rolando, Monica, et al., (2013) "Legionella pneumophila Effector RomA Uniquely Modifies Host Chromatin to Repress Gene Expression and Promote Intracellular Bacterial Replication", Cell Host & Microbe, vol. 13(4), pp. 395-405.
Sciambi, Adam, et al., (2013) "Adding reagent to droplets with controlled rupture of encapsulated double emulsions", Biomicrofluidics, vol. 7(4), pp. 044112-1-044112-6.
Sciambia, Adam, et al., (2015) "Accurate microfluidic sorting of droplets at 30 kHz", Lab Chip vol. 15(1), pp. 47-51.
Seemann, Ralf, et al., (2011) "Droplet based microfluidics", IOP Science, vol. 75, 016601, pp. 1-41.
Shui, Lingling, et al., (2011) "Microfluidic DNA fragmentation for on-chip genomic analysis", Nanotechnology, vol. 22(49), 494013, pp. 1-7.
Siegel, Adam, et al., (2007), "Microsolidics: Fabrication of Three-Dimensional Metallic Microstructures in Poly (dimethylsiloxane)" Advanced Materials, vol. 19(5), pp. 727-733.
Song, Helen, et al., (2006) "Reactions in droplets in microfluidic channels", Angew Chem Int Ed Engl, vol. 45(44), pp. 7336-7356.
Squires, Tom M., et al., (2005) "Microfluidics: Fluid physics at the nanoliter scale", Reviews of modern physics, vol. 77(3), pp. 977-1026.
Stone, H. A., et al., (2004) "Engineering flows in small devices: microfluidics toward a lab-on-a-chip", vol. 36, pp. 381-411.
Stott, Shannon L., et al., (2010) "Isolation of circulating tumor cells using a microvortex-generating herringbone-chip", Proc Natl Acad Sci USA, vol. 107(43), pp. 18392-18397.
Syed, F, et al., (2009) "Next-generation sequencing library preparation: simultaneous fragmentation and tagging using in vitro transposition", vol. 6, pp. 1-2.
Tadmorad, Arbel D., et al., (2011) "Probing individual environmental bacteria for viruses by using microfluidic digital PCR" vol. 333(6038), pp. 58-62.
Takagi, Junya, et al., (2005) "Continuous particle separation in a microchannel having asyuuuetrically arranged multiple branches", Lab on a Chip, vol. 5(7), pp. 778-784.
Teh, Shia-Yen, et al., (2008) "Droplet microfluidics", Lab on a chip, vol. 8, Issue 2, pp. 198-220.
Tewhey, Ryan, et al., (2009) "Microdroplet-based PCR enrichment for large-scale targeted sequencing" Nature Biotechnology, vol. 27, pp. 1025-1031.
Thomann, Yi, et al., (2005) "PMMA Gradient Materials and in situ Nanocoating via Self-Assembly of Semifluorinated Hyperbranched Amphiphiles", Macromolecular Chemistry and Physics, vol. 206(1), pp. 135-141.
Thorsen, Todd, et al., (2001) "Dynamic pattern formation in a vesicle-generating microfluidic device", Physical Review Letter, vol. 86(18), pp. 4163-4166.
Tsai, Scott S H., et al., (2011) "Microfluidic immunomagnetic multi-target sorting—a model for controlling deflection of paramagnetic beads", Lab on a Chip, vol. 11(15), pp. 2577-2582.
Ullal, Adeeti V., et al., (2014) "Cancer cell profiling by barcoding allows multiplexed protein analysis in fine needle aspirates", Science Translation Medicine, vol. 6, Issue 219, pp. 1-22.
Vanapalli, Siva A., et al., (2009) "Hydrodynamic resistance of single confined moving drops in rectangular microchannels", Lab on a Chip, vol. 9, pp. 982-990.
Vickers, Jonathan A., et al., (2006) "Generation of Hydrophilic Poly(dimethylsiloxane) for High-Performance Microchip Electrophoresis", Anal. Chem, vol. 78(21), pp. 7446-7452.
Wang, Chao, et al., (2012) "Amphiphilic building blocks for self-assembly: from amphiphiles to supra-amphiphiles" Accounts of Chemical Research, vol. 45(4), pp. 608-618.
Wheeler, Aaron R., et al., (2005) "Digital microfluidics with in-line sample purification for proteomics analyses with MALDI-MS", Anal Chem. vol. 77(2), pp. 534-540.
Whitcombe, David, et al., (1999) "Detection of PCR products using self-probing amplicons and fluorescence" Nature biotechnology, vol. 17(8), pp. 804-807.
Whitesides, George M., (2006) "The origins and the future of microfluidics", Nature vol. 442, pp. 368-373.
Xia, Younan, et al., (1998) "Soft lithography", Annual Review of Materials Science, vol. 37, pp. 551-575.
Yu, Zhenming, et al., (2014) "Mung bean nuclease treatment increases capture specificity of microdroplet-PCR based targeted DNA enrichment", PLoS One vol. 9(7), e103491, pp. 1-7.
Zeng, Yong, et al., (2010) "High-Performance Single Cell Genetic Analysis Using Microfluidic Emulsion Generator Arrays", Anal Chem, vol. 82(8), pp. 3183-3190.
Zheng, Bo, et al., (2004) "Formation of droplets of in microfluidic channels alternating composition and applications to indexing of concentrations in droplet-based assays", Anal Chem., vol. 76, pp. 4977-4982.
Zhong, Qun, et al., (2011) "Multiplex digital PCR: breaking the one target per color barrier of quantitative PCR", Lab on a Chip, vol. 11 (13), pp. 2167-2174.
Zhu, Y Y., et al., (2001) "Reverse transcriptase template switching: a SMART approach for full-length cDNA library Construction", BioTechniques, vol. 30(4), pp. 892-897.
Zhu, Zhi, et al., (2012) "Highly sensitive and quantitative detection of rare pathogens through agarose droplet microfluidic emulsion PCR at the single-cell level", Lab on a Chip, vol. 12(20), pp. 3907-3913.

(56) References Cited

OTHER PUBLICATIONS

Zien, Tse-Fou, (1969) "Hydrodynamics of bolus flow—an analytical approach to blood flow in capillaries", Bull Math Biophys, vol. 31(4), pp. 681-694.
Morimoto et al. (2009) "Reconstruction of 3D Hierarchic Micro-Tissues using Monodisperse Collagen Microbeads", Micro Electro Mechanical Systems, IEEE 22nd International Conference, 56-59.
Morimoto et al. (2013) "Three-dimensional cell culture based on microfluidic techniques to mimic living tissues", Biomaterials Science, vol. 1, No. 3, 257-264.
Abate et al. (2009) "Beating Poisson encapsulation statistics using close-packed ordering" Lab Chip, 9: 2628-2631.
Abate et al. (2010) "High-throughput injection with microfluidics using picoinjectors" PNAS, 107(45): 19163-19166.
Abate et al. (2011) "Faster multiple emulsification with drop splitting" Lab Chip, 11(11): 1911-1915.
Abate et al. (2013) "DNA sequence analysis with droplet-based microfluidics" Lab Chip, 13(24): 4864-4869.
Abbaspourrad et al. (2015) "Label-free single-cell protein quantification using a dropbased mix-and-read system" Sci. Rep., 5: 12756.
Agargel "Agar-Agar" (2017) retrieved on Jun. 6, 2019 from https://web.archive.org/web/20170527222040/http://www.agargel.com.br/agar-tec-en.html, (3 pages).
Agresti et al. (2010) "Ultrahigh-throughput screening in drop-based microfluidics for directed evolution" PNAS, 107(9): 4004-4009.
Ahn et al. (2006) "Electrocoalescence of drops synchronized by size-dependent flow in microfluidic channels" Appl. Phys. Lett., 88: 264105.
Autour et al. (2017) "Ultrahigh-throughput improvement and discovery of enzymes using droplet-based microfluidic screening" Micromachines, 8(128): 1-21.
Baker (2012) "Digital PCR hits its stride" Nat. Methods, 9(6): 541-544.
Bjork et al. (2015) "Metabolite profiling of microfluidic cell culture conditions for droplet based screening" Biomicrojluidics, 9: 044128.
Blainey et al. (2014) "Dissecting genomic diversity, one cell at a time" Nat. Methods, 11(1): 19-21.
Brouzes et al. (2009) "Droplet microfluidic technology for single-cell high-throughput screening" PNAS, 106(3): 14195-14200.
Chang et al. (2012) "Single Molecule Enzyme-Linked Immunosorbent Assays: Theoretical Considerations" J Immunol Methods, 378(1-2): 102-115.
Chen et al. (2016) "Spinning micropipette liquid emulsion generator for single cell whole genome amplification" Lab Chip, 16: 4512-4516.
Chen et al. (2017) "Centrifugal micro-channel array droplet generation for highly parallel digital PCR" Lab Chip, 17: 235-240.
Civelek et al. (2014) "Systems genetics approaches to understand complex traits" Nat. Rev. Genet., 15(1): 34-48.
Collins et al. "The Poisson distribution and beyond: methods for microfluidic droplet production and single cell encapsulation" Lab Chip, 15: 3439-3459.
Costa et al. (2008) "Complex networks: The key to systems biology." Genet. Mol. Biol., 31(3) 591-601.
Dejournette et al. (2013) "Creating Biocompatible Oil-Water Interfaces without Synthesis: Direct Interactions between Primary Amines and Carboxylated Perfluorocarbon Surfactants" Anal Chem, 85(21): 10556-10564.
Elnifro et al. (2000) "Multiplex PCR: Optimization and Application in Diagnostic Virology" Clin. Microbial. Rev., 13(4): 559-570.
Fritzsch et al. (2012) "Single-Cell Analysis in Biotechnology, Systems Biology, and Biocatalysis" Annu. Rev. Chem. Biomol. Eng., 3:129-155.
Fu et al. (2015) "Uniform and accurate single-cell sequencing based on emulsion whole-genome amplification" PNAS, 112(38): 11923-11928.
Gielen et al. (2016) "Ultrahigh-throughput-directed enzyme evolution by absorbanceactivated droplet sorting (AADS)" PNAS, E7383-E7389.
Guo et al. (2012) "Droplet microfluidics for highthroughput" biological assays. Lab Chip, 2146-2155.
Griffiths et al. (2006) "Miniaturising the laboratory in emulsion droplets" Trends Biotechnol., 24: 395-402.
Halldorsson et al. (2015) "Advantages and challenges of microfluidic cell culture in polydimethylsiloxane devices" Biosens. Bioelectron., 63: 218-231.
Hindson et al. (2001) "High-throughput droplet digital PCR system for absolute quantitation of DNA copy number" Anal. Chem., 83: 8604-8610.
Holland et al. (1991) "Detection of specific polymerase chain reaction product by utilizing the 5'→3' exonuclease activity of Thermus aquaticus DNA polymerase" PNAS, 88(16): 7276-7280.
Holtze et al. (2008) "Biocompatible surfactants for water-in-fluorocarbon emulsions," Lab Chip, 8: 1632-1639.
Huang et al. (2017) "Collective generation of milliemulsions by step-emulsification" RSC Advances, 7: 14932-14938.
Joanicot et al. (2005) "Droplet control for microfluidics." Science, 309(5736): 887-888.
Katepalli et al. (2014) "Bose, A. Response of Surfactant Stabilized Oil-in-Water Emulsions to the Addition of Particles in an Aqueous Suspension" Langmuir, 30(43): 12736-12742.
Kim et al. (2017) "Measurement of copy number variation in single cancer cells using rapid-emulsification digital droplet MDA" Microsystems & Nanoengineering 3: 17018:1-7.
Kim et al. (2014) "Droplet Microfluidics for Producing Functional Microparticles" Langmuir, 30: 1473-1488.
Kimmerling et al. (2016) "A microfluidic platform enabling single-cell RNA-seq of multigenerational lineages" Nature Commun., 7: 10220.
Kolodziejczyk et al. (2015) "The Technology and Biology of Single-Cell RNA Sequencing" Mol. Cell, 58(4): 610-620.
Kumaresan et al. (2008) "High-Throughput Single Copy DNA Amplification and Cell Analysis in Engineered Nanoliter Droplets" Anal. Chem. 80: 3522-3529.
Lance e al. (2016) "Peering below the diffraction limit: robust and specific sorting of viruses with flow cytometry" Viral J, 13: 201.
Lim et al. (2013) "Ultrahigh-throughput sorting of microfluidic drops with flow cytometry" Lab Chip 13(23): 4563-4572.
Macosko et al. (2015) "Highly parallel genome-wide expression profiling of individual cells using nanoliter droplets" Cell, 161: 1202-1214.
Margulies et al. (2005) "Genome sequencing in microfabricated high-density picolitre reactors" Nature, 437: 376-380.
Mashaghi et al. (2016) Droplet microfluidics: A tool for biology, chemistry and nanotechnology TrAC—Trends Anal. Chem., 82: 118-125.
Mazutis et al. (2013) "Single-cell analysis and sorting using droplet-based microfluidics" Nat. Protoc., 8(5): 870-891.
Nishikawa et al. (2015) "Monodisperse Picoliter Droplets for Low-Bias and Contamination-Free Reactions in Single-Cell Whole Genome Amplification" PLoS One, 10(9): e0138733: 1-15.
Novak et al. (2011) "Single Cell Multiplex Gene Detection and Sequencing Using Microfluidically-Generated Agarose Emulsions" Agnew Chem Int Ed Engl, 50(2): 390-395.
Pinheiro et al. (2012) "Evaluation of a droplet digital polymerase chain reaction format for DNA copy number quantification" Anal. Chem., 84: 1003-1011.
Priest et al. (2006) "Controlled electrocoalescence in microfluidics: Targeting a single lamella" Appl. Phys. Lett., 89: 134101 (4 pages).
Romero et al. (2015) "Dissecting enzyme function with microfluidic-based deep mutational scanning" PNAS, 112(23): 7159-7164.
Sandberg et al. (2009) "Flow cytometry for enrichment and titration in massively parallel DNA sequencing" Nucleic Acids Res., 37(8): e63.
Shembekar et al. (2016) "Droplet-based microfluidics in drug discovery, transcriptomics and high-throughput molecular genetics" Lab Chip, 16: 314-1331.
Sidore et al. (2016) "Enhanced sequencing coverage with digital droplet multiple displacement amplification" Nucleic Acids Research, 44(7): e66: 1-9.

(56) References Cited

OTHER PUBLICATIONS

Song et al. (2006) "On-Chip Titration of an Anticoagulant Argatroban and Determination of the Clotting Time within Whole Blood or Plasma Using a Plug-Based Microfluidic System" Anal. Chem., 78(14): 4839-4849.
Soon et al (2013) "High-throughput sequencing for biology and medicine" Mol. Syst. Biol., 9(64): 1-14.
Spencer et al (2016) "Massively parallel sequencing of single cells by epicPCR links functional genes with phylogenetic markers" ISME J, 10: 427-436.
Spies et al. (2017) "Genome-wide reconstruction of complex structural variants using read clouds" Nat. Methods, 14(9): 915-920.
Sukovich et al. (2017) "Sequence specific sorting of DNA molecules with FACS using 3dPCR" Sci. Rep., 7:39385.
Taly et al. (2013) "Multiplex picodroplet digital PCR to detect KRAS mutations in circulating DNA from the plasma of colorectal cancer patients" Clin. Chem., 59: 1722-1731.
Tamminen et al. (2015) "Single gene-based distinction of individual microbial genomes from a mixed population of microbial cells" Frontiers in Microbiology, 6(195): 1-10.
Tran et al (2013) From tubes to drops: dropletbased microfluidics for ultrahigh-throughput biology. J Phys. D. Appl. Phys., 46: 114004.
Utada et al. (2007) Dripping to Jetting Transitions in Coflowing Liquid Streams: Phys. Rev. Lett., 99: 094502 (4 pages).
Weaver et al (2014) "Advances in high-throughput single-cell microtechnologies" Curr. Opin. Biotechnol., 0: 114-123.
Yan et al. (2017) "Intestinal Enteroendocrine Lineage Cells Possess Homeostatic and Injury-Inducible Stem Cell Activity" Cell Stem Cell, 21: 78-90.
Zilionis et al. (2017) Single-cell barcoding and sequencing using droplet microfluidics. Nat. Protoc., 12(1): 44-73.
Zhu et al. (2017) "Hydrogel Droplet Microfluidics for High-Throughput Single Molecule/Cell Analysis" Ace. Chem. Res., 50(1): 22-31.
Abate, Adam R. et al (2011) Air-bubble-triggered drop formation in microfluidics, Lab Chip, 11, 1713-1716.
Cheung, V.G., et al. (1996) Whole genome amplification using a degenerate oligonucleotide primer allows hundreds of genotypes to be performed on less than one nanogram of genomic DNA, Proc. Natl. Acad. Sci. U.S.A., 93.
Dean et al. (2002) Comprehensive human genome amplification using multiple displacement amplification, Proc. Natl. Acad. U.S. A., 99, 5261-5266.
Dean et al. (2001) Rapid amplification of plasmid and phage DNA using Phi29 DNA polymerase and multiply-primed rolling circle amplification, Genome Res., 11, 1095-1099.
Esteban, et al. (1993) Fidelity of phi29 DNA Polymerase, J. Biol. Chem, 268, 2719-2726.
Gole, et al. (2013) Massively parallel polymerase cloning and genome sequencing of single cells using nanoliter microwells Nat. Biotechnol., 31 1126-32.
Hosono, et al. (2003) Unbiased whole-genome amplification directly from clinical samples Genome Res., 13 954-964.
Marcy et al. (2007) Dissecting biological 'dark matter' with single-cell genetic analysis of rare and uncultivated TM7 microbes from the human mounth Proc. Natl. Acad. Sci. USA., 104 11889-1189.
Marcy et al. (2007) Nanoliter reactors improve multiple displacement amplification of genomes from single cells PLoS Genet. 3 1702-1708.
Pan, et al. (2008) A procedure for highly specific, sensitive, and unbiased whole-genome amplification Proc. Natl. Acad. Sci. U.S. A., 105 15499-15504.
Raghunathan, et al. (2005) Genomic DNA Amplification from a Single Bacterium Genomic DNA Amplification from a Single Bactterium Appl. Environ. Microbiol., 71 3342-3347.
Rodrigue, et al. (2009) Whole genome amplification and de novo assembly of single bacterial cells PloS One, vol. 4, 9, e6864 1-10.
Romanowsky, et al. (2012) High throughput production of single core double emulsions in a parallelized microfluidic device Lab Chip, 12 802.
Ross, et al. (2013) Characterizing and measuring bias in sequence data Genome Biol., 14, R51 1-20 2013Ross, et al. Characterizing and measuring bias in sequence data Genome Biol., 14, R51 1-20.
Spits, C. et al. (2006) Whole-genome multiple displacement amplification from single cells Nature protocols, 1(4) 1965-1970.
Telenius et al. (1992) Degenerate oligonucleotide-primed PCR: general amplification of target DNA by a single degenerate primer Genomics, 13 718-725.
Thompson, C., et al. (2013) Adhesive-based bonding technique for PDMS microfluidic devices Lab Chip, 13 632-635.
Yoon, et al. (2011) Single-cell genomics reveals organismal interactions in uncultivated marine protists. Science, 333 714-717.
Zhang, et al. (1992) Whole genome amplification from a signal cell: implications for genetic analysis Proc. Natl. Acad. Sci. U.S. A., 89 5847-5851.
Zong, et al. (2012) Genome-wide detection of single-nucleotide and copy-number variations of a single human cell Science, 338 1622-1626.
Geng et al (2014) Single-Cell Forensic Short Tandem Repeat Typing within Microfluidic Droplets, Analytical Chemistry, pp. 703-712.
Nesterov-Mueller, et al. (2014) Particle-Based Microarrays of Oligonucleotides and Oligopeptides, Microarrays ISSN 2076-3905, pp. 245-262.
Asari et al., (2013) "Universal Fluorescent labeling of amplification products using locked nucleic acids," Electrophoresis. vol. 34, pp. 448-455.
ThermoFisher Scientific, (2012) Alkaline Agarose Gel Electrophoresis, https://assets.thermofisher.com/TFS-Assets/LSG/manuals/MAN0011923_Alkaline_agarose_Gel_Electrophoresis_UG.pdf (2012).
Lim, et al., (2015) PCR-Activated Cell Sorting for Cultivation Free Enrichment and Sequencing of Rare Microbes, PLoS ONE, vol. 10, Issue 1, e0113549.
Lorenceau et al., "Generation of Polymerosomes from Double-Emulsions", Langmuir, vol. 21, 9183-8186, 2005.
Walde et al., "Giant Vesicles; Preparations and Applications", ChemBioChem, vol. 11, 848-865, 2010.
Courtois et al. (2009) Controlling the Retention of Small Molecules in Emulsion Microdroplets for Use in Cell-Based Assays, Anal Chem, vol. 81, pp. 3008-3016.
Niu et al. (2012) Building droplet-based microfluidic systems for biological analysis, vol. 40, pp. 615-623.

* cited by examiner

FIG. 2

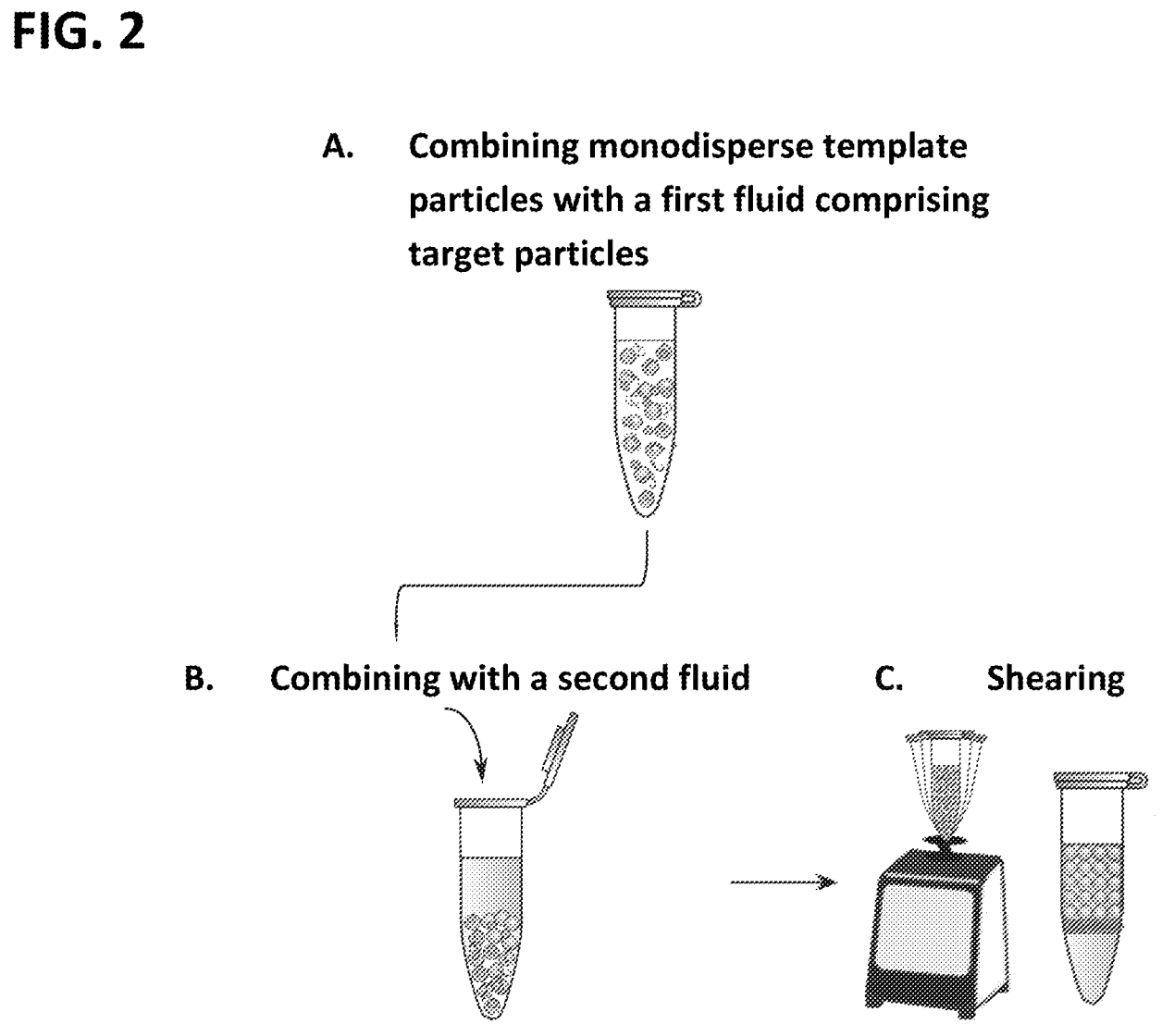

A. Combining monodisperse template particles with a first fluid comprising target particles B. Combining with a second fluid C. Shearing

FIG. 3

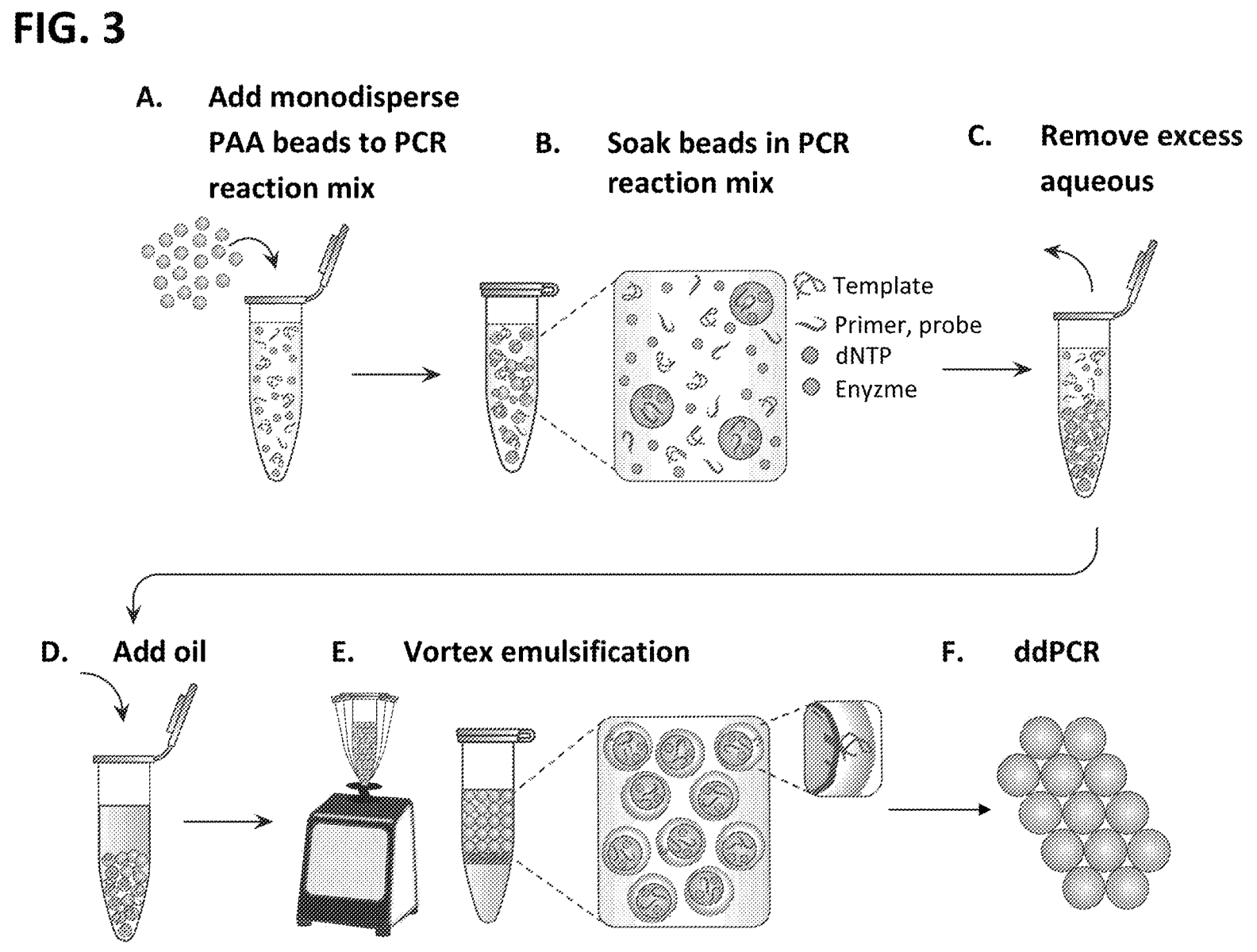

A. Add monodisperse PAA beads to PCR reaction mix

B. Soak beads in PCR reaction mix

Template
Primer, probe
dNTP
Enyzme

C. Remove excess aqueous

D. Add oil

E. Vortex emulsification

F. ddPCR

A.
No particle
Vortexed
Microfluidics
B.
Shaken emulsion with particle
No detergent
0.5% triton
0.2% IGEPAL
PAA
PEG
Agarose
Droplets (%)
No det.
0.5% triton
0.2% IGEPAL
No detergent
0.5% triton
0.2% IGEPAL
C.
% of droplets
Vortexed No Particle
Microfluidics No Particle
Vortexed PAA
Diameter [um]

Template dilution series
A.
Negative control
1/1000
1/100
1/10
1
400 μm
1/10 template
B.
Fluorescence [AU]
40
30
20
10
10
20
30
40
Diameter [μm]
Diam
10
20
30
40
50
C.
Poisson estimator, λ
$10^0$
$10^{-1}$
$10^{-2}$
$10^2$
$10^3$
$10^4$
Template [copies/μL]

FIG. 9

Poisson estimator, λ

Template [copies/μL]

A.
Multiplex PCR
Merged
Lambda
Yeast
B.
Capture cell and grow
0 hr
10 hr
100 µm

FIG. 14A
BAC polyacryl-amide beads
Drop-seq beads
Single cells
Proteinase K
Hybridization buffer
Oil with 2-Mer-captoethanol
FIG. 14B
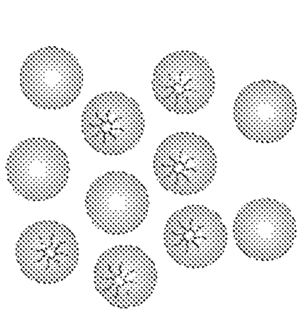
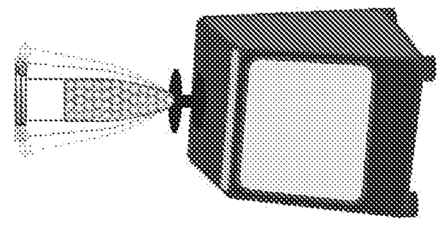
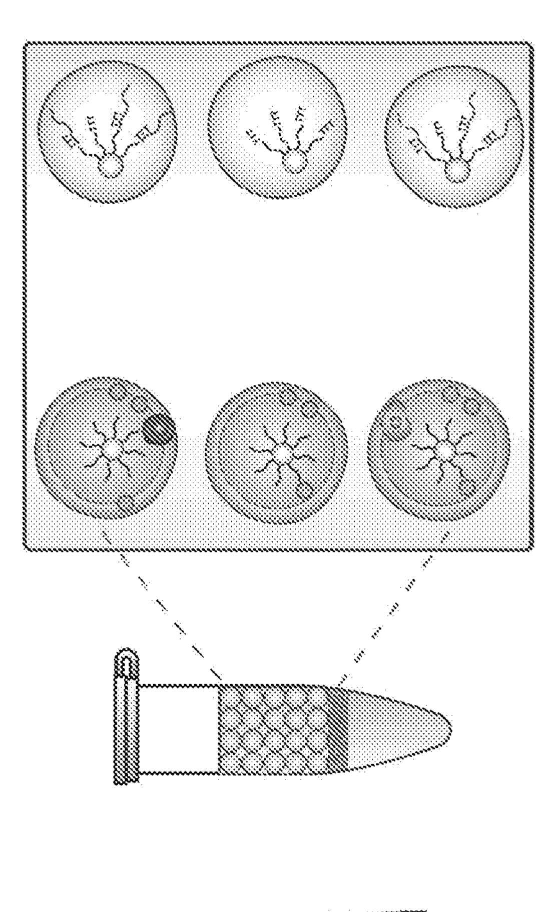

FIG. 14C

PCR & NexteraXT & Sequencing

ATCGATCGATCGATCGATCG ...... CCGGCCGG

Read1 21bp
For cell barcode and UMI

Read2 50bp
For gene identification

A
Particles with Drop-seq beads
B
PIPs with Drop-seq beads
C
D
PIPs with Drop-seq beads and Cells (calcein green) (prelysis and postlysis)

METHOD OF GENERATING MONODISPERSE EMULSIONS

CROSS REFERENCE

This application claims the benefit of U.S. Provisional Patent Application No. 62/565,976, filed Sep. 29, 2017, which application is incorporated herein by reference in its entirety.

GOVERNMENT SUPPORT

This invention was made with government support under grant nos. AR068129, R01 EB019453 and R21 HG007233 awarded by the National Institutes of Health; grant no. HR0011-12-C-0065 by the Defense Advanced Research Projects Agency; and grant no. DBI1253293 awarded by the National Science Foundation. The government has certain rights in the invention.

INTRODUCTION

Droplet microfluidics advances laboratory automation by reducing reaction volumes to picoliters and increasing processing to kilohertz. Microfluidic devices form, process, and sort droplets suspended in a carrier fluid; each droplet affords an isolated "test tube" in which a reaction can be performed. The throughput of the approach, combined with the tiny reagent consumption, provide unprecedented potential for a new era of high throughput science. In addition, monodisperse droplet-compartmentalization is a versatile approach for applications across biology. However, the general requirement of microfluidics for droplet encapsulation is a significant barrier to most researchers who rarely have access to advanced microfluidic systems. The inability to immediately translate droplet microfluidic advances to researchers impedes the implementation of new, useful droplet techniques. The present disclosure addresses the above issues and provides related advantages.

SUMMARY

The methods described herein, referred to as particle-templated emulsification (PTE), provide an improved approach for generating a monodisperse emulsion that encapsulates target particles of interest without requiring the use of a microfluidic device. The present disclosure is based in part on the surprising discovery that monodisperse droplets may be effectively obtained by using monodisperse particles to template the formation of droplets, which can include, e.g., monodisperse single-emulsion droplets, multiple-emulsion droplets, or Giant Unilamellar Vesicles (GUV) (also referred to herein as liposomes), without destroying the integrity of the droplets.

In exemplary embodiments, the disclosed methods for generating a monodisperse emulsion include combining a plurality of monodisperse template particles with a first fluid to provide a first mixture, wherein the first fluid includes a plurality of target particles; combining the first mixture with a second fluid to provide a second mixture, wherein the second fluid is immiscible with the first fluid; and shearing the second mixture such that a plurality of the monodisperse template particles are encapsulated in a plurality of monodisperse droplets in the second fluid, thereby providing a plurality of monodisperse droplets including the first fluid, one of the monodisperse template particles, and one of the plurality of target particles. Generating a monodisperse emulsion as described herein may be performed without microfluidic control.

In some embodiments, the target particles may include a heterogeneous population of cells, viruses, and/or nucleic acids. In some embodiments, the target particles may be diluted prior to encapsulation, e.g., so as to encapsulate a controlled number of cells, viruses, and/or nucleic acids in the monodisperse droplets. Nucleic acid synthesis reagents, e.g., isothermal nucleic acid amplification reagents, non-specific nucleic acid amplification reagents (e.g., MDA reagents), and/or PCR reagents, may be co-encapsulated in the monodisperse droplets, e.g., along with one or more target particles, or added to the monodisperse droplets at a later time using one or more of the methods described herein to facilitate downstream detection, sorting, and/or analysis as described herein.

Multiple-emulsion droplets as described herein may be formed, for example, by combining a first fluid including a plurality of target particles, e.g., cells, viruses, and/or nucleic acids, along with nucleic acid synthesis reagents, with a plurality of monodisperse template particles to provide a first mixture; combining the first mixture with a second fluid to provide a second mixture, wherein the second fluid is immiscible with the first fluid; shearing the second mixture such that a plurality of the monodisperse template particles are encapsulated in a plurality of monodisperse droplets in the second fluid, thereby providing a plurality of monodisperse droplets including the first fluid, one of the monodisperse template particles, and one of the plurality of target particles; combining the second mixture with a third fluid, wherein the third fluid is immiscible with the second fluid; and shearing the third mixture to encapsulate one or more of the monodisperse droplets, with or without the monodisperse template particles, in one or more droplets in the third fluid to provide one or more double-emulsion droplets. In some embodiments, the third fluid is immiscible with the first and second fluids.

GUVs may be generated from multiple-emulsion droplets (e.g. double-emulsion droplets) by inducing the multiple-emulsion droplets to undergo dewetting, wherein the second fluid is expunged, leaving behind a membrane of surfactant with a small droplet of the second fluid adhered to the outside of the membrane.

Monodisperse template particles for use in methods as described herein may be generated, for example, by flowing a first fluid, e.g., a liquid gel precursor, in a channel of a microfluidic device; and contacting the first fluid with a second fluid, wherein the second fluid is immiscible with the first fluid, e.g., using a single-emulsion droplet maker. In some embodiments, parallel droplet generation techniques including serial splitting and distribution plates can be used to form the monodisperse template particles more rapidly. The monodisperse single-emulsion droplets are then solidified by triggering gelation, e.g. polymerizing the gel matrix within the droplets or crosslinking the matrix. In some embodiments, a surfactant may be used to prevent contacting monodisperse template particles from coalescing with each other. One or more steps of the method for generating monodisperse template particles may be performed under microfluidic control.

In some embodiments, a sample including target particles, e.g., cells, is encapsulated in monodisperse single-emulsion droplets prepared as described herein or multiple-emulsion droplets or GUVs prepared as described herein and subjected to isothermal nucleic acid amplification conditions and/or nucleic acid amplification conditions as described herein. In some embodiments, the encapsulated cells are subjected to one or more cell lysing techniques, such as proteinase k digestion or thermal lysis. Isothermal nucleic acid amplification assays or nucleic acid amplification assays specific to the cells of interest can cause monodisperse single-emulsion droplets prepared as described herein or multiple-emulsion droplets or GUVs prepared as described herein containing the cells of interest, or nucleic acids originating from the cells of interest, to become detectably labeled, e.g., fluorescently labeled. The cells and/or the cellular nucleic acids may then be recovered by sorting the monodisperse single-emulsion droplets or multiple-emulsion droplets or GUVs and recovering their contents via droplet rupture, e.g., through chemical or electrical means. The above steps may be followed by one or more sequencing steps, e.g., one or more next generation sequencing techniques.

Additional amplification reactions which may be performed in monodisperse single-emulsion droplets prepared as described herein or multiple-emulsion droplets or GUVs prepared as described herein, include, e.g., strand displacement amplification (SDA), and rolling circle amplification (RCA).

In one embodiment, a method for enriching for a target nucleic acid sequence is provided, wherein the method includes encapsulating a plurality of target particles, including nucleic acids in a plurality of monodisperse single-emulsion droplets prepared as described herein or multiple-emulsion droplets or GUVs prepared as described herein; introducing Multiple Displacement Amplification (MDA) reagents, polymerase chain reaction (PCR) reagents, and/or other nucleic acid synthesis, e.g., amplification reagents, including appropriate primers, into the single-emulsion droplets or multiple-emulsion droplets or GUVs; incubating the monodisperse single-emulsion droplets or multiple-emulsion droplets or GUVs under conditions sufficient for PCR amplification, or conditions sufficient for MDA amplification followed by conditions sufficient for PCR amplification, to produce PCR amplification products, wherein suitable PCR primers may include one or more primers that each hybridize to one or more oligonucleotides incorporating the target nucleic acid sequence, and wherein the PCR amplification products do not include the entire target nucleic acid sequence; introducing a detection component into the monodisperse single-emulsion droplets or multiple-emulsion droplets or GUVs either before or after the incubating; detecting the presence or absence of the PCR amplification products by detection of the detection component, wherein detection of the detection component indicates the presence of PCR amplification products and the target nucleic acid sequence; and sorting the monodisperse single-emulsion droplets or multiple-emulsion droplets or GUVs based on detection of the detection component, wherein the sorting separates the monodisperse single-emulsion droplets or multiple-emulsion droplets or GUVs including the PCR amplification products and the target nucleic acid sequence, when present, from the monodisperse single-emulsion droplets or multiple-emulsion droplets or GUVs which do not include the PCR amplification products and the target nucleic acid sequence; and pooling the nucleic acid sequences from the sorted monodisperse single-emulsion droplets or multiple-emulsion droplets or GUVs to provide an enriched pool of target nucleic acid sequences, when present. The above steps may be followed by one or more sequencing steps, e.g., one or more next generation sequencing techniques.

As described herein, the term “next-generation sequencing” generally refers to advancements over standard DNA sequencing (e.g., Sanger sequencing). Although standard DNA sequencing enables the practitioner to determine the precise order of nucleotides in the DNA sequence, next-generation sequencing also provides parallel sequencing, during which millions of base pair fragments of DNA can be sequenced in unison. Standard DNA sequencing generally requires a single-stranded DNA template molecule, a DNA primer, and a DNA polymerase in order to amplify the DNA template molecule. Next-generation sequencing facilitates high-throughput sequencing, which allows for an entire genome to be sequenced in a significantly shorter period of time relative to standard DNA sequencing. Next-generation sequencing may also facilitate in identification of disease-causing mutations for diagnosis of pathological conditions. Next-generation sequencing may also provide information on the entire transcriptome of a sample in a single analysis without requiring prior knowledge of the genetic sequence.

Any suitable non-specific nucleic acid amplification methods and reagents, e.g., MDA methods and reagents, may be utilized in connection with the disclosed methods provided that such methods and reagents are compatible with any additional, e.g., subsequent, amplification steps and or reagents of the method, e.g., PCR amplification steps and reagents. An example of a suitable MDA polymerase, which may be used in combination with a Taq DNA polymerase is a Bst polymerase. Bst polymerase may have advantages over other MDA polymerases, such as phi29 polymerase, since Bst polymerase is efficient over a wider temperature range and is active under similar buffer conditions to Taq DNA polymerase.

In practicing the subject methods, a wide range of different PCR-based assays may be employed, such as quantitative PCR (qPCR) and digital droplet PCR. The number and nature of primers used in such assays may vary, based at least in part on the type of assay being performed, the nature of the biological sample, and/or other factors. In certain aspects, the number of primers that may be added to a monodisperse droplet, e.g., a monodisperse single-emulsion droplet, a multiple-emulsion droplet, or a GUV may be 1 to 100 or more, and/or may include primers to detect from about 1 to 100 or more different genes (e.g., oncogenes). In addition to, or instead of, such primers, one or more probes (e.g., TaqMan® probes) may be employed in practicing the subject methods.

As used herein, the terms “drop” and “droplet” are used interchangeably to refer to tiny, generally spherical, microcompartments containing at least a first fluid, e.g., an aqueous phase (e.g., water), bounded by a second fluid (e.g., oil) which is immiscible with the first fluid. In some embodiments, the second fluid will be an immiscible phase carrier fluid. Droplets, including, e.g., single-emulsion and multiple-emulsion droplets, generally range from about 0.1 to about 1000 μm in diameter or largest dimension, and may be used to encapsulate cells, DNA, enzymes, and other components. In some embodiments, droplets, e.g., single-emulsion and multiple-emulsion droplets, have a diameter or largest dimension of about 1.0 μm to 1000 μm, inclusive, such as about 1.0 μm to about 750 μm, about 1.0 μm to about 500 μm, about 1.0 μm to about 250 μm, about 1.0 μm to about 200 μm, about 1.0 μm to about 150 μm, about 1.0 μm to about 100 μm, about 1.0 μm to about 10 μm, or about 1.0 μm to about 5 μm, inclusive. In some embodiments, droplets, e.g., single-emulsion and multiple-emulsion droplets, have a diameter or largest dimension of about 10 μm to about 200 μm, e.g., about 10 μm to about 150 μm, about 10 μm to about 125 μm, or about 10 μm to about 100 μm.

GUVs, which may be formed from double-emulsion droplets, are generally of a similar size as the double-emulsion droplets from which they originate. Accordingly, GUVs as described herein may range from about 0.1 to about 1000 μm in diameter or largest dimension. In some embodiments, GUVs as described herein have a diameter or largest dimension of about 1.0 μm to 1000 μm, inclusive, such as 1.0 μm to 750 μm, 1.0 μm to 500 μm, 1.0 μm to 250 μm, 1.0 μm to 200 μm, 1.0 μm to 150 μm 1.0 μm to 100 μm, 1.0 μm to 10 μm, or 1.0 μm to 5 μm, inclusive. In some embodiments, GUVs as described herein have a diameter or largest dimension of about 10 μm to about 200 μm, e.g., about 10 μm to about 150 μm, about 10 μm to about 125 μm, or about 10 μm to about 100 μm.

The droplets, e.g., monodisperse single-emulsion droplets or multiple-emulsion droplets or GUVs, themselves may vary, including in size, composition, contents, and the like. Monodisperse single-emulsion droplets or multiple-emulsion droplets or GUVs may generally have an internal volume of from about 0.001 to 1000 picoliters or more, e.g., from about 0.001 picoliters to about 0.01 picoliters, from about 0.01 picoliters to about 0.1 picoliters, from about 0.1 picoliters to about 1 picoliter, from about 1 picoliter to about 10 picoliters, from about 10 picoliters to about 100 picoliters, or from about 100 picoliters to about 1000 picoliters or more. Further, droplets may or may not be stabilized by surfactants and/or particles.

The means by which reagents are added to a droplet, e.g., a monodisperse single-emulsion droplet or multiple-emulsion droplet or GUV may vary greatly. Reagents may be added in one step or in multiple steps, such as 2 or more steps, 4 or more steps, or 10 or more steps. In certain aspects, reagents may be added to monodisperse single-emulsion droplets or multiple-emulsion droplets or GUVs via one or more encapsulation and rupture steps. For example, in some embodiments, the disclosed method may include a step of encapsulating a plurality of target particles, e.g., a virus, cell or nucleic acid, in a first monodisperse droplet or GUV, encapsulating one or more reagents and the first monodisperse droplet or GUV in a second droplet or GUV, and rupturing the first monodisperse droplet or GUV thereby bringing the plurality of target particles into contact with the one or more reagents.

In one such embodiment, cells are encapsulated into double emulsion droplets or GUVs using monodisperse single-emulsion droplets prepared as described herein along with a suitable lysis buffer, incubated under conditions sufficient for cell lysis and/or protein digestion, and heated to inactivate proteases. The double emulsions or GUVs may then be encapsulated into double emulsions or GUVs containing suitable nucleic acid synthesis reagents and ruptured so as to release their contents into the encapsulating double emulsions or GUVs, thereby mixing the cell lysate with the nucleic acid synthesis reagents. The remaining double emulsions or GUVs may then be incubated under conditions suitable for nucleic acid amplification. Due to their combined hydrophilic and hydrophobic properties, double emulsions or GUVs have wide applicability in drug delivery, including drug encapsulation and delivery; cosmetic uses, including cosmetics encapsulation; and biomedical research including in vitro compartmentalization and strain isolation in synthetic biology with FACS-based double emulsion sorting and membrane protein functional studies.

As a variation on the above method, cells may be encapsulated into monodisperse single emulsions with a suitable lysis buffer. Following an optional protease inactivation step, monodisperse single emulsions may then be merged via droplet merger with monodisperse single emulsions containing suitable nucleic acid synthesis reagents. The merged monodisperse single-emulsion droplets may then be encapsulated into double emulsions or GUVs for subsequent nucleic acid amplification. Alternatively, cells may be encapsulated into single emulsions with a suitable lysis buffer and then, following an optional protease inactivation step, encapsulated into nucleic acid amplification reagent-containing double emulsions or GUVs. It should be noted that steps of encapsulation into single emulsions and steps of encapsulation into double emulsions may be performed without the use of a microfluidic device.

As mentioned above, where monodisperse single-emulsion droplets are utilized as described herein, a variety of techniques applicable to single emulsion droplets may be utilized, including, e.g., droplet coalescence, picoinjection, multiple droplet coalescence, and the like, as shall be described more fully herein. In certain embodiments, reagents are added by a method in which the injection fluid itself acts as an electrode. The injection fluid may contain one or more types of dissolved electrolytes that permit it to be used as such. Where the injection fluid itself acts as the electrode, the need for metal electrodes in the microfluidic chip for the purpose of adding reagents to a droplet may be obviated. In certain embodiments, the injection fluid does not act as an electrode, but one or more liquid electrodes are utilized in place of metal electrodes.

Various ways of detecting the absence or presence of nucleic acid amplification products may be employed, using a variety of different detection components. Detection components of interest include, but are not limited to, fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy®3 dye (CAS (Chemical Abstract Services) number 146368-16-3; IUPAC (International Union of Pure and Applied Chemistry) name 3-[2-[(E,3E)-3-[1-(5-carboxypentyl)-3,3-dimethylindol-2-ylidene]prop-1-enyl]-3,3-dimethylindol-1-ium-1-yl]propane-1-sulfonate), Cy®3.5 dye (CAS number 189767-45-1; IUPAC name (2Z)-2-[(E)-3-[3-(5-carboxypentyl)-1,1-dimethyl-6,8-disulfobenzo[e]indol-3-ium-2-yl]prop-2-enylidene]-3-ethyl-1,1-dimethyl-6-sulfobenzo[e]indole-8-sulfonate), Cy®5 dye (CAS number 144377 May 9; IUPAC name 3-[2-[(1E,3E,5E)-5-[1-(5-carboxypentyl)-3,3-dimethylindol-2-ylidene]penta-1,3-dienyl]-3,3-dimethylindol-1-ium-1-yl]propane-1-sulfonate), Cy®7 dye (CAS number 169799-14-8; IUPAC name (2Z)-2-[(2E,4E,6E)-7-[1-(5-carboxypentyl)-3,3-dimethyl-5-sulfoindol-1-ium-2-yl]hepta-2,4,6-trienylidene]-1-ethyl-3,3-dimethylindole-5-sulfonate), Texas Red® dye (CAS number 82354-19-6; IUPAC name 5-chlorosulfonyl-2-(3-oxa-23-aza-9-azoniaheptacyclo[17.7.1.15,9.02,17.04,15.023,27.013,28]octacosa-1 (27),2 (17),4,9 (28), 13,15,18-heptaen-16-yl) benzenesulfonate), Pacific Blue™ dye (CAS number 215868-31-8; IUPAC name 6,8-difluoro-7-hydroxy-2-oxochromene-3-carboxylic acid), Oregon Green 488 (CAS number 195136-58-4; IUPAC name 2-(2,7-difluoro-3-hydroxy-6-oxoxanthen-9-yl)benzoic acid), Alexa Fluor® 488 dye (CAS number 247144-99-6; IUPAC name dilithium; 3-amino-9-[2-carboxy-5-(2,3,5,6-tetrafluorophenoxy) carbonylphenyl]-6-iminoxanthene-4,5-disulfonate), Alexa Fluor® 532 dye (CAS number 222159-92-4; IUPAC name 12-[4-(2,5-dioxopyrrolidin-1-yl)oxycarbonylphenyl]-

7,8,8,16,16,17-hexamethyl-2-oxa-6,18-diazapentacyclo [11.7.0.0$^{3,11}$.0$^{5,9}$.0$^{15,19}$]icosa-1 (20),3,5,9,11,13,15 (19)-heptaene-4,20-disulfonic acid), Alexa Fluor® 546 dye (CAS number 247145-23-9; IUPAC name sodium; 13-[2-carboxy-3,4,6-trichloro-5-[2-[[6-(2,5-dioxopyrrolidin-1-yl)oxy-6-oxohexyl]amino]-2-oxoethyl]sulfanylphenyl]-7,7,9,17,19,19-hexamethyl-2-oxa-6,20-diazapentacyclo[12.8.0.0$^{3,12}$.0$^{5,}$ $_{10}$.0$^{16,21}$]docosa-1 (14),3,5, 10,12,15,21-heptaene-4,22-disulfonate;hydron), Alexa Fluor® 555 dye (CAS number 644990-77-2; 4-(3-amino-6-imino-4,5-disulfoxanthen-9-yl) benzene-1,3-dicarboxylic acid), Alexa Fluor® 568 dye (CAS number 247145-38-6; IUPAC name 4-(2,5-dioxopyrrolidin-1-yl)oxycarbonyl-2-[7,7,19,19-tetramethyl-9,17-bis (sulfomethyl)-2-oxa-6,20-diazapentacyclo[12.8.0.0$^{3,12}$.0$^{5,}$ $_{10}$.0$^{16,21}$]docosa-1 (14),3,5,8,10,12, 15, 17,21-nonaen-13-yl] benzoic acid), Alexa Fluor® 594 dye (CAS number 247145-86-4; IUPAC name [13-[2-carboxy-5-(2,5-dioxopyrrolidin-1-yl)oxycarbonylphenyl]-6,7,7,19,19,20-hexamethyl-17-(sulfomethyl)-2-oxa-20-aza-6-azoniapentacyclo[12.8.0.0$^{3,}$ $_{12}$.0$^{5,10}$. 0$^{16,21}$]docosa-1(14),3,5,8,10, 12, 15, 17,21-nonaen-9-yl]methanesulfonate), Alexa Fluor® 647 dye (CAS number 400051-23-2; 2-[5-[3,3-dimethyl-5-sulfo-1-(3-sulfopropyl) indol-1-ium-2-yl]penta-2,4-dienylidene]-3-methyl-3-[5-oxo-5-(6-phosphonooxyhexylamino) pentyl]-1-(3-sulfopropyl) indole-5-sulfonic acid), JOE™ dye (CAS number 113394-23-3; IUPAC name (2,5-dioxopyrrolidin-1-yl) 4',5'-dichloro-3',6'-dihydroxy-2',7'-dimethoxy-1-oxospiro [2-benzofuran-3,9'-xanthene]-5-carboxylate), Lissamine, Rhodamine Green™ dye (CAS number 189200-71-3; IUPAC name [6-amino-9-(2,4-dicarboxyphenyl) xanthen-3-ylidene]azanium), BODIPY (IUPAC name 2,2-difluoro-3-aza-1-azonia-2-boranuidatricyclo[7.3.0.03,7]dodeca-1 (12),4,6,8,10-pentaene), fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ (IUPAC name 2-[[(2R)-2-[bis(carboxymethyl)amino]-3-14-(carbamothioylamino)phenyl]propyl]-[(1S,2S)-2-[bis (carboxymethyl)amino|cyclohexyl]amino]acetic acid), VIC (IUPAC name 2'-chloro-7'phenyl-1,4-dichloro-6-carboxy-fluorescein), NED (IUPAC name 2'-chloro-5'-fluoro-7',8'-benzo-1,4-dichloro-6-carboxyfluorescein), PET (IUPAC name Apr. 12, 2012-(4-carbamimidoylphenoxy)ethoxy-|ethoxy|benzenecarboximidamide), SYBR (IUPAC name N,N-dimethyl-N'-[4-[(E)-(3-methyl-1,3-benzothiazol-2-ylidene)methyl]-1-phenylquinolin-1-ium-2-yl]-N'-propyl-propane-1,3-diamine), PicoGreen® (IUPAC name N'-[3-(dimethylamino) propyl]-N,N-dimethyl-N'-14-[(E)-(3-methyl-1,3-benzothiazol-2-ylidene)methyl]-1-phenylquinolin-1-ium-2-yl|propane-1,3-diamine), and the like. Detection components may include beads (e.g., magnetic or fluorescent beads, such as Luminex beads) and the like. In certain aspects, detection may involve holding a monodisperse droplet at a fixed position during thermal cycling so it can be repeatedly imaged. Such repeated imaging may involve the use of a Megadroplet Array, as shall be described more fully herein. In certain aspects, detection may involve fixing and/or permeabilizing one or more cells in one or more monodisperse droplets, e.g., one or more multiple-emulsion monodisperse droplets, or GUVs.

Suitable subjects for the methods disclosed herein include mammals, e.g., humans. The subject may be one that exhibits clinical presentations of a disease condition, or has been diagnosed with a disease. In certain aspects, the subject may be one that has been diagnosed with cancer, exhibits clinical presentations of cancer, or is determined to be at risk of developing cancer due to one or more factors such as family history, environmental exposure, genetic mutation(s), lifestyle (e.g., diet and/or smoking), the presence of one or more other disease conditions, and the like. In certain aspects, the subject may be one that has been diagnosed with a microbial infection, exhibits clinical presentations of a microbial infection, or is determined to be at risk of developing a microbial infection due to one or more factors such as family history, environmental exposure, genetic mutation(s), lifestyle (e.g., diet and/or travel), the presence of one or more other disease conditions, and the like. In certain aspects, the subject may be one that has been diagnosed with a viral infection, exhibits clinical presentations of a viral infection, or is determined to be at risk of developing a viral infection due to one or more factors such as family history, environmental exposure, genetic mutation(s), lifestyle (e.g., diet and/or travel), the presence of one or more other disease conditions, and the like.

Microfluidic devices used to generate monodisperse template particles for use in the preparation of monodisperse droplets, include, but are not limited to, those described in U.S. Patent Application Publication No. 2015/0232942, the disclosure of which is incorporated by reference herein. In some embodiments, a microfluidic system including a nucleic acid amplification region and a detection region may be used in connection with the processing/incubation and analysis of monodisperse droplets prepared as described herein. In some embodiments, the nucleic acid amplification region may include a thermal cycler. In some embodiments, the system includes a detection region, which detects the presence or absence of reaction products from the nucleic acid amplification region, and which may be fluidically connected to the nucleic acid amplification region. In some embodiments, the system includes means for adding a first reagent to a monodisperse single-emulsion droplet, and/or a heating element. In some embodiments, the system includes a sorting region or a combination detection/sorting region fluidically connected to the nucleic acid amplification region. In some embodiments, alternatively or in addition to an "on-chip" sorting region, sorting of the monodisperse droplets may occur "off-chip". For example, in the case of aqueous phase-in immiscible phase-in aqueous phase double emulsions, an off chip flow cytometry device, e.g., a FACS device or MACS device, may be utilized for sorting.

BRIEF DESCRIPTION OF THE DRAWINGS

The invention may be best understood from the following detailed description when read in conjunction with the accompanying drawings. Included in the drawings are the following figures:

FIG. 2 is a schematic showing a PTE monodisperse droplet generation workflow according to an embodiment of the present disclosure. Panel A depicts combining a plurality of monodisperse template particles with a first fluid containing target particles to provide a first mixture. Panel B depicts combining the first mixture with a second fluid to provide a second mixture, wherein the second fluid is immiscible with the first fluid. Panel C depicts shearing the second mixture such that the monodisperse template particles are encapsulated in monodisperse droplets in the second fluid, thereby providing monodisperse droplets including the first fluid, one of the monodisperse template particles, and one of the target particles.

FIG. 3 is a schematic showing an embodiment of the PTE workflow depicted in FIG. 2. Panel A depicts adding monodisperse polyacrylamide (PAA) beads to PCR reaction mix. Panel B depicts capturing PCR reagents in the PAA beads. Panel C depicts removing excess aqueous solution. Panel D depicts adding oil with stabilizing surfactant, and Panel E depicts generating emulsions by vortexing. Panel F depicts amplifying one of a plurality of nucleic acid target particles inside monodisperse droplets and the detection of a fluorescent signal related to the amplification product.

FIG. 9 provides a graph showing results with microfluidic ddPCR for comparison. The average template copy number per droplet was estimated by assuming a Poisson distribution scales with the controlled template concentrations over the tested three-decade range ($R^2$=0.9993 and the error bar depicted standard error).

FIG. 10A depicts a schematic showing the generation of droplets useful for PTE-based ddPCR using quasi-monodisperse commercial particles. FIG. 10B, Panel A depicts fluorescence images after PCR amplification of yeast genomic DNA at different concentrations (A.U.=0, 0.1, 1). FIG. 10B, Panel B depicts a scatter plot showing the size and fluorescence distribution from a sample in the dilution series. Fluorescence-positives and negatives are clearly distinguishable from each other, enabling quantitation by image analysis. FIG. 10B, Panel C depicts Poisson estimator values obtained by using multiple Poisson distributions weighted by droplet volumes, showing a linear correlation with the template concentration ($R^2$=0.9409 and error bars depict standard deviation).

FIGS. 14A-C provides a schematic diagram of a method to perform high throughput scRNA-seq through PTE. FIG. 14A A depicts Drop-seq beads being encapsulated into hydrogels. Cells, proteinase K and hybridization buffer are mixed. FIG. 14B depicts vortexing the mixture for emulsification. FIG. 14C depicts recovering the Drop-seq beads and RT sequencing, followed by data analysis, wherein sequence Read1 has SEQ ID NO.: 1.

DETAILED DESCRIPTION

Figure 1:
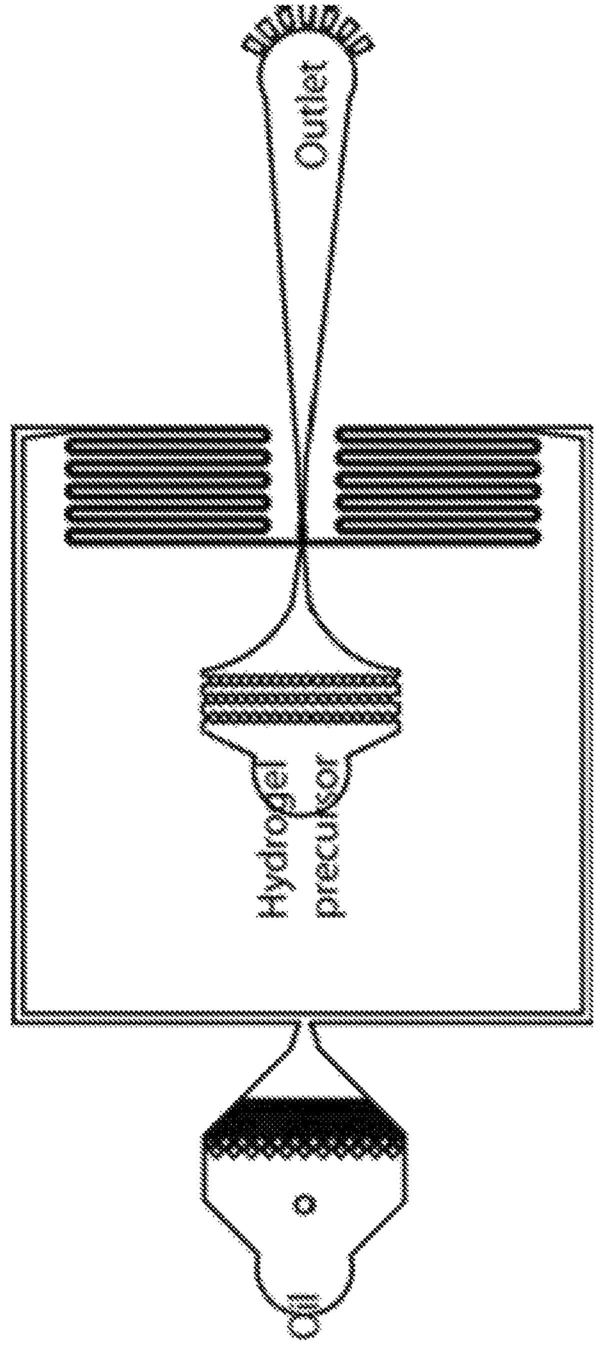
FIG. 1 shows a design of a microfluidic device used to generate particles for PTE.

The present disclosure provides an improved particle-templated emulsification (PTE) method for generating monodisperse emulsions. The droplets present in such emulsions are referred to interchangeably herein as PTE droplets and PIPs. The disclosed methods facilitate the encapsulation and subsequent analysis of target particles of interest without requiring the use of a microfluidic device. The disclosed methods involve the use of monodisperse particles to template the formation of monodisperse droplets.

The disclosed methods facilitate the encapsulation of target particles, e.g., nucleic acids, which can then be detected, quantitated and/or sorted, e.g., based on their sequence as detected with nucleic acid amplification techniques, e.g., PCR and/or MDA.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a droplet" includes a plurality of such droplets and reference to "the nucleic acid" includes reference to one or more nucleic acids and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. For example, described herein are a variety of additional methods and applications, which may be performed in connection with the methods described herein relating to the generation of a monodisperse emulsion or which may utilized monodisperse droplets prepared according to the methods described herein for the generation of a monodisperse emulsion. In this regard it is considered that any of the non-limiting aspects of the disclosure numbered 1-62 herein may be modified as appropriate with one or more steps of such methods and applications, and/or that such methods and applications may utilize monodisperse droplets prepared according to one or more of the non-limiting aspects of the disclosure numbered 1-62 herein. Such methods and applications include, without limitation, those described in the sections herein, entitled: Methods; Monodisperse Template Particles and Generation Thereof; Monodisperse Droplets, Including Single-Emulsion Droplets and Multiple-Emulsion Droplets, and Generation Thereof; Giant Unilamellar Vesicles (GUVs); Fluids Involved in the Generation of Monodisperse Emulsions; Surfactants; Shearing; Adding Reagents to Single-Emulsion Droplets, Multiple-Emulsion Droplets and/or GUVs; Tethering Moieties; Reactions in Single-Emulsion Droplets, Multiple-Emulsion Droplets, and/or GUVs; Detecting PCR Products; Detecting Cells (e.g., Tumor Cells) in Single-Emulsion Droplets, Multiple-Emulsion Droplets, and/or GUVs; Nucleic Acid Detection in Single-Emulsion Droplets, Multiple-Emulsion Droplets, and/or GUVs; Multiple Displacement Amplification; PCR; Double PCR; Digital PCR; RNA sequencing (RNAseq); Measuring Lengths of Nucleic Acids; Microfluidic Enrichment for Sequence Analysis (MESA) in Single-Emulsion Droplets, Multiple-Emulsion Droplets, and/or GUVs; PCR Activated Cell Sorting (PACS) in Single-Emulsion Droplets, Multiple-Emulsion Droplets, and/or GUVs; Live-cell PCR Activated Cell Sorting (PACS); Mass Spectrometry Activated Cell Sorting (MS-ACS); Colony Growth and Lysis; Multiplexing; Digital Enzyme-linked Immunosorbent Assay (ELISA); Digital Oligo-linked Immunosorbent Assay (dOLISA); Sorting; Suitable Subjects and/or Samples; Detecting Proteins or DNA with Enzyme-Linked Probes; and Detecting Cancer.

Methods

As summarized above, the present disclosure provides an improved PTE method for generating monodisperse emulsions. The disclosed methods facilitate the encapsulation and optionally the subsequent analysis of target particles of interest without requiring the use of a microfluidic device. In particular, the disclosed methods involve the production of monodisperse target particle-containing droplets without the need for advanced microfluidic systems. While microfluidic systems may be utilized in connection with monodisperse droplets prepared as described herein, e.g., for the addition of reagents to droplets or for the sorting of droplets, such systems are not required for production of the monodisperse droplets themselves. The disclosed methods involve the use of monodisperse particles to template the formation of monodisperse droplets via application of a shear force, which may be applied, e.g., using a homogenizer (e.g., vortex mixer), passing a suitable mixture through a pipette tip, shaking a suitable mixture using a bead beater, or any other suitable method.

As used herein, the term "biological sample" encompasses a variety of sample types obtained from a variety of sources, which sample types contain biological material. For example, the term includes biological samples obtained from a mammalian subject, e.g., a human subject, and biological samples obtained from a food, water, or other environmental source, etc. The definition encompasses blood and other liquid samples of biological origin, as well as solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, cells, serum, plasma, biological fluid, and tissue samples. "Biological sample" includes cells, e.g., bacterial cells or eukaryotic cells; biological fluids such as blood, cerebrospinal fluid, semen, saliva, and the like; bile; bone marrow; skin (e.g., skin biopsy); and antibodies obtained from an individual.

As described more fully herein, in various aspects the subject methods may be used to detect a variety of components from such biological samples. Components of interest include, but are not necessarily limited to, cells (e.g., circulating cells and/or circulating tumor cells), viruses, polynucleotides (e.g., DNA and/or RNA), polypeptides (e.g., peptides and/or proteins), and many other components that may be present in a biological sample.

"Polynucleotides" or "oligonucleotides" as used herein refer to linear polymers of nucleotide monomers, and may be used interchangeably. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999).

The terms "polypeptide," "peptide," and "protein," used interchangeably herein, refer to a polymeric form of amino acids of any length. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.,* 243 (1969), 3552-3559 is used.

In certain aspects, methods are provided for counting and/or genotyping cells, including normal cells or tumor cells, such as CTCs. A feature of such methods is the use of microfluidics.

The methods as described herein generally involve generating a plurality of monodisperse droplets including monodisperse single-emulsion droplets or multiple-emulsion droplets and/or GUVs, which may be followed by, e.g., one or more nucleic acid synthesis steps, and/or one or more detection and/or sorting steps. FIG. 2 presents a schematic showing a PTE workflow according to an embodiment of the present disclosure. Panel A depicts a first step of combining a plurality of monodisperse template particles with a first fluid containing target particles to provide a first mixture. Panel B depicts a second step of combining the first mixture with a second fluid to provide a second mixture, wherein the second fluid is immiscible with the first fluid. Panel C depicts a step of shearing the second mixture such that the monodisperse template particles are encapsulated in monodisperse droplets in the second fluid. As a result of these steps monodisperse droplets including the first fluid, one of the monodisperse template particles, and one of the target particles are provided.

Following the generation of the monodisperse droplets, such droplets may be subject to any of a variety of suitable work-flows, techniques and/or reactions as described herein or as otherwise known in the art in connection with droplet-based analysis of target particles such as cells, virus, and components thereof, such as nucleic acids, e.g., DNA and RNA. Additional droplet-based analysis methods, which may be used in connection with monodisperse droplets prepared according to the methods as described herein, may be found for example in the following publications, which are incorporated by reference herein: U.S. Patent Application Publication No. 2015/0232942, U.S. Patent Application Publication No. 2017/0121756, U.S. Patent Application Publication No. 2017/0022538, and U.S. Patent Application Publication No. 2017/0009274.

FIG. 3 presents a schematic showing a more detailed embodiment of the PTE workflow shown in FIG. 2. Panel A depicts a step of adding monodisperse polyacrylamide (PAA) beads to PCR reaction mix, which may include, e.g., template nucleic acids, primers, probes, dNTPs, and a suitable enzyme (e.g., Taq polymerase) to provide a first mixture. Panel B depicts a step of capturing PCR reagents in the PAA beads by soaking the PAA beads in the PCR reaction mix. Panel C depicts a step of removing excess aqueous solution from the first mixture after soaking the PAA beads in the PCR reaction mix. Panel D depicts a step of adding oil (a second fluid which is immiscible with the PCR reaction mix) with a stabilizing surfactant to provide a second mixture. Panel E depicts a step of generating monodisperse emulsions by vortexing the second mixture. Panel F depicts a step of amplifying one of a plurality of nucleic acid target particles inside the monodisperse droplets and the detection of a fluorescent signal related to the amplification product.

A feature of certain methods as described herein is the use of a polymerase chain reaction (PCR)-based assay to detect the presence of certain oligonucleotides and/or genes, e.g., oncogene(s) present in cells. Examples of PCR-based assays of interest include, but are not limited to, quantitative PCR (qPCR), quantitative fluorescent PCR (QF-PCR), multiplex fluorescent PCR (MF-PCR), digital droplet PCR (ddPCR) single cell PCR, PCR-RFLP/real time-PCR-RFLP, hot start PCR, nested PCR, in situ polony PCR, in situ rolling circle amplification (RCA), bridge PCR, picotiter PCR, emulsion PCR and reverse transcriptase PCR (RT-PCR). Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA).

A PCR-based assay may be used to detect the presence of certain gene(s), such as certain oncogene(s). In such assays, one or more primers specific to each gene of interest are reacted with the genome of each cell. These primers have sequences specific to the particular gene, so that they will only hybridize and initiate PCR when they are complementary to the genome of the cell. If the gene of interest is present and the primer is a match, many copies of the gene are created. To determine whether a particular gene is present, the PCR products may be detected through an assay probing the liquid of the monodisperse droplet, such as by staining the solution with an intercalating dye, like SybrGreen or ethidium bromide, hybridizing the PCR products to a solid substrate, such as a bead (e.g., magnetic or fluorescent beads, such as Luminex beads), or detecting them through an intermolecular reaction, such as FRET. These dyes, beads, and the like are each examples of a “detection component,” a term that is used broadly and generically herein to refer to any component that is used to detect the presence or absence of nucleic acid amplification products, e.g., PCR products.

A number of variations of these basic approaches will now be outlined in greater detail below.

Monodisperse Template Particles and Generation Thereof

As used herein, the term “monodisperse,” as applied to template particles, refers to a variation in diameter or largest dimension of the template particles such that at least 50% or more, e.g., 60% or more, 70% or more, 80% or more, 90% or more, 95% or more, or 99% or more of the template particles vary in diameter or largest dimension by less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01.

As used herein, the term “template particles” and “template particle” are used interchangeably to refer to tiny, generally spherical, particles. Template particles may be porous or nonporous. In any suitable embodiment herein, template particles may include microcompartments, which may contain additional components and/or reagents, e.g., additional components and/or reagents that may be releasable into monodisperse droplets as described herein. In any suitable embodiment herein, template particles may include a polymer, e.g., a hydrogel. In some embodiments, e.g., embodiments as described herein in which the first fluid is an aqueous fluid, the polymer is a hydrophilic polymer. In some embodiments, e.g., embodiments as described herein in which the first fluid is a non-aqueous fluid, e.g., an oil, the polymer is a lipophilic polymer. Template particles generally range from about 0.1 to about 1000 μm in diameter or largest dimension. In some embodiments, template particles have a diameter or largest dimension of about 1.0 μm to 1000 μm, inclusive, such as 1.0 μm to 750 μm, 1.0 μm to 500 μm, 1.0 μm to 250 μm, 1.0 μm to 200 μm, 1.0 μm to 150 μm 1.0 μm to 100 μm, 1.0 μm to 10 μm, or 1.0 μm to 5 μm, inclusive. In some embodiments, template particles have a diameter or largest dimension of about 10 μm to about 200 μm, e.g., about 10 μm to about 150 μm, about 10 μm to about 125 μm, or about 10 μm to about 100 μm.

In practicing the methods as described herein, the composition and nature of the monodisperse template particles may vary. For instance, in certain aspects, the monodisperse template particles may be microgel particles that are micron-scale spheres of gel matrix. In some embodiments, the microgels are composed of a hydrophilic polymer that is soluble in water, including alginate or agarose. In other embodiments, the microgels are composed of a lipophilic microgel.

In other aspects, the monodisperse template particles may be a hydrogel. In certain embodiments, the hydrogel is selected from naturally derived materials, synthetically derived materials and combinations thereof. Examples of hydrogels include, but are not limited to, collagen, hyaluronan, chitosan, fibrin, gelatin, alginate, agarose, chondroitin sulfate, polyacrylamide, polyethylene glycol (PEG), polyvinyl alcohol (PVA), polyacrylamide/poly(acrylic acid) (PAA), hydroxyethyl methacrylate (HEMA), poly N-isopropylacrylamide (NIPAM), and polyanhydrides, poly(propylene fumarate) (PPF).

In some embodiments, the monodisperse template particles have an average volume, and a method as described herein includes shrinking the monodisperse template particles to decrease the average volume. The shrinking may occur upon the application of an external stimulus, e.g., heat. For instance, the monodisperse template particles may be encapsulated in a fluid by shearing, followed by the application of heat, causing the monodisperse template particles to shrink in size. The monodisperse single-emulsion droplet or double-emulsion droplet or GUV will not shrink because the droplet volume is constant and dictated by the original size of the monodisperse template particle, but the monodisperse template particle within the droplet will shrink away from the surface of the droplet.

In any suitable embodiment herein, the monodisperse template particles may include at least one of cells, genes, drug molecules, therapeutic agents, particles, bioactive agents, osteogenic agents, osteoconductive agents, osteoinductive agents, anti-inflammatory agents, growth factors, fibroin derived polypeptide particles, nucleic acid synthesis reagents, nucleic acid detection reagents, target particles, DNA molecules, RNA molecules, genomic DNA molecules, and combinations of the same. In embodiments that involve the combination of multiple reagents within a monodisperse single-emulsion droplet or double-emulsion droplet or GUV, the monodisperse template particles may contain multiple compartments. The monodisperse template particles may be used to encapsulate reagents that can be triggered to release a desired compound, e.g., a substrate for an enzymatic reaction. For instance, a double emulsion droplet can be encapsulated in the monodisperse template particles that are triggered to rupture upon the application of a stimulus, e.g., heat. The stimulus initiates a reaction after the monodisperse template particles have been encapsulated in an immiscible carrier phase fluid.

Monodisperse template particles may be generated under microfluidic control, e.g., using methods described in U.S. Patent Application Publication No. 2015/0232942, the disclosure of which is incorporated by reference herein. Microfluidic devices can form emulsions consisting of droplets that are extremely uniform in size. The monodisperse template particles generation process may be accomplished by pumping two immiscible fluids, such as oil and water, into a junction. The junction shape, fluid properties (viscosity, interfacial tension, etc.), and flow rates influence the properties of the monodisperse template particles generated but, for a relatively wide range of properties, monodisperse template particles of controlled, uniform size can be generated using methods like T-junctions and flow focusing. To vary monodisperse template particle size, the flow rates of the immiscible liquids may be varied since, for T-junction and flow focus methodologies over a certain range of properties, monodisperse template particle size depends on total flow rate and the ratio of the two fluid flow rates. To generate a monodisperse template particle with microfluidic methods, the two fluids are normally loaded into two inlet reservoirs (e.g., syringes, pressure tubes) and then pressurized as needed to generate the desired flow rates (e.g., using syringe pumps, pressure regulators, gravity, etc.). This pumps the fluids through the device at the desired flow rates, thus generating droplet of the desired size and rate.

In some embodiments, monodisperse template particles may be generated using parallel droplet generation techniques, including, but not limited to, serial splitting and distribution plates. Parallel droplet generation techniques of interest further include those described by Abate and Weitz, *Lab Chip* 2011, June 7; 11(11):1911-5; and Huang et al., *RSC Advances* 2017, 7, 14932-14938; the disclosure of each of which is incorporated by reference herein.

In some embodiments, the monodisperse template particles are allowed to solidify by triggering a gelation mechanism, including, but not limited to, the polymerization or crosslinking of a gel matrix. For instance, polyacrylamide gels are formed by copolymerization of acrylamide and bis-acrylamide. The reaction is a vinyl addition polymerization initiated by a free radical-generating system. In certain aspects, agarose hydrogels undergo gelation by cooling the hydrogels below the gelation temperature.

In some embodiments, the monodisperse template particles may be removed from the fluid, dried, and stored in a stable form for a period of time. Examples of drying approaches include, but are not limited to, heating, drying under vacuum, freeze drying, and supercritical drying. In some embodiments, the dried monodisperse template particles may be combined with a fluid, but still retain the shape and structure as independent, often spherical, gel particles. In some embodiments, the dried monodisperse template particles are combined with an appropriate fluid, causing a portion of the fluid to be absorbed by the monodisperse template particles. In some embodiments, the porosity of the monodisperse template particles may vary, to allow at least one of a plurality of target particles to be absorbed into the monodisperse template particles when combined with the appropriate fluid. Any convenient fluid that allows for the desired absorption to be performed in the monodisperse template particles may be used.

As used herein, the terms "absorb," "swell," and "expand" as applied to monodisperse template particles may be used interchangeably to refer to the process in which a fluid permeates a substance, or in which a substance incorporates a fluid. In some embodiments, the substance being absorbed may retain at least a portion of its shape and structure. In some embodiments, the substance being absorbed may become incorporated into a fluid so as to form a solution.

In certain aspects, a surfactant may be used to stabilize the monodisperse template particles. Accordingly, a monodisperse template particle may involve a surfactant stabilized emulsion, e.g., a surfactant stabilized single emulsion or a surfactant stabilized double emulsion. Any convenient surfactant that allows for the desired reactions to be performed in the monodisperse template particles may be used. In other aspects, a monodisperse template particle is not stabilized by surfactants or particles.

Monodisperse Droplets, Including Single-Emulsion Droplets and Multiple-Emulsion Droplets, and Generation Thereof As used herein, the term "monodisperse," as applied to droplets, e.g., monodisperse single-emulsion droplets, refers to a variation in diameter or largest dimension of droplets produced by shearing in the presence of monodisperse template particles, which is less than would occur when droplets are produced by shearing under the same conditions in the absence of the monodisperse template particles. Generally, monodisperse single-emulsion droplets or multiple-emulsion droplets can have more variation in diameter or largest dimension as compared to the monodisperse template particles from which they are generated, while still functioning in the various methods described herein. Monodisperse droplets generally range from about 0.1 to about 1000 μm in diameter or largest dimension, and may have a variation in diameter or largest dimension of less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01, in diameter or the largest dimension. In some embodiments, monodisperse droplets have a variation in diameter or largest dimension such that at least 50% or more, e.g., 60% or more, 70% or more, 80% or more, 90% or more, 95% or more, or 99% or more of the monodisperse droplets, vary in diameter or largest dimension by less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01. In some embodiments, monodisperse droplets have a diameter of about 1.0 μm to 1000 μm, inclusive, such as about 1.0 μm to about 750 μm, about 1.0 μm to about 500 μm, about 1.0 μm to about 250 μm, about 1.0 μm to about 200 μm, about 1.0 μm to about 150 μm, about 1.0 μm to about 100 μm, about 1.0 μm to about 10 μm, or about 1.0 μm to about 5 μm, inclusive. In some embodiments, the internal volume of the monodisperse droplets may be about 0.01 pL or less, about 0.1 pL or less, 1 pL or less, about 5 pL or less, 10 pL or less, 100 pL or less, or 1000 pL or less. In some embodiments, the internal volume of the monodisperse droplets may be about 1 fL or less, about 10 fL or less, or 100 fL or less. In some embodiments, the internal volume of the monodisperse droplets may encompass a liquid volume which ranges between picoliters and femotliters (e.g., about 0.001 pL to about 1000 pL). In some embodiments, the internal volume of the monodisperse droplets extends strictly below the nanoliter level (e.g., strictly picoliter, strictly femtoliter, or combination thereof).

In practicing the methods as described herein, the composition and nature of the monodisperse droplets, e.g., single-emulsion and multiple-emulsion droplets, may vary. For instance, in certain aspects, a surfactant may be used to stabilize the droplets. Accordingly, a droplet may involve a surfactant stabilized emulsion, e.g., a surfactant stabilized single emulsion or a surfactant stabilized double emulsion. Any convenient surfactant that allows for the desired reactions to be performed in the droplets may be used. In other aspects, monodisperse droplets are not stabilized by surfactants.

The droplets described herein may be prepared as emulsions, e.g., as an aqueous phase fluid dispersed in an immiscible phase carrier fluid (e.g., a fluorocarbon oil or a hydrocarbon oil) or vice versa. In particular, multiple-emulsion droplets as described herein may be provided as double-emulsions, e.g., as an aqueous phase fluid in an immiscible phase fluid, dispersed in an aqueous phase carrier fluid; quadruple emulsions, e.g., an aqueous phase fluid in an immiscible phase fluid, in an aqueous phase fluid, in an immiscible phase fluid, dispersed in an aqueous phase carrier fluid; and so on. Generating a monodisperse single-emulsion droplet or a multiple-emulsion droplet as described herein may be performed without microfluidic control. In alternative embodiments, a monodisperse single-emulsion may be prepared without the use of a microfluidic device, but then modified using a microfluidic device to provide a multiple emulsion, e.g., a double emulsion.

Monodisperse single emulsions may be generated without the use of microfluidic devices using the methods described herein. Producing a monodisperse emulsion using monodisperse template particles can provide emulsions including droplets that are extremely uniform in size. The droplet generation process may be accomplished by combining a plurality of monodisperse template particles with a first fluid to provide a first mixture, wherein the first fluid includes a plurality of target particles; combining the first mixture with a second fluid to provide a second mixture, wherein the second fluid is immiscible with the first fluid; and shearing the second mixture such that a plurality of the monodisperse template particles are encapsulated in a plurality of monodisperse droplets in the second fluid, thereby providing a plurality of monodisperse droplets including the first fluid, one of the monodisperse template particles, and one of the plurality of target particles. To vary droplet size, the shearing rate and monodisperse template particle sizes may be varied. For agarose gels, the monodisperse template particles can be liquefied using an external stimulus (e.g., heat) to generate a liquid monodisperse emulsion.

The percentage of monodisperse droplets, e.g., monodisperse single-emulsion droplets or multiple-emulsion droplets, with one, and not more than one, monodisperse template particle may be about 70% or more; about 75% or more; about 80% or more; about 85% or more; about 90% or more; or about 95% or more. For example, the percentage of monodisperse droplets with one, and not more than one, monodisperse template particle may be from about 70% to about 100%, e.g., from about 75% to about 100%, from about 80% to about 100%, from about 85% to about 100%, from about 90% to about 100%, or from about 95% to about 100%. As a further example, the percentage of monodisperse droplets with one, and not more than one, monodisperse template particle may be from about 70% to about 95%, e.g., from about 75% to about 90%, or from about 80% to about 85%. The percentage of monodisperse template particles that are encapsulated in monodisperse droplets in the second fluid may be about 70% or more; about 75% or; about 80% or more; about 85% or more; or about 90% or more. For example, the percentage of monodisperse template particles that are encapsulated in monodisperse droplets in the second fluid may be from about 70% to about 100%, e.g., from about 75% to about 100%, from about 80% to about 100%, from about 85% to about 100%, from about 90% to about 100%, or from about 95% to about 100%. As a further example, the percentage of monodisperse template particles that are encapsulated in monodisperse droplets in the second fluid may be from about 70% to about 95%, e.g., from about 75% to about 90%, or from about 80% to about 85%.

Double emulsions may also be generated without the use of microfluidic devices using the methods described herein. A double emulsion includes droplets contained within droplets, e.g., an aqueous phase fluid surrounded by an immiscible phase shell in an aqueous phase carrier fluid (e.g., water-in oil-in water) or a immiscible phase fluid surrounded by an aqueous phase shell in an immiscible phase carrier fluid (e.g., oil-in water-in oil). The second mixture described herein, which includes monodisperse single-emulsion droplets in the second fluid, is combined with a third fluid to produce a third mixture, wherein the third fluid is immiscible with at least the second fluid. The third mixture is then sheared to encapsulate the monodisperse template particles in double-emulsion droplets in the third fluid. The third fluid may be immiscible with both the first and second fluids. A particularly useful kind of double emulsion includes an aqueous droplet encapsulated within a slightly larger oil droplet, itself dispersed in a carrier aqueous phase. Double emulsions are valuable because the inner "core" of the structure can be used to provide active compounds, like dissolved solutes or biological materials, where they are shielded from the external environment by the surrounding oil shell. A benefit of generating double emulsions using monodisperse template particles is similar to that for the generation of single emulsions, in that the double emulsion dimensions (inner and outer droplet sizes) can be controlled over a wide range and the droplets can be formed with a high degree of uniformity. As discussed herein, in suitable embodiments the monodisperse template particles can be dissolved and/or melted within the monodisperse droplets. Accordingly, in some embodiments multiple emulsions, e.g., double emulsions, may be prepared from monodisperse droplets which no longer contain an intact template particle yet retain their original size. In this manner, such monodisperse droplets may serve as templates for the preparation of multiple emulsions, e.g., double emulsions.

Encapsulation in droplets of sample materials and/or reagents, e.g., nucleic acids and/or nucleic acid synthesis reagents (e.g., isothermal nucleic acid amplification reagents and/or nucleic acid amplification reagents), can be achieved via a number of methods, including microfluidic and non-microfluidic methods. In the context of microfluidic methods, there are a number of techniques that can be applied, including glass microcapillary double emulsification or double emulsification using sequential droplet generation in wettability patterned devices. Microcapillary techniques form droplets by generating coaxial jets of the immiscible phases that are induced to break into droplets via coaxial flow focusing through a nozzle. However, a potential disadvantage of this approach is that the devices are generally fabricated from microcapillary tubes that are aligned and glued together. Since the drop formation nozzle is on the scale of tens of microns, even small inaccuracies in the alignment of the capillaries can lead to a device failure. By contrast, sequential drop formation in spatially patterned droplet generation junctions can be achieved in devices fabricated lithographically, making them simpler to build and to create in large numbers while maintaining uniformity over dimensions. However, in some cases the planar nature of these devices may not be ideal for generating double emulsions, since the separate phases all enter the device while in contact with the channel walls, necessitating that wettability be carefully patterned to enable engulfment of the appropriate phases at the appropriate locations. This may make the devices more difficult to fabricate, and in some cases, may prevent emulsification of liquids whose wetting properties are not optimized for the device. Accordingly, in some aspects the present disclosure provides methods for generating a monodisperse emulsion which encapsulates sample materials and/or reagents, e.g., nucleic acids and/or nucleic acid synthesis reagents (e.g., isothermal nucleic acid amplification reagents and/or nucleic acid amplification reagents) without the use of a microfluidic device.

For example, the methods as described herein may include combining a plurality of monodisperse template particles with a first fluid to provide a first mixture, wherein the first fluid includes a plurality of target particles, e.g., nucleic acids, etc. In some embodiments, the combining the plurality of monodisperse template particles with the first fluid to provide the first mixture includes causing a portion of the first fluid, and the target particles and/or reagents contained therein, to be absorbed by the monodisperse template particles. In some embodiments, combining the plurality of monodisperse template particles with the first fluid to provide the first mixture includes flowing a portion of the first fluid into the monodisperse template particles. In some embodiments, combining the plurality of monodisperse template particles with the first fluid to provide the first mixture includes diffusing a portion of the first fluid into the monodisperse template particles. In some embodiments, the combining the plurality of monodisperse template particles with the first fluid to provide the first mixture includes swelling the monodisperse template particles with a portion of the first fluid.

In some embodiments, excess first fluid is removed from the first mixture after causing the portion of the first fluid to be absorbed by the monodisperse template particles. The amount of excess first fluid removed may vary. For example, by removing most of the excess fluid, target particles that cannot flow into the monodisperse template particles can be encapsulated by causing target particles, e.g., cells, to be physically close to at least one of a plurality of monodisperse template particles. Combining this mixture with a second fluid which is immiscible with the first fluid provides a second mixture. By shearing this second mixture, a plurality of the monodisperse template particles may be encapsulated in a plurality of monodisperse droplets in the second fluid, thereby providing a plurality of monodisperse droplets including the first fluid, one of the monodisperse template particles, and one of the plurality of target particles that cannot flow into the monodisperse template particles.

In some embodiments, the target molecules are cells. In such embodiments, the monodisperse droplets may contain one or more cells per droplet. Alternatively, the monodisperse droplets do not contain more than one cell per droplet. In some embodiments, after shearing, some droplets in the emulsion do not contain any of the plurality of target particles.

In some embodiments, the methods disclosed herein include combining the first mixture, including a plurality of monodisperse template particles and a first fluid including a plurality of target particles, with a second fluid to provide a second mixture, wherein the second fluid is immiscible with the first fluid; and shearing the second mixture such that a plurality of the monodisperse template particles are encapsulated in a plurality of monodisperse droplets in the second fluid, thereby providing a plurality of monodisperse droplets including the first fluid, one of the monodisperse template particles, and one of the plurality of target particles. In some embodiments, after shearing, the second fluid includes a plurality of droplets that do not contain one of the monodisperse template particles. The droplets that do not contain one of the monodisperse template particles may be removed from the monodisperse emulsion by a suitable separation technique, such as filtration or centrifugation. Those droplets that do not contain one of the monodisperse template particles may be smaller in diameter than those droplets that do contain one of the monodisperse template particles. The monodisperse droplets containing monodisperse template particles may also be enriched relative to droplets that do not contain one of the monodisperse template particles.

As used herein, the terms “enriched” and “enrichment” may be used interchangeably to refer to the process of increasing the ratio of target entities (e.g., monodisperse droplets containing monodisperse template particles) to non-target entities (e.g., monodisperse droplets not containing monodisperse template particles) in the monodisperse emulsion compared to the ratio in the original monodisperse emulsion. Using the method disclosed herein, monodisperse droplets containing monodisperse template particles may be enriched relative to droplets that do not contain one of the monodisperse template particles, e.g., at least 2 fold, at least 3 fold, at least 5 fold, at least 10 fold, at least 20 fold, at least 30 fold, at least 40 fold, at least 50 fold, at least 100 fold, or more.

In some embodiments, excess second fluid is removed from the second mixture including a plurality of monodisperse template particles encapsulated in a plurality of monodisperse droplets after shearing. The excess second fluid can be removed using any suitable method, e.g., by centrifugation and removing the supernatant.

In the context of multiple emulsions, e.g., double emulsions, generated as described herein, additional manipulations can be performed on them to modify their properties. For example, in many double emulsion formulations, the shells of the double emulsions are permeable to certain molecules, allowing these molecules to be passively diffused into or out of the double emulsions. This can be used for example, to modulate the environment in the double emulsions. Similarly, the inner droplets of the double emulsions can be shrunk or grown by, for example, allowing a solvent to diffuse into or out of them. For example, by dispersing double emulsions in a buffer including a high concentration of salt, aqueous phase fluid can be induced to diffuse out of the double emulsions until the osmolalities on the inner droplet and outside carrier phase are matched, at which point the droplet size will remain constant. This can be used to change the size of the inner droplet or, alternatively to concentrate or dilute reagents contained within the double emulsion by adding or removing excess solvent.

The shells of the double emulsions can also be modified using techniques such as solvent extraction to, for example, in the case of a water-in-oil-in water double emulsion, remove excess hydrophobic phase from the shell. This can induce other changes in double emulsions such as, for example, their transition into lipid vesicles, polymersomes, or colloidosomes via dewetting or other phenomena. Air bubbles may also be introduced into the double emulsions, for example, in the inner droplet or in the middle, encapsulating phase. The ability to expand and compress air can also be exploited, if desired, to, for example, increase or reduce the size of the double emulsion or the thickness of the double emulsion shell, in some embodiments. Air bubbles in the middle phase can, for example, be expanded by reducing the pressure of the system, which will exert forces on the inner droplet that, for instance, can be used to induce a transition into another structure, such as a polymersome or vesicle. Gelling agents can also be added to allow the outer layers of the droplets to solidify. Examples of gelling agents include, but are not limited to, gelatin, agar, xanthan gum, gellan gum, carrageenan, isubgol, and guar gum.

Giant Unilamellar Vesicles (GUVs)

Double emulsions generally refer to emulsions within emulsions—i.e., liquid droplets that are contained within liquid droplets of a second immiscible phase. They can be stabilized by surfactant but, importantly, the middle phase "shell" includes a liquid phase in addition to the optional surfactant. As the volume of the shell is reduced, double emulsions resemble less droplets-within-droplets than vesicle-like structures, with a core fluid encapsulated in a thin membrane of surfactant molecules. Double emulsions can be used to form such "vesicles" by allowing them to undergo a de-wetting transition, in which the middle liquid phase fluid is expunged from the shell but a surfactant layer is maintained, generating a vesicle including the aqueous core with a thin layer of surfactant molecules surrounding it, and a small oil droplet that was originally the shell adhering to it. Such vesicles are also referred to herein as liposomes.

The tendency of a double emulsion to de-wet depends on the properties of the different solutions and surfactants, especially the interfacial tensions of the different phases with respect to one another. An aqueous formulation including fluorinated oil, PEG-Krytox® surfactant, Jeffamine® (polyetheramine)-Krytox® surfactant, and pluronic, when added to the carrier phase, appears capable of forming double emulsions and vesicles, both of which are thermostable to above 95° C. Krytox® fluids are fluorinated synthetic oils based on hexfluoropropylene oxide combined with a functional end-group. Other surfactants such as Tween® 20 (Polysorbate 20) and Span® 80 (Sorbitane monooleate) may be utilized with or without thickening agents such as PEG, alginate, glycerol, etc., to induce GUV formation from double emulsions.

Fluids Involved in the Generation of Monodisperse Emulsions

As discussed herein, the disclosed methods generally involve combining a plurality of monodisperse template particles with a first fluid to provide a first mixture, wherein the first fluid includes a plurality of target particles; combining the first mixture with a second fluid to provide a second mixture, wherein the second fluid is immiscible with the first fluid; and shearing the second mixture such that a plurality of the monodisperse template particles are encapsulated in a plurality of monodisperse droplets in the second fluid, thereby providing a plurality of monodisperse droplets including the first fluid, one of the monodisperse template particles, and one of the plurality of target particles. In some embodiments, the methods include the further step of combining a third fluid with the second mixture, following the shearing of the second mixture, to produce a third mixture, wherein the third fluid is immiscible with the second fluid.

The first fluid is generally selected to be immiscible with the second fluid and share a common hydrophilicity/hydrophobicity with the material which constitutes the monodisperse template particles. The third fluid is generally selected to be immiscible with the second fluid, and may be miscible or immiscible with the first fluid. Accordingly, in some embodiments, the first fluid is an aqueous phase fluid; the second fluid is a fluid which is immiscible with the first fluid, such as a non-aqueous phase, e.g., a fluorocarbon oil, a hydrocarbon oil, or a combination thereof; and the third fluid is an aqueous phase fluid. Alternatively, is some embodiments the first fluid is a non-aqueous phase, e.g., a fluorocarbon oil, a hydrocarbon oil, or a combination thereof; the second fluid is a fluid which is immiscible with the first fluid, e.g., an aqueous phase fluid; and the third fluid is a fluorocarbon oil, a hydrocarbon oil or a combination thereof.

The non-aqueous phase may serve as a carrier fluid forming a continuous phase that is immiscible with water, or the non-aqueous phase may be a dispersed phase. The non-aqueous phase may be referred to as an oil phase including at least one oil, but may include any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others.

In exemplary embodiments, the oil is a fluorinated oil, such as a fluorocarbon oil, which may be a perfluorinated organic solvent. Examples of a suitable fluorocarbon oils include, but are not limited to, $C_9H_5OF_{15}$ (HFE-7500), $C_{21}F_{48}N_2$ (FC-40), and perfluoromethyldecalin (PFMD).

As discussed herein, in some embodiments, the first fluid contains a plurality of target particles (e.g. DNA molecules such as genomic DNA molecules, RNA molecules, nucleic acid synthesis reagents such as nucleic acid amplification reagents including PCR and/or isothermal amplification reagents).

In some embodiments, gelling agents may be added to solidify the outer layers of the droplet.

Surfactants

In certain aspects, a surfactant may be included in the first fluid, second fluid, and/or third fluid. Accordingly, a droplet may involve a surfactant stabilized emulsion, e.g., a surfactant stabilized single emulsion or a surfactant stabilized double emulsion, where the surfactant is soluble in the first fluid, second fluid, and/or third fluid. Any convenient surfactant that allows for the desired reactions to be performed in the droplets may be used, including, but not limited to, octylphenol ethoxylate (Triton X-100), polyethylene glycol (PEG), $C_{26}H_{50}O_{10}$ (Tween 20) and/or octylphenoxypolyethoxyethanol (IGEPAL). In other aspects, a droplet is not stabilized by surfactants.

The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox® FSH). If, however, the oil was switched to a hydrocarbon oil, for example, the surfactant may instead be chosen such that it had a hydrophobic hydrocarbon block, like the surfactant ABIL EM90.

Other surfactants can also be envisioned, including ionic surfactants. Other additives can also be included in the oil to stabilize the droplets, including polymers that increase droplet stability at temperatures above 35° C.

Without intending to be bound by any particular theory, it is proposed that the preparation of a thermostable emulsions relies on the use of a surfactant that is able to form membranes or double emulsion interfaces that can withstand high temperatures, such as those associated with standard PCR reactions. One way to accomplish this may be to use a surfactant with a relatively high molecular weight so that when assembled at the interface of a droplet or in a membrane configuration, the energy required to remove the surfactant from the interface (or break the membrane) is higher than can be provided by kT.

Exemplary surfactants which may be utilized to provide thermostable emulsions are the "biocompatible" surfactants that include PEG-PFPE (polyethyleneglycol-perflouropolyether) block copolymers, e.g., PEG-Krytox® (see, e.g., Holtze et al., "Biocompatible surfactants for water-in-fluorocarbon emulsions," *Lab Chip,* 2008, 8, 1632-1639, the disclosure of which is incorporated by reference herein), and surfactants that include ionic Krytox® in the oil phase and Jeffamine® (polyetheramine) in the aqueous phase (see, e.g., DeJournette et al., "Creating Biocompatible Oil—Water Interfaces without Synthesis: Direct Interactions between Primary Amines and Carboxylated Perfluorocarbon Surfactants", *Anal. Chem.* 2013, 85(21):10556-10564, the disclosure of which is incorporated by reference herein). Additional and/or alternative surfactants may be used provided they form stable interfaces. Many suitable surfactants will thus be block copolymer surfactants (like PEG-Krytox®) that have a high molecular weight. These examples include fluorinated molecules and solvents, but it is likely that non-fluorinated molecules can be utilized as well.

Accordingly, in some embodiments, the present disclosure provides thermostable emulsions. These emulsions are suitable for use in performing biological reactions, such as PCR, RT-PCR, protein-protein interaction studies, etc.

A consideration when forming emulsions, particularly double emulsions, is making them stable so that they remain double emulsions and do not rupture or coalesce. This is often accomplished using stabilizing agents, such as surfactants. However, in some instances, it may be advantageous to create extremely stable double emulsions. In the methods described herein, this can be accomplished, for example, by using a middle phase (enveloping phase) that can be cross linked, such as a polymer gel phase like polydimethylsiloxane. Alternatively, the surfactants themselves can be made to crosslink with one another by, for example, creating a cross linking group. This group can exist on the hydrophobic tail of the surfactant or, alternatively, on the hydrophilic head. It may crosslink the surfactants to each other or, alternatively, crosslinking may be induced by the addition of a reagent from the aqueous phase, such as a molecule that induces polymerization, covalent bond linkage, etc. Biomolecules like antibodies or biotin-streptavidin can also be used to generate surfactant-surfactant crosslinks.

Crosslinking the interface is another way to render the double emulsion shell thermostable. For example, such crosslinking may be achieved by cross-linking the oil phase or by cross-linking the membrane vesicle. As discussed above, one method for crosslinking the interface uses biomolecules, such as streptavidin. For example, the headgroup of a Krytox® polymer may be biotinylated with multiple biotins. Streptavidin is then added to the aqueous phase thereby crosslinking different Krytox® polymers together and generating a cross-linked shell at the water/oil interface. These shells can then be dispersed into water directly or, if desired, encapsulated as double emulsions.

Shearing

To generate a monodisperse emulsion, the disclosed methods include a step of shearing the second mixture provided by combining the first mixture with a second fluid immiscible with the first fluid. Any suitable method or technique may be utilized to apply a sufficient shear force to the second mixture. For example, the second mixture may be sheared by flowing the second mixture through a pipette tip. Other methods include, but are not limited to, shaking the second mixture with a homogenizer (e.g., vortexer), or shaking the second mixture with a bead beater. The application of a sufficient shear force breaks the second mixture into monodisperse droplets that encapsulate one of a plurality of monodisperse template particles. There may also be some droplets that do not contain one of the plurality of monodisperse template particles.

Generally, if the shear is increased, the average droplet size generated will be lower than that of the size of the monodisperse template particles. However, since the monodisperse template particles are in solid form, the droplets containing them will not be any smaller in size, thereby generating a monodisperse emulsion. If the shear rate is substantially higher than the modulus of the monodisperse template particle, then the shear can squeeze liquid out of the monodisperse template particles. Without intending to be bound by any particular theory, it is proposed that a suitable shear rate is one which matches appropriately the modulus of the monodisperse template particles. For example, it may be desirable to select a shear rate/force higher than the Laplace pressure of the droplets of the desired size but less than the modulus of the template particles.

By way of example, and not limitation, where monodisperse PAA, PEG or agarose template particles are utilized with Triton or IGEPAL in the aqueous phase and HFE-7500 fluorinated oil as the non-aqueous phase, vortexing for 30 seconds results in sufficient shear force to generate monodisperse droplets.

Adding Reagents to Single-Emulsion Droplets, Multiple-Emulsion Droplets and/or GUVs In practicing the subject methods, a number of reagents may need to be added to the droplets, in one or more steps (e.g., about 2, about 3, about 4, or about 5 or more steps). The means of adding reagents to the droplets may vary in a number of ways depending for example, on the emulsification stage of the droplets, e.g., different approaches may be applicable to the addition of reagents to monodisperse single-emulsion droplets relative to multiple-emulsion droplets, such as double emulsion droplets. Approaches of interest include, but are not limited to, those described by Ahn, et al., Appl. Phys. Lett. 88, 264105 (2006); Priest, et al., Appl. Phys. Lett. 89, 134101 (2006); Abate, et al., PNAS, Nov. 9, 2010 vol. 107 no. 45 19163-19166; and Song, et al., Anal. Chem., 2006, 78 (14), pp 4839-4849; the disclosures of which are incorporated herein by reference. In some embodiments, reagents may be added to droplets during the emulsification process as described herein, e.g., as components of the first fluid, e.g., without the use of a microfluidic device or system. In other embodiments, microfluidic techniques, devices and/or systems may be utilized to add reagents and/or modify monodisperse droplets once prepared as otherwise described herein.

For instance, a reagent may be added to a monodisperse single-emulsion droplet as described herein by a method involving merging a droplet with a second droplet that contains the reagent(s). The reagent(s) that are contained in the second droplet may be added by any convenient means, specifically including those described herein. This droplet may be merged with the first droplet to create a droplet that includes the contents of both the first droplet and the second droplet. In some embodiments, the first droplet is substantially larger than the second droplet and outnumbers the second droplet.

One or more reagents may also, or instead, be added to monodisperse single-emulsion droplets as described herein using techniques such as droplet coalescence, and/or picoinjection. In droplet coalescence, a target droplet may be flowed alongside a droplet containing the reagent(s) to be added to the target droplet. The two droplets may be flowed such that they are in contact with each other, but not touching other droplets. These droplets may then be passed through electrodes or other means of applying an electrical field, wherein the electric field may destabilize the droplets such that they are merged together.

In picoinjection, a target droplet may be flowed past a channel containing the reagent(s) to be added, wherein the reagent(s) are at an elevated pressure. Due to the presence of the surfactants, however, in the absence of an electric field, the droplet will flow past without being injected, because surfactants coating the droplet may prevent the fluid(s) from entering. However, if an electric field is applied to the droplet as it passes the injector, fluid containing the reagent(s) will be injected into the droplet. The amount of reagent added to the droplet may be controlled by several different parameters, such as by adjusting the injection pressure and the velocity of the flowing drops, by switching the electric field on and off, and the like.

In other aspects, one or more reagents may also, or instead, be added to a monodisperse single-emulsion droplet as described herein by a method that does not rely on merging two droplets together or on injecting liquid into a droplet. Rather, one or more reagents may be added to a droplet by a method involving the steps of emulsifying a reagent into a stream of very small drops, and merging these small drops with a target droplet. Such methods are referred to herein as "reagent addition through multiple-drop coalescence." These methods take advantage of the fact that due to the small size of the drops to be added compared to that of the target droplet, the small drops will flow faster than the target droplets and collect behind them. The collection can then be merged by, for example, applying an electric field. This approach can also, or instead, be used to add multiple reagents to a droplet by using several co-flowing streams of small drops of different fluids. To enable effective merger of the tiny and target droplets, it is important to make the tiny drops smaller than the channel containing the target droplets, and also to make the distance between the channel injecting the target droplets from the electrodes applying the electric field sufficiently long so as to give the tiny drops time to "catch up" to the target droplets. If this channel is too short, not all tiny drops will merge with the target droplet and less than the desired amount of reagent may be added. To a certain degree, this can be compensated for by increasing the magnitude of the electric field, which tends to allow drops that are farther apart to merge. In addition to making the tiny drops on the same microfluidic device, they can also, or instead, be made offline using another microfluidic drop maker or through homogenization and then injecting them into the device containing the target droplets.

Accordingly, in certain aspects a reagent is added to a droplet prepared as described herein by a method involving emulsifying the reagent into a stream of droplets, wherein the droplets are smaller than the size of the target droplets (e.g., monodisperse single-emulsion droplets or multiple-emulsion droplets or GUVs); flowing the droplets together with the target droplets; and merging a droplet with the target droplet. The diameter of the droplets contained in the stream of droplets may vary ranging from about 75% or less than that of the diameter of the target droplet, e.g., the diameter of the flowing droplets is about 75% or less than that of the diameter of the target droplet, about 50% or less than that of the diameter of the target droplet, about 25% or less than that of the diameter of the target droplet, about 15% or less than that of the diameter of the target droplet, about 10% or less than that of the diameter of the target droplet, about 5% or less than that of the diameter of the target droplet, or about 2% or less than that of the diameter of the target droplet. In certain aspects, a plurality of flowing droplets may be merged with the target droplet, such as 2 or more droplets, 3 or more, 4 or more, or 5 or more. Such merging may be achieved by any convenient means, including but not limited to by applying an electric field, wherein the electric field is effective to merge the flowing droplet with the target droplet.

As a variation of the above-described methods, the fluids may be jetting. That is, rather than emulsifying the fluid to be added into flowing droplets, a long jet of this fluid can be formed and flowed alongside the target droplet. These two fluids can then be merged by, for example, applying an electric field. The result is a jet with bulges where the droplets are, which may naturally break apart into droplets of roughly the size of the target droplets before the merger, due to the Rayleigh plateau instability. A number of variants are contemplated. For instance, one or more agents may be added to the jetting fluid to make it easier to jet, such as gelling agents and/or surfactants. Moreover, the viscosity of the continuous fluid could also be adjusted to enable jetting, such as that described by Utada, et al., *Phys. Rev. Lett.* 99, 094502 (2007), the disclosure of which is incorporated herein by reference.

In other aspects, one or more reagents may be added using a method that uses the injection fluid itself as an electrode, by exploiting dissolved electrolytes in solution.

In another aspect, a reagent is added to a droplet formed at an earlier time by enveloping the droplet to which the reagent is to be added (i.e., the "target droplet") inside a drop containing the reagent to be added (the "target reagent"). In certain embodiments such a method is carried out by first encapsulating the target droplet in a shell of a suitable hydrophobic phase, e.g., oil, to form a double emulsion. The double emulsion is then encapsulated by a droplet containing the target reagent to form a triple emulsion. To combine the target drop with the drop containing the target reagent, the double emulsion is then burst open using any suitable method, including, but not limited to, applying an electric field, adding chemicals that destabilizes the droplet interface, flowing the triple emulsion through constrictions and other microfluidic geometries, applying shearing or ultrasound, increasing or reducing temperature, or by encapsulating magnetic particles in the droplet that can rupture the double emulsion interface when pulled by a magnetic field.

Aspects of the above-described methods of adding reagents to droplets are described in more detail in U.S. Patent Application Publication No. 2015/0232942, the disclosure of which is incorporated by reference herein in its entirety and for all purposes.

While the above methods of adding reagents to droplets may be suitable for the addition of reagents to monodisperse single-emulsion droplets, one or more of the above methods may not be suitable for the addition of reagents directly to multiple-emulsion droplets, such as double emulsion droplets, and/or GUVs. This may be the case, for example, where such methods would disrupt the structure of the multiple-emulsion droplets, and/or GUVs. The above methods may find use, however, in adding reagents to monodisperse single-emulsion droplets which are then encapsulated to form multiple-emulsion droplets, and/or GUVs. Accordingly, additional methods of adding reagents to multiple-emulsion droplets, and/or GUVs are described below. For example, in some embodiments, reagents, such as detectable labels designed to detectably label a nucleic acid amplification product and/or nucleic acid synthesis reagents designed to produce a nucleic acid synthesis product, may be added to a multiple-emulsion droplet and/or GUV by adding the reagents to a miscible phase carrier fluid, wherein the reagents diffuse from the miscible phase carrier fluid, through the immiscible shell of the multiple-emulsion droplet and/or GUV, and into the first miscible phase fluid of the multiple-emulsion droplet and/or GUV.

In some embodiments, a multiple-emulsion droplet and/or GUV is a second multiple-emulsion droplet and/or GUV and a method of adding nucleic acid synthesis reagents to the second multiple-emulsion droplet and/or GUV includes encapsulating a nucleic acid, e.g., a target nucleic acid, in a first multiple-emulsion droplet and/or GUV, encapsulating synthesis reagents and the first multiple-emulsion droplet in the second-multiple emulsion droplet and/or GUV, and rupturing the first multiple-emulsion droplet and/or GUV thereby bringing the nucleic acid into contact with the synthesis reagents.

In some embodiments, a multiple-emulsion droplet and/or GUV is a second multiple-emulsion droplet and/or GUV and a method of adding nucleic acid synthesis reagents to the second multiple-emulsion droplet and/or GUV includes encapsulating nucleic acid synthesis reagents in a first multiple-emulsion droplet and/or GUV, encapsulating a nucleic acid, e.g., a target nucleic acid, and the first multiple-emulsion droplet and/or GUV in the second-multiple emulsion droplet and/or GUV, and rupturing the first multiple-emulsion droplet and/or GUV thereby bringing the nucleic acid into contact with the synthesis reagents.

In some embodiments, a multiple-emulsion droplet and/or GUV is a first multiple-emulsion droplet and/or GUV, and a suitable method includes adding a reagent to the first multiple-emulsion droplet and/or GUV by encapsulating the first multiple-emulsion droplet and/or GUV in a second multiple-emulsion droplet and/or GUV including the reagent and rupturing the first multiple-emulsion droplet and/or GUV within the second multiple-emulsion droplet and/or GUV to bring the reagent into contact with the contents of the first multiple-emulsion droplet and/or GUV.

In some embodiments, a multiple-emulsion droplet and/or GUV is a second multiple-emulsion droplet and/or GUV, and a suitable method includes adding a reagent to the second multiple-emulsion droplet and/or GUV by encapsulating a first multiple-emulsion droplet and/or GUV including the reagents in the second multiple-emulsion droplet and/or GUV and rupturing the first multiple-emulsion droplet and/or GUV within the second multiple-emulsion droplet and/or GUV to bring the reagent into contact with the contents of the second multiple-emulsion droplet and/or GUV.

Tethering Moieties

In some embodiments, target particles e.g., nucleic acid target molecules; nucleic acid synthesis reagents; and/or nucleic acid detection reagents are attached to the monodisperse template particles via one or more tethering moieties positioned on or in the monodisperse template particles. The tethering moieties can interact with the target particles to be tethered. For example, the tethering moieties may be oligonucleotides with specific sequences which are bound on or in the monodisperse template particles. The specific oligonucleotides can hybridize to the target particles in the fluids, e.g., through base-pairing and cross-linking.

In some embodiments, certain target particles may be too large in size to move through the monodisperse template particles that contain functional groups for capturing the target particles. In such cases, the tethering moieties may be functional beads that are encapsulated in the monodisperse template particles. For example, as the target particles diffuse through the monodisperse template particles, they will come into contact with the functional beads, providing an opportunity to be captured. Even if the monodisperse template particles were absorbed in a miscible carrier fluid, the target particles would remain tethered because they would be tethered to the beads trapped in or on the monodisperse template particles.

Reactions in Single-Emulsion Droplets, Multiple-Emulsion Droplets, and/or GUVs

The methods disclosed herein generally facilitate the performance of a large numbers of compartmentalized reactions and the subsequent reading and sorting of those reactions using a variety of detection methods, such as spectroscopy, chemical techniques, biological techniques, sequencing, etc. Reactions can include organic or inorganic reactions performed without biomolecules, or reactions involving biomolecules and/or cells, such as enzymatic reactions, for example, PCR. Reactions may also involve cellular materials or cell-based extracts, including transcription and translation extracts that can express DNA, RNA, and protein without the use of living cells. This can be used for synthetic biologic applications including, for example, screening a pathway for activity.

For example, a pathway implemented by one or more proteins can be encoded by nucleic acids encapsulated in monodisperse single-emulsion droplets or multiple-emulsion droplets, e.g., double emulsions, and/or GUVs with cell-free extracts capable of expressing the one or more pathway proteins. Assay components can also be included, allowing testing of the pathway. Based on the pathway activity and measurements of the assay, the reactors can be sorted to recover monodisperse single-emulsion droplets, multiple-emulsion droplets, and/or GUVs that happened to encapsulate particularly desirable pathways. After sorting they can be analyzed, amplified, etc., to continue the process, either to perform screens or, alternatively, to perform directed evolution and generate enhanced pathway sequences.

Reactions in the monodisperse single-emulsion droplets, multiple-emulsion droplets, and/or GUVs can also be used for applications, such as nucleic acid manipulations, including the generation of sequencing libraries with less bias or to combine molecules with specific features. For example, cells expressing specific gene sequences or nucleic acid synthesis and/or amplification products can be encapsulated in the monodisperse single-emulsion droplets, multiple-emulsion droplets, and/or GUVs and then subjected to the methods as described herein to isolate, amplify and link the sequences, generating a single molecule that can be analyzed or used in additional applications. For example, if the cells include human antibody generating cells, then the genes corresponding to the heavy and light chains of the cells can be linked together to create a single molecule that can be analyzed to detect the heavy and light chain pairing or to generate an antibody like molecule, such as an scFv or Fab.

Detecting PCR Products

In practicing the subject methods, the manner in which nucleic acid synthesis and/or amplification products, e.g., isothermal nucleic acid amplification products or PCR products, can be detected may vary. For example, if the goal is simply to count the number of a particular cell type, e.g., tumor cells, present in a population, this may be achieved by using a simple binary assay in which SybrGreen, or any other stain and/or intercalating stain, is added to each monodisperse single-emulsion droplet, multiple-emulsion droplet and/or GUV so that in the event a characterizing gene, e.g., an oncogene, is present and PCR products are produced, the monodisperse single-emulsion droplet, multiple-emulsion droplet and/or GUV will become fluorescent. The change in fluorescence may be due to fluorescence polarization. The detection component may include the use of an intercalating stain (e.g., SybrGreen).

A variety of different detection components may be used in practicing the subject methods, including using fluorescent dyes known in the art. Fluorescent dyes may typically be divided into families, such as fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy®3 dye (CAS (Chemical Abstract Services) number 146368-16-3; IUPAC (International Union of Pure and Applied Chemistry) name 3-[2-[(E,3E)-3-[1-(5-carboxypentyl)-3,3-dimethylindol-2-ylidene]prop-1-enyl]-3,3-dimethylindol-1-ium-1-yl]propane-1-sulfonate), Cy®3.5 dye (CAS number 189767-45-1; IUPAC name (2Z)-2-[(E)-3-[3-(5-carboxypentyl)-1,1-dimethyl-6,8-disulfobenzo[e]indol-3-ium-2-yl] prop-2-enylidene]-3-ethyl-1,1-dimethyl-6-sulfobenzo[e]indole-8-sulfonate), Cy®5 dye (CAS number 144377 May 9; IUPAC name 3-[2-[(1E,3E,5E)-5-[1-(5-carboxypentyl)-3,3-dimethylindol-2-ylidene]penta-1,3-dienyl]-3,3-dimethylindol-1-ium-1-yl]propane-1-sulfonate), Cy®7 dye (CAS number 169799-14-8; IUPAC name (2Z)-2-[(2E,4E,6E)-7-[1-(5-carboxypentyl)-3,3-dimethyl-5-sulfoindol-1-ium-2-yl] hepta-2,4,6-trienylidene]-1-ethyl-3,3-dimethylindole-5-sulfonate), Texas Red® dye (CAS number 82354-19-6; IUPAC name 5-chlorosulfonyl-2-(3-oxa-23-aza-9-azoniaheptacyclo[17.7.1.15,9.02,17.04,15.023,27.013,28]octacosa-1(27),2 (17),4,9 (28), 13,15,18-heptaen-16-yl)benzenesulfonate), Pacific Blue™ dye (CAS number 215868-31-8; IUPAC name 6,8-difluoro-7-hydroxy-2-oxochromene-3-carboxylic acid), Oregon Green 488 (CAS number 195136-58-4; IUPAC name 2-(2,7-difluoro-3-hydroxy-6-oxoxanthen-9-yl)benzoic acid), Alexa Fluor® 488 dye (CAS number 247144-99-6; IUPAC name dilithium; 3-amino-9-[2-carboxy-5-(2,3,5,6-tetrafluorophenoxy) carbonylphenyl]-6-iminoxanthene-4,5-disulfonate), Alexa Fluor® 532 dye (CAS number 222159-92-4; IUPAC name 12-[4-(2,5-dioxopyrrolidin-1-yl)oxycarbonylphenyl]-7,8,8,16,16,17-hexamethyl-2-oxa-6,18-diazapentacyclo[11.7.0.03,11.05, 9.015,19]icosa-1 (20),3,5,9,11,13,15 (19)-heptaene-4,20-disulfonic acid), Alexa Fluor® 546 dye (CAS number 247145-23-9; IUPAC name sodium; 13-[2-carboxy-3,4,6-trichloro-5-[2-[[6-(2,5-dioxopyrrolidin-1-yl)oxy-6-oxohexyl]amino]-2-oxoethyl]sulfanylphenyl]-7,7,9,17,19,19-hexamethyl-2-oxa-6,20-diazapentacyclo[12.8.0.03,12.05,10 016,21]docosa-1 (14),3,5,10,12,15,21-heptaene-4,22-disulfonate;hydron), Alexa Fluor® 555 dye (CAS number 644990-77-2; 4-(3-amino-6-imino-4,5-disulfoxanthen-9-yl) benzene-1,3-dicarboxylic acid), Alexa Fluor® 568 dye (CAS number 247145-38-6; IUPAC name 4-(2,5-dioxopyrrolidin-1-yl)oxycarbonyl-2-[7,7,19,19-tetramethyl-9,17-bis (sulfomethyl)-2-oxa-6,20-diazapentacyclo[12.8.0.03,12.05, 10.016,21]docosa-1 (14),3,5,8,10,12, 15, 17,21-nonaen-13-yl]benzoic acid), Alexa Fluor® 594 dye (CAS number 247145-86-4; IUPAC name [13-[2-carboxy-5-(2,5-dioxopyrrolidin-1-yl)oxycarbonylphenyl]-6,7,7,19,19,20-hexamethyl-17-(sulfomethyl)-2-oxa-20-aza-6-azoniapentacyclo [12.8.0.03,12.05,10 016,21]docosa-1 (14),3,5,8,10,12,15, 17,21-nonaen-9-yl]methanesulfonate), Alexa Fluor® 647 dye (CAS number 400051-23-2; 2-[5-[3,3-dimethyl-5-sulfo-1-(3-sulfopropyl) indol-1-ium-2-yl]penta-2,4-dienylidene]-3-methyl-3-[5-oxo-5-(6-phosphonooxyhexylamino) pentyl]-1-(3-sulfopropyl) indole-5-sulfonic acid), JOE™ dye (CAS number 113394-23-3; IUPAC name (2,5-dioxopyrrolidin-1-yl) 4',5'-dichloro-3',6'-dihydroxy-2',7'-dimethoxy-1-oxospiro [2-benzofuran-3,9'-xanthene]-5-carboxylate), Lissamine, Rhodamine Green™ dye (CAS number 189200-71-3; IUPAC name [6-amino-9-(2,4-dicarboxyphenyl) xanthen-3-ylidene]azanium), BODIPY (IUPAC name 2,2-difluoro-3-aza-1-azonia-2-boranuidatricyclo[7.3.0.03,7]dodeca-1 (12),4,6,8,10-pentaene), fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ (IUPAC name 2-[[(2R)-2-[bis(carboxymethyl)amino]-3-14-(carbamothioylamino)phenyl|propyl]-[(1S,2S)-2-[bis (carboxymethyl)amino]cyclohexyl]amino]acetic acid), VIC (IUPAC name 2'-chloro-7'phenyl-1,4-dichloro-6-carboxy-fluorescein), NED (IUPAC name 2'-chloro-5'-fluoro-7',8'-benzo-1,4-dichloro-6-carboxyfluorescein), PET (IUPAC name 4-[2-[2-(4-carbamimidoylphenoxy)ethoxy]ethoxy] benzenecarboximidamide), SYBR (IUPAC name N,N-dimethyl-N'-[4-[(E)-(3-methyl-1,3-benzothiazol-2-ylidene) methyl]-1-phenylquinolin-1-ium-2-yl]-N'-propylpropane-1, 3-diamine), PicoGreen® (IUPAC name N'-[3-(dimethylamino)propyl]-N,N-dimethyl-N'-[4-[(E)-(3-methyl-1,3-benzothiazol-2-ylidene)methyl]-1-phenylquinolin-1-ium-2-yl]propane-1,3-diamine), and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, VA.

In other aspects, particularly if a goal is to further characterize the nucleic acids present, e.g., oncogenes, additional testing may be needed. For instance, in the case of the multiplex assays this may be achieved by having optical outputs that relate which of the gene(s) are amplified in the monodisperse single-emulsion droplet, multiple-emulsion droplet and/or GUV. An alternative approach would be to use a binary output, for example, with an intercalated stain, to determine which monodisperse single-emulsion droplets, multiple-emulsion droplets, and/or GUVs have any oncogenes. These can then be sorted to recover these droplets and/or GUVs so that they could be analyzed in greater detail to determine which oncogenes they contain. To determine the oncogenes present in such a droplet and/or GUV, microfluidic techniques or nonmicrofluidic techniques could be used. Using non-microfluidic techniques, a droplet and/or GUV identified as containing an oncogene can be placed into a well on a well plate where it is diluted into a larger volume, releasing all of the PCR products that were created during the multiplexed PCR reaction. Samples from this well can then be transferred into other wells, into each of which would be added primers for one of the oncogenes. These wells would then be temperature-cycled to initiate PCR, at which point an intercalating stain would be added to cause wells that have matching oncogenes and primers to light up.

In practicing the subject methods, therefore, a component may be detected based upon, for example, a change in fluorescence. In certain aspects, the change in fluorescence is due to fluorescence resonance energy transfer (FRET). In this approach, a special set of primers may be used in which the 5' primer has a quencher dye and the 3' primer has a fluorescent dye. These dyes can be arranged anywhere on the primers, either on the ends or in the middles. Because the primers are complementary, they will exist as duplexes in solution, so that the emission of the fluorescent dye will be quenched by the quencher dye, since they will be in close proximity to one another, causing the solution to appear dark. After PCR, these primers will be incorporated into the long PCR products, and will therefore be far apart from one another. This will allow the fluorescent dye to emit light, causing the solution to become fluorescent. Hence, to detect if a particular oncogene is present, one may measure the intensity of the droplet and/or GUV at the wavelength of the fluorescent dye. To detect if different oncogenes are present, this would be done with different colored dyes for the different primers. This would cause the droplet and/or GUV to become fluorescent at all wavelengths corresponding to the primers of the oncogenes present in the cell.

Detecting Cells (e.g., Tumor Cells) in Single-Emulsion Droplets, Multiple-Emulsion Droplets, and/or GUVs Aspects of the subject methods involve detecting the presence of one or more cells or subsets of cells (e.g., tumor cells) in a biological sample. Such methods may include, for example, steps of encapsulating a cell in a monodisperse single-emulsion droplet, multiple-emulsion droplet, and/or GUV; subjecting the monodisperse single-emulsion droplet, multiple-emulsion droplet, and/or GUV to conditions sufficient to effect lysis of the cell in the monodisperse single-emulsion droplet, multiple-emulsion droplet, and/or GUV; subjecting the monodisperse single-emulsion droplet, multiple-emulsion droplet, and/or GUV to conditions sufficient to deactivate or remove one or more materials which have an inhibitory effect on nucleic acid amplification; introducing nucleic acid synthesis reagents, e.g., nucleic acid amplification reagents, into the monodisperse single-emulsion droplet, multiple-emulsion droplet, and/or GUV; subjecting the monodisperse single-emulsion droplet, multiple-emulsion droplet, and/or GUV to nucleic acid synthesis conditions, e.g., nucleic acid amplification conditions, sufficient to result in synthesis, e.g., amplification, of a target nucleic acid when present; and detecting an amplification or synthesis product resulting from the synthesis, e.g., amplification, of the target nucleic acid when present.

A biological sample (e.g., whole blood) may be recovered from a subject using any convenient means. The biological sample may be processed to remove components other than cells using, for example, processing steps such as centrifugation, filtration, and the like. Where desired, the cells may be stained with one or more antibodies and/or probes prior to encapsulating them into monodisperse single-emulsion droplets, multiple-emulsion droplets, and/or GUVs.

One or more lysing agents may also be added to the monodisperse single-emulsion droplets, multiple-emulsion droplets, and/or GUVs containing a cell, under conditions in which the cell(s) may be caused to burst, thereby releasing their genomes. The lysing agents may be added after the cells are encapsulated into monodisperse single-emulsion droplets, multiple-emulsion droplets, and/or GUVs. Any suitable lysing agent may be employed, such as any suitable protease and/or proteinase (e.g., a protease and/or proteinase having broad substrate specificity, e.g., a non-specific serine protease, e.g., proteinase K, a protease from *Bacillus licheniformis* (e.g., CAS Number 9014-01-1), OB protease (available from Omega Bio-Tek), or cytotoxins. In particular embodiments, cells may be co-encapsulated in monodisperse single-emulsion droplets, multiple-emulsion droplets, and/or GUVs with lysis buffer containing detergents such as Triton X-100 and/or proteinase K. The specific conditions in which the cell(s) may be caused to burst will vary depending on the specific lysing agent used. For example, if proteinase K is incorporated as a lysing agent, the monodisperse single-emulsion droplets, multiple-emulsion droplets, and/or GUVs may be heated to about 37-60° C. for about 15 to 20 min to lyse the cells and to allow the proteinase K to digest cellular proteins, after which they may be heated to about 95° C. for about 5-10 min to deactivate the proteinase K.

In certain aspects, lysing agents may be added to cells prior to or concurrently with encapsulation of the cells into monodisperse single-emulsion droplets, multiple-emulsion droplets, and/or GUVs as described herein. Any convenient lysing agent may be employed, such as any suitable protease and/or proteinase (e.g., a protease and/or proteinase having broad substrate specificity, e.g., a non-specific serine protease, e.g., proteinase K, a protease from *Bacillus licheniformis* (e.g., CAS Number 9014-01-1), OB protease (available from Omega Bio-Tek), or cytotoxins. In some embodiments, detergents are specifically not utilized as this can result in premature cell lysis prior to encapsulation. In such embodiments, the protease and/or proteinase, e.g., proteinase K, may be added to the cells, e.g., in the absence of detergents, prior to or concurrently with, encapsulation of the cells into monodisperse single-emulsion droplets, multiple-emulsion droplets, and/or GUVs. The protease and/or proteinase, e.g., proteinase K, may be added at a temperature low enough to ensure that the protease and/or proteinase is not in an activated state prior to or during cell encapsulation, e.g., about 0° C. to about 25° C., including about 1° C. to about 5° C., about 1° C. to about 10° C., about 1° C. to about 15° C., and about 1° C. to about 20° C. In some embodiments, the protease and/or proteinase may be added at about 4° C. Subsequently, the temperature of the monodisperse single-emulsion droplets, multiple-emulsion droplets, and/or GUVs may be increased to a temperature sufficient to ensure activation of the protease and/or proteinase, e.g., 37-80° C., such as 30-50° C., 37-55° C., 40-60° C., 50-60° C., 60-70° C., or 70-80° C., to facilitate protease and/or proteinase activation and cell lysis. The protease and/or proteinase incubation may be for a time sufficient to result in cell lysis, e.g., 15-60 min (or longer as appropriate), e.g., 15-20 minutes. The emulsion may then be broken and the protease and/or proteinase washed out as necessary. Such methods find use, e.g., in the single cell RNA sequencing (scRNAseq) methods described herein.

In certain aspects, cell lysis may also, or instead, rely on techniques that do not involve addition of lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient means of effecting cell lysis may be employed in the methods described herein.

Primers may be introduced into the monodisperse single-emulsion droplets, multiple-emulsion droplets, and/or GUVs for each of the genes and/or genetic markers, e.g., oncogenes, to be detected. Hence, in certain aspects, primers for a variety of genes and/or genetic markers, e.g., all oncogenes may be present in the monodisperse single-emulsion droplets, multiple-emulsion droplets, and/or GUVs at the same time, thereby providing a multiplexed assay. The droplets and/or GUVs may be temperature-cycled so that the droplets and/or GUVs containing target cells, e.g., cancerous cells, will undergo PCR. Alternatively, or in addition, MDA or other isothermal nucleic acid amplification methods may be utilized, e.g., loop-mediated isothermal nucleic acid amplification (LAMP), strand displacement amplification (SDA), helicase-dependent amplification (HDA), and nicking enzyme amplification reaction (NEAR). Only the primers corresponding to oncogenes and/or genetic markers present in the genome will induce amplification, creating many copies of these oncogenes and/or genetic markers in the droplets and/or GUVs. Detecting the presence of these amplification products may be achieved by a variety of ways, such as by using FRET, staining with an intercalating dye, or attaching them to a bead. The droplets and/or GUVs may be optically probed to detect the amplification products. In some embodiments, optically probing the droplets and/or GUVs may involve counting the number of tumor cells present in the initial population, and/or allowing for the identification of the oncogenes present in each tumor cell.

The subject methods may be used to determine whether a biological sample contains particular cells of interest, e.g., tumor cells, or not. In certain aspects, the subject methods may include quantifying the number of cells of interest, e.g., tumor cells, present in a biological sample. Quantifying the number of cells of interest, e.g., tumor cells, present in a biological sample may be based at least in part on the number of droplets and/or GUVs in which amplification products were detected. For example, droplets and/or GUVs may be produced under conditions in which the majority of droplets are expected to contain zero or one cell. Those droplets and/or GUVs that do not contain any cells may be removed, using techniques described more fully herein. After performing the PCR steps outlined above, the total number of droplets and/or GUVs that are detected to contain amplification products may be counted, so as to quantify the number of cells of interest, e.g., tumor cells, in the biological sample. In certain aspects, the methods may also include counting the total number of droplets and/or GUVs so as to determine the fraction or percentage of cells from the biological sample that are cells of interest, e.g., tumor cells.

In some embodiments, the introduction of synthesis reagents into multiple-emulsion droplets, and/or GUVs prepared from monodisperse droplets as described herein includes introducing the synthesis reagents into the third fluid, wherein the synthesis reagents diffuse from the third fluid, through the immiscible shell, and into the first fluid of the multiple-emulsion droplets, and/or GUVs.

The cells and/or cellular material of interest may be recovered by sorting the monodisperse single-emulsion droplets, multiple-emulsion droplets, and/or GUVs and recovering their contents via droplet rupture, e.g., through chemical, electrical, or mechanical means as described in greater detail herein. A variety of suitable sorting techniques and related devices may be utilized to sort and separate the monodisperse single-emulsion droplets, multiple-emulsion droplets, and/or GUVs containing amplification and/or synthesis products including those described herein.

Nucleic Acid Detection in Single-Emulsion Droplets, Multiple-Emulsion Droplets, and/or GUVs As discussed herein, the disclosed methods find use in the detection of nucleic acids, e.g., DNA or RNA, of interest from a variety of biological samples. Such methods may include, for example, steps of encapsulating a nucleic acid and synthesis reagents in a monodisperse single-emulsion droplet, multiple-emulsion droplet and/or GUV; subjecting the monodisperse single-emulsion droplet, multiple-emulsion droplet and/or GUV to amplification conditions sufficient to result in amplification of the nucleic acid; and detecting an amplification product resulting from the amplification of the nucleic acid. The amplification conditions may be MDA conditions and/or PCR conditions e.g., RT-PCR conditions, and/or additional isothermal nucleic acid amplification conditions, e.g., loop-mediated isothermal nucleic acid amplification (LAMP), strand displacement amplification (SDA), helicase-dependent amplification (HDA), and nicking enzyme amplification reaction (NEAR).

The nucleic acids of interest may be recovered by sorting the monodisperse single-emulsion droplets, multiple-emulsion droplets, and/or GUVs and recovering their contents via droplet rupture, e.g., through chemical, electrical, or mechanical means as described in greater detail herein. A variety of suitable sorting techniques and related devices may be utilized to sort and separate the monodisperse single-emulsion droplets, multiple-emulsion droplets, and/or GUVs containing amplification products including those described herein. In one aspect, a method for enriching for a target nucleic acid sequence is provided, wherein the method includes encapsulating a sample including nucleic acids in a plurality of monodisperse single-emulsion droplets, multiple-emulsion droplets, and/or GUVs; introducing MDA reagents and polymerase chain reaction (PCR) reagents and a plurality of suitable primers into the monodisperse single-emulsion droplets, multiple-emulsion droplets, and/or GUVs; incubating the monodisperse single-emulsion droplets, multiple-emulsion droplets, and/or GUVs under conditions sufficient for MDA amplification and conditions sufficient for PCR amplification to produce MDA amplification products and PCR amplification products, respectively, wherein suitable PCR primers may include one or more primers that each hybridize to one or more oligonucleotides incorporating the target nucleic acid sequence, and wherein the PCR amplification products do not include the entire target nucleic acid sequence; introducing a detection component into the monodisperse single-emulsion droplets, multiple-emulsion droplets, and/or GUVs either before or after the incubating; detecting the presence or absence of the PCR amplification products by detection of the detection component, wherein detection of the detection component indicates the presence of PCR amplification products and the target nucleic acid sequence; and sorting the monodisperse single-emulsion droplets, multiple-emulsion droplets, and/or GUVs based on detection of the detection component, wherein the sorting separates monodisperse single-emulsion droplets, multiple-emulsion droplets, and/or GUVs including the PCR amplification products and the target nucleic acid sequence, when present, from monodisperse single-emulsion droplets, multiple-emulsion droplets, and/or GUVs which do not include the PCR amplification products and the target nucleic acid sequence; and pooling the nucleic acid sequences from the sorted monodisperse single-emulsion droplets, multiple-emulsion droplets, and/or GUVs to provide an enriched pool of target nucleic acid sequences, when present. One or more of these steps may be performed under microfluidic control.

The above method allows, for example, for the enrichment of DNA molecules out of a heterogeneous system based on the presence of PCR-detectable subsequences. The DNA molecules can be short (e.g., hundreds of bases) or long (e.g., megabases or longer). The sample may be encapsulated in monodisperse droplets such that target molecules are detected in the droplets digitally—i.e., each droplet contains 0 or 1 target molecule. The monodisperse droplets may then be sorted based on, e.g., fluorescence, to recover the target molecules. This method can be used to enrich for a large genomic region, e.g., on the order of megabases in length, in a heterogeneous sample of DNA fragments.

The above method enables a sufficient amount of DNA to be recovered without the need to perform PCR to amplify the DNA for sequencing. Amplification-free DNA sample prep is valuable, for example, where PCR does not preserve the sequences or epigenetic factors of interest, or cannot recover sequences that are of the needed length (e.g., greater than about 10 kb, the practical limit of long-range PCR).

Another application of the above method is to enrich DNA for epigenetic sequencing. Epigenetic marks on DNA are not preserved by PCR, so sequencing them requires unamplified DNA from the host nucleic acids. With the above method, a sufficient amount of DNA can be obtained for sequencing without needing to perform PCR, and thus preserving the epigenetic marks.

The above methods have particular utility where the length of the target nucleic acid exceeds the practical limits of long-range PCR, e.g., where the nucleic acid is greater than about 10 kb, and/or where it is desirable to preserve epigenetic marks on the DNA. In some embodiments, the target nucleic acid to be enriched is greater than about 100 kb in length, e.g., greater than about 1 megabase in length. In some embodiments, the target nucleic acid to be enriched is from about 10 kb to about 100 kb, from about 100 kb to about 500 kb, or from about 500 kb to about 1 megabase in length.

Post-amplification and/or purification, emulsions can be broken using both chemical and osmotic means for future analysis. For example, an equal volume of 1H, 1H, 2H, 2H-Perfluoro-1-octanol can be added to a purified sample and mixed either through pipetting or vortexing. The resulting mixture can then be allowed to equilibrate, and the aqueous layer can be eluted off for further analysis. Similarly, a large excess of purified water can be added to the sample post-sort, mixed, and allowed to incubate at room temperature for several hours. The resulting mixture can then be analyzed directly for purified sample of interest.

Multiple Displacement Amplification

As summarized above, in practicing methods of the invention MDA may be used to amplify nucleic acids, e.g., genomic DNA, in a generally unbiased and non-specific manner for downstream analysis, e.g., via next generation sequencing.

An exemplary embodiment of a method as described herein includes encapsulating in a monodisperse droplet (e.g., monodisperse single-emulsion droplet or multiple emulsion monodisperse droplet) a nucleic acid template molecule obtained from a biological sample, introducing MDA reagents and a plurality of MDA primers into the monodisperse droplet, and incubating the monodisperse droplet under conditions effective for the production of MDA amplification products, wherein the incubating is effective to produce MDA amplification products from the nucleic acid template molecule. In some embodiments the encapsulating and introducing steps occur as a single step, e.g., where the nucleic acid template molecule is mixed with MDA reagents and a plurality of MDA primers, and emulsified, e.g., using a flow focusing element of a microfluidic device.

The conditions of MDA-based assays described herein may vary in one or more ways. For instance, the number of MDA primers that may be added to (or encapsulated in) a monodisperse droplet may vary. The term "primer" refers to one or more primers and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as a suitable DNA polymerase (e.g., Φ29 DNA polymerase or Bst DNA polymerase), in a suitable buffer ("buffer" includes substituents which are cofactors, or which affect pH, ionic strength, etc.), and at a suitable temperature. The primer is preferably single-stranded for maximum efficiency in amplification. In the context of MDA, random hexamer primers are regularly utilized.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The number of MDA primers that may be added to (or encapsulated in) a monodisperse droplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

Such primers and/or reagents may be added to a monodisperse droplet in one step, or in more than one step. For instance, the primers may be added in two or more steps, three or more steps, four or more steps, or five or more steps. Where a lysing agent is utilized, regardless of whether the primers are added in one step or in more than one step, they may be added after the addition of a lysing agent, prior to the addition of a lysing agent, or concomitantly with the addition of a lysing agent. When added before or after the addition of a lysing agent, the MDA primers may be added in a separate step from the addition of a lysing agent.

Once primers have been added to a monodisperse droplet, the monodisperse droplet may be incubated under conditions sufficient for MDA. The monodisperse droplet may be incubated on the same microfluidic device as was used to add the primer(s), or may be incubated on a separate device. In certain embodiments, incubating the monodisperse droplet under conditions sufficient for MDA amplification is performed on the same microfluidic device used for cell lysis. Incubating the monodisperse droplets may take a variety of forms, for example monodisperse droplets may be incubated at a constant temperature, e.g., 30 deg. C., e.g., for about 8 to about 16 hours. Alternatively, cycles of 25° C. for 5 minutes followed by 42° C. for 25 minutes may be utilized.

Although the methods described herein for producing MDA amplification products do not require the use of specific probes, the methods of the invention may also include introducing one or more probes to the monodisperse droplet. As used herein with respect to nucleic acids, the term "probe" generally refers to a labeled oligonucleotide which forms a duplex structure with a sequence in the target nucleic acid, due to complementarity of at least one sequence in the probe with a sequence in the target region. The probe, preferably, does not contain a sequence complementary to sequence(s) used to prime the MDA reaction. The number of probes that are added may be from about one to 500, e.g., about 1 to 10 probes, about 10 to 20 probes, about 20 to 30 probes, about 30 to 40 probes, about 40 to 50 probes, about 50 to 60 probes, about 60 to 70 probes, about 70 to 80 probes, about 80 to 90 probes, about 90 to 100 probes, about 100 to 150 probes, about 150 to 200 probes, about 200 to 250 probes, about 250 to 300 probes, about 300 to 350 probes, about 350 to 400 probes, about 400 to 450 probes, about 450 to 500 probes, or about 500 probes or more. The probe(s) may be introduced into the monodisperse droplet prior to, subsequent with, or after the addition of the one or more primer(s).

In certain embodiments, an MDA based assay may be used to detect the presence of certain RNA transcripts present in cells or to sequence the genome of one or more RNA viruses. In such embodiments, MDA reagents may be added to the monodisperse droplet using any of the methods described herein. Prior to or after addition (or encapsulation) of the MDA reagents, the monodisperse droplet may be incubated under conditions allowing for reverse transcription followed by conditions allowing for MDA as described herein. The monodisperse droplet may be incubated on the same microfluidic device as is used to add the MDA reagents, or may be incubated on a separate device. In certain embodiments, incubating the monodisperse droplet under conditions allowing for MDA is performed on the same microfluidic device used to encapsulate and/or lyse one or more cells.

In certain embodiments, the reagents added to the monodisperse droplet for MDA further includes a fluorescent DNA probe capable of detecting MDA amplification products. Any suitable fluorescent DNA probe can be used including, but not limited to SYBR Green, TaqMan®, Molecular Beacons and Scorpion probes. In certain embodiments, the reagents added to the monodisperse droplet include more than one DNA probe, e.g., two fluorescent DNA probes, three fluorescent DNA probes, or four fluorescent DNA probes. The use of multiple fluorescent DNA probes allows for the concurrent measurement of MDA amplification products in a single reaction.

PCR

As summarized above, in practicing methods of the invention a PCR-based assay may be used to detect the presence of certain nucleic acids of interest, e.g., genes of interest and/or genetic markers, e.g., oncogene(s), present in cells or a heterogeneous sample of nucleic acids. Such PCR based assays may be performed in the same monodisperse droplet, e.g., monodisperse single-emulsion droplet or multiple emulsion monodisperse droplet as a previous or subsequent MDA amplification step. In other embodiments, PCR reactions may be conducted in monodisperse droplets independently. The conditions of such PCR-based assays may vary in one or more ways.

For instance, the number of PCR primers that may be added to a monodisperse single-emulsion droplet or multiple-emulsion droplet and/or GUV may vary. The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The number of PCR primers that may be added to a monodisperse single-emulsion droplet or multiple-emulsion droplet and/or GUV may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

These primers may contain primers for one or more gene of interest, e.g. oncogenes. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more. Genes and oncogenes of interest include, but are not limited to, BAX, BCL2L1, CASP8, CDK4, ELK1, ETS1, HGF, JAK2, JUNB, JUND, KIT, KITLG, MCL1, MET, MOS, MYB, NFKBIA, EGFR, Myc, EpCAM, NRAS, PIK3CA, PML, PRKCA, RAF1, RARA, REL, ROS1, RUNX1, SRC, STAT3, CD45, cytokeratins, CEA, CD133, HER2, CD44, CD49f, CD146, MUC1/2, and ZHX2.

Such primers and/or reagents may be added to a monodisperse single-emulsion droplet or multiple-emulsion droplet and/or GUV in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent.

Once primers have been added to a monodisperse single-emulsion droplet or multiple-emulsion droplet and/or GUV the monodisperse single-emulsion droplet or multiple-emulsion monodisperse droplet and/or GUV may be incubated under conditions allowing for PCR. The monodisperse single-emulsion droplet or multiple-emulsion droplet and/or GUV may be incubated on the same microfluidic device as was used to add the primer(s), or may be incubated on a separate device. In certain embodiments, incubating the monodisperse single-emulsion droplet or multiple-emulsion droplet and/or GUV under conditions allowing for PCR amplification is performed on the same microfluidic device used to encapsulate and lyse cells. Incubating the monodisperse single-emulsion droplet or multiple-emulsion droplet and/or GUV may take a variety of forms. In certain aspects, the monodisperse single-emulsion droplet or multiple-emulsion droplet and/or GUV containing the PCR mix may be flowed through a channel that incubates the monodisperse droplets under conditions effective for PCR. In some embodiments, PCR reactions are performed without the use of microfluidic devices and/or systems. Flowing the monodisperse single-emulsion droplet or multiple-emulsion droplet and/or GUV through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. Alternatively, zones for 86° C., 60° C. and 20° C. may be utilized. As the monodisperse single-emulsion droplets or multiple-emulsion and/or GUVs move through such zones, their temperature cycles, as needed for PCR. The precise number of zones, and the respective temperature of each zone, may be readily determined by those of skill in the art to achieve the desired PCR amplification.

In other embodiments, incubating the monodisperse single-emulsion droplets or multiple-emulsion droplets and/or GUVs may involve the use of a Megadroplet Array. In such a device, an array of hundreds, thousands, or millions of traps indented into a channel (e.g., a PDMS channel) sit above a thermal system. The channel may be pressurized, thereby preventing gas from escaping. The height of the microfluidic channel is smaller than the diameter of the monodisperse single-emulsion droplets or multiple-emulsion droplets and/or GUVs, causing monodisperse single-emulsion droplets or multiple-emulsion droplets and/or GUVs to adopt a flattened pancake shape. When a monodisperse single-emulsion droplet or multiple-emulsion droplet and/or GUV flows over an unoccupied indentation, it adopts a lower, more energetically favorable, radius of curvature, leading to a force that pulls the monodisperse single-emulsion droplets or multiple-emulsion droplet and/or GUV entirely into the trap. By flowing monodisperse single-emulsion droplets or multiple-emulsion droplets and/or GUVs as a close pack, it is ensured that all traps on the array are occupied. The entire device may be thermal cycled using a heater.

In certain aspects, the heater includes a Peltier plate, heat sink, and control computer. The Peltier plate allows for the heating or cooling of the chip above or below room temperature by controlling the applied current. To ensure controlled and reproducible temperature, a computer may monitor the temperature of the array using integrated temperature probes, and may adjust the applied current to heat and cool as needed. A metallic (e.g. copper) plate allows for uniform application of heat and dissipation of excess heat during cooling cycles, enabling cooling from about 95° C. to about 60° C. in under about one minute.

Methods of the invention may also include introducing one or more probes to the monodisperse single-emulsion droplets or multiple-emulsion droplets and/or GUVs. As used herein with respect to nucleic acids, the term "probe" refers to a labeled oligonucleotide which forms a duplex structure with a sequence in the target nucleic acid, due to complementarity of at least one sequence in the probe with a sequence in the target region. In some embodiments, the probe does not contain a sequence complementary to sequence(s) used to prime the polymerase chain reaction. The number of probes that are added may be from about one to 500, e.g., about 1 to 10 probes, about 10 to 20 probes, about 20 to 30 probes, about 30 to 40 probes, about 40 to 50 probes, about 50 to 60 probes, about 60 to 70 probes, about 70 to 80 probes, about 80 to 90 probes, about 90 to 100 probes, about 100 to 150 probes, about 150 to 200 probes, about 200 to 250 probes, about 250 to 300 probes, about 300 to 350 probes, about 350 to 400 probes, about 400 to 450 probes, about 450 to 500 probes, or about 500 probes or more. The probe(s) may be introduced into the monodisperse single-emulsion droplets, multiple-emulsion droplets and/or GUVs prior to, subsequent with, or after the addition of the one or more primer(s). Probes of interest include, but are not limited to, TaqMan® probes (e.g., as described in Holland, P. M.; Abramson, R. D.; Watson, R.; Gelfand, D. H. (1991), "Detection of specific polymerase chain reaction product by utilizing the 5'----3' exonuclease activity of *Thermus aquaticus* DNA polymerase", PNAS, 88 (16): 7276-7280).

In certain embodiments, an RT-PCR based assay may be used to detect the presence of certain transcripts of interest, e.g., oncogene(s), present in cells. In such embodiments, reverse transcriptase and any other reagents necessary for cDNA synthesis are added to the monodisperse single-emulsion droplets or multiple-emulsion droplets and/or GUVs in addition to the reagents used to carry out PCR described herein (collectively referred to as the "RT-PCR reagents"). The RT-PCR reagents are added to the monodisperse single-emulsion droplets or multiple-emulsion droplets and/or GUVs using any of the suitable methods described herein. Once reagents for RT-PCR have been added to a monodisperse single-emulsion droplet or multiple-emulsion droplet and/or GUV, the monodisperse single-emulsion droplet or multiple-emulsion droplet and/or GUV may be incubated under conditions allowing for reverse transcription followed by conditions allowing for PCR as described herein. The monodisperse single-emulsion droplet or multiple-emulsion droplet and/or GUV may be incubated on the same microfluidic device as was used to add the RT-PCR reagents, or may be incubated on a separate device. In certain embodiments, incubating the monodisperse single-emulsion droplet or multiple-emulsion droplet and/or GUV under conditions allowing for RT-PCR is performed on the same microfluidic device used to encapsulate and lyse cells.

In certain embodiments, the reagents added to the monodisperse single-emulsion droplet or multiple-emulsion droplet and/or GUV for RT-PCR or PCR further includes a fluorescent DNA probe capable of detecting RT-PCR or PCR products. Any suitable fluorescent DNA probe can be used including, but not limited to SYBR Green, TaqMan®, Molecular Beacons and Scorpion probes. In certain embodiments, the reagents added to the monodisperse single-emulsion droplets or multiple-emulsion droplet and/or GUV include more than one DNA probe, e.g., two fluorescent DNA probes, three fluorescent DNA probes, or four fluorescent DNA probes. The use of multiple fluorescent DNA probes allows for the concurrent measurement of RT-PCR or PCR products in a single reaction.

Double PCR

To amplify rare transcripts, a monodisperse single-emulsion droplet, a multiple-emulsion droplet and/or GUV that has undergone a first-step RT-PCR or PCR reaction as described herein may be further subjected to a second step PCR reaction. In some embodiments, a first monodisperse single-emulsion droplet, multiple-emulsion droplet and/or GUV that has undergone a first-step RT-PCR or PCR reaction is encapsulated in a second single-emulsion droplet, multiple-emulsion droplet and/or GUV containing additional PCR reagents, including, but not limited to enzymes (e.g. DNA polymerase), DNA probes (e.g. fluorescent DNA probes) and primers, followed by rupture of the first monodisperse single-emulsion droplet, multiple-emulsion droplet and/or GUV. In certain embodiments, the second single-emulsion droplet, multiple-emulsion droplet and/or GUV containing the additional PCR reagents is larger than the monodisperse droplet that has undergone the first step RT-PCR or PCR reaction. This may be beneficial, for example, because it allows for the dilution of cellular components that may be inhibitory to the second step PCR. The second step PCR reaction may be carried out on the same microfluidic device used to carry out the first-step reaction, on a different microfluidic device, or without the use of a microfluidic device.

In some embodiments, the primers used in the second step PCR reaction are the same primers used in the first step RT-PCR or PCR reaction. In other embodiments, the primers used in the second step PCR reaction are different than the primers used in the first step reaction.

Digital PCR

The methods described herein can be used to quantitate nucleic acids using, for example, digital PCR. In digital PCR, target nucleic acids from a solution are diluted such that, when the sample is isolated in compartments, most compartments encapsulate either zero or one target molecule, although higher loading rates can often be used, provided they can be modeled. Reagents sufficient for amplification of the target nucleic acids are also included in the compartments, and the compartments subjected to conditions suitable for amplification. The compartments can have a variety of structures, including fabricated microwells in a substrate or single-emulsion droplets. They may also be formed as, for example, monodisperse single-emulsion droplets, multiple-emulsion monodisperse droplets, e.g., double emulsions, and/or GUVs, as described herein. In some embodiments, the sample is compartmentalized in monodisperse single-emulsion droplets, multiple-emulsion monodisperse droplets, e.g., double emulsions, and/or GUVs and the monodisperse single-emulsion droplets, multiple-emulsion monodisperse droplets, e.g., double emulsions, and/or GUVs are subjected to amplification conditions. Droplets that contain a target undergo amplification, while those that do not, do not undergo amplification, and therefore do not yield nucleic acid amplification products. If a detection component is included, single or multiple emulsions that include the target may fill with a detectable signal, allowing them to be identified by, for example, imaging or flow dropometry. A powerful advantage of using double emulsions to perform such digital PCR is that the double emulsions can be suspended in an aqueous carrier phase that is miscible with the partitioned sample, and can therefore readily be detected and/or sorted using commercially available flow cytometers and fluorescence activated cell sorters (FACS). This allows for enrichments of target entities out of a sample that is not possible with other methods in which sorting is not easily accomplished.

In some embodiments, the disclosed methods can be used to quantitate nucleic acids in solution by counting the fraction of single or multiple emulsions that are fluorescent and undergo amplification and thus contain at least a single target nucleic acid, in most instances; false amplification may occur for stochastic reasons or, for example, the encapsulation of dust or other contaminants that interfere with the specificity of the amplification reaction. TaqMan® probes, molecular beacons, SYBR, and other kinds of detection components can also be included, allowing the use of multiple optical spectra for simultaneously detecting the amplification of different nucleic acid sequences in the target or due to multiple targets being encapsulated in the same monodisperse single-emulsion droplets, multiple-emulsion monodisperse droplets, e.g., double emulsions, and/or GUVs, which may be advantageous in some instances.

Like other PCR analysis methods, dPCR can be multiplexed using probes labeled with different fluorescent dyes. Since dPCR acts on molecules in droplets, this provides unique measurement opportunities not possible with common methods, like the physical association of distinct sequences. This is valuable for a variety of important applications in genomic biology, including characterizing virus diversity, phasing microbial genomes, haplotyping cancer genomes, measuring mRNA splice forms, and characterizing length distributions of target molecules in solution.

RNA Sequencing (RNAseq)

The methods disclosed herein can be used for single cell encapsulation and RNAseq. RNAseq utilizes the massive parallel sequencing made possible by next generation sequencing (NGS) technologies, another way to approach the enumeration of RNA transcripts in a tissue sample. Specifically, RNAseq can be used to study phenomena such as gene expression changes, alternative splicing events, allele-specific gene expression, and chimeric transcripts, including gene fusion events, novel transcripts and RNA editing. Complementary DNA (cDNA) may be recovered from the monodisperse emulsions and standard in vitro transcription and library preparation for NGS performed to collect the data of single cell gene expression profile analysis.

A single cell RNA sequencing method is provided herein, which method includes: combining a plurality of monodisperse template particles with a first fluid to provide a first mixture, wherein the first fluid comprises a plurality of cells; combining the first mixture with a second fluid to provide a second mixture, wherein the second fluid is immiscible with the first fluid; and shearing the second mixture such that a plurality of the monodisperse template particles are encapsulated in a plurality of monodisperse droplets in the second fluid, thereby providing a plurality of monodisperse droplets comprising the first fluid, one of the monodisperse template particles, and one of the plurality of cells. Such a method may include a cell lysis step as described herein, e.g., a protease and/or proteinase lysis step as described herein, e.g., a proteinase K lysis step as described herein. For example, a protease and/or proteinase, e.g., protease and/or proteinase having broad substrate specificity, e.g., a non-specific serine protease, e.g., proteinase K, a protease from *Bacillus licheniformis* (e.g., CAS Number 9014-01-1), or OB protease (available from Omega Bio-Tek) may be added to the cells, e.g., in the absence of detergents, prior to or concurrently with, encapsulation of the cells into monodisperse single-emulsion droplets, multiple-emulsion droplets, and/or GUVs. The protease and/or proteinase may be added at a temperature low enough to ensure that the protease and/or proteinase is not in an activated state prior to or during cell encapsulation, e.g., about 0° C. to about 25° C., including about 1° C. to about 5° C., about 1° C. to about 10° C., about 1° C. to about 15° C., about 1° C. to about 20° C., or about 1° C. to about 25° C. In some embodiments, the protease and/or proteinase may be added at about 4° C. Subsequently, the temperature of the monodisperse single-emulsion droplets, multiple-emulsion droplets, and/or GUVs may be increased to a temperature sufficient to ensure activation of the protease and/or proteinase, e.g., 37-80° C., such as 30-50° C., 37-55° C., 40-60° C., 50-60° C., 60-70° C., or 70-80° C., to facilitate proteinase K activation and cell lysis. The proteinase K incubation may be for a time sufficient to result in cell lysis, e.g., 15-60 min (or longer as appropriate), e.g., 15-20 minutes. The emulsion may then be broken, and the protease and/or proteinase, e.g., proteinase K, washed out as necessary. RNA from the lysed cells may be captured for subsequent sequencing using any suitable method and reagents in the monodisperse droplets, e.g., prior to breaking the emulsion. For example, functionalized RNA capture beads, such as Drop-seq beads commercially available from ChemGenes Corporation, may be encapsulated with the cells in the monodisperse droplets. In some embodiments, such functionalized RNA capture beads may be incorporated directly into the template particles. For example, functionalized RNA capture beads may be encapsulated into a suitable polymer (e.g., hydrogel) material, e.g., BAC polyacrylamide hydrogel using Bis(acryloyl)cystamine as a crosslinker for polyacrylamide bead synthesis.

Measuring Lengths of Nucleic Acids

The methods described herein can be used to measure the length distributions of nucleic acids in solution. This may be accomplished by designing probe sequences that anneal to the target nucleic acids at different regions of known distance along their lengths. The probes can then be mixed with the target nucleic acids and compartmentalized in monodisperse single-emulsion droplets, multiple-emulsion droplets, and/or GUVs. Each monodisperse single-emulsion droplet, multiple-emulsion droplets, and/or GUV may contain, for example, two primer and probe sets that signal the presence of two different regions on the target a known distance apart. This can be repeated for different combinations of probes such that different pairs probe different distances and different regions of the target. The samples can be subjected to amplification, analysis, and sorting, if desired. In the analysis, one will find that some monodisperse single-emulsion droplets, multiple-emulsion droplets, and/or GUVs undergo amplification only with one of the probes while others, for example, amplify with only the other probe. This suggests that in these single-emulsion droplets, multiple-emulsion droplets, and/or GUVs, one type contains the region just for one of the probes, while the other type contains the region of the other probe. In this population, there may also be single-emulsion droplets, multiple-emulsion droplets, and/or GUVs, that undergo amplification with both probes, indicating that the target nucleic acid therein contained both regions. In this same suspension will be a large number of single-emulsion droplets, multiple-emulsion droplets, and/or GUVs including a measurable fraction of each of the three types of droplets—in addition to ones that, of course, undergo no amplification and, thus, presumably, do not contain the targeted regions. This data can be used to infer the lengths of the nucleic acids in solution.

For example, if the nucleic acids in solution are largely intact as whole molecules, than the majority of droplets undergoing amplification will exhibit amplification with both probe and primer sets and will thus show a mixed signal. By contrast, if the nucleic acid targets are highly fragmented, most of the detection events will be one or the other probe, with only rare instances of both probes. Since the distances between the probes may be known, this allows one to estimate the lengths and fragmentation of the molecules in the solution. This process can be repeated with different probe sets targeting different regions and/or having different distances between them, to more fully characterize the fragmentation of the target nucleic acids.

Microfluidic Enrichment for Sequence Analysis (MESA) in Single-Emulsion Droplets, Multiple-Emulsion Droplets, and/or GUVs The methods described herein can be used to perform microfluidic enrichment for sequence analysis (MESA) of target nucleic acids. This is accomplished by using the method to encapsulate target nucleic acids in monodisperse single-emulsion droplets, multiple-emulsion droplets, and/or GUVs and perform amplification in those droplets, yielding fluorescent signals when the droplets contain a target sequence. These droplets can then be sorted, thereby enriching the nucleic acids in the sorted pool. The reaction may also be multiplexed, if desired, to differentiate between molecules that contain multiple, distinct subsequences. Amplification may also be used to amplify the sorted nucleic acids either prior to, simultaneous with, or post sorting, so as to enable sequencing.

A key advantage of this approach is that the region that is amplified in the droplets can be used simply as a "detection region"—the amplicons need not include the molecules that are subjected to sequencing. Instead, they signal when a target molecule is present in a droplet so that the whole molecule can be recovered for downstream analysis. This is powerful because it allows a large nucleic acid, even one that is far too large to be efficiently amplified, to be recovered for downstream analysis. For example, suppose that there exists a gene that is thought to be part of an important biological pathway, e.g., signaling cascade, in a microorganism that is as yet still undiscovered. The goal is to recover the genes encoding the proteins involved in this pathway so that they can be sequenced and studied. This cannot easily be accomplished using existing enrichment methods since the microbe, being unknown may not be specifically cultivable and, in addition, the pathway, being largely of unknown sequence, cannot be purified using hybridization probes, since sequences for the probes to hybridize to are not known aside from the individual gene, which may be too small to pull out the entire pathway. However, this can be accomplished using the MESA method as described herein.

In some embodiments, the nucleic acids from the target may be fragmented to a size large enough to encapsulate the entire pathway, such as, for example tens or hundreds of kilobases, or even megabases or longer fragments. If the pathway exists within a fragment, it may contain the known gene. The fragmented nucleic acids, most of which do not contain the target, are subjected to the techniques described herein resulting in monodisperse single-emulsion droplets, that, for the most part, do not contain a pathway and thus exhibit no amplification, while rare drops that do contain the pathway, undergo amplification. The positive droplets can then be recovered by, for example, FACS sorting double emulsions that are fluorescently bright. These can then be subjected to further manipulations such as, if necessary, specific and non-specific amplification, quantitation through digital or quantitative PCR, and DNA sequencing. A powerful advantage of MESA over other enrichment strategies is that it allows very large nucleic acids, even up to the size of an entire genome, to be detected and recovered based on a short, known sequence of only tens of hundreds of base pairs. Few other enrichment methodologies have the ability to enrich such large nucleic acid sequences out of a heterogeneous pool using such limited amounts of information about the sequence.

The method can also be used to identify the DNA sequences of individual genomes. In this embodiment, nucleic acids from a target can be fragmented and encapsulated in monodisperse single-emulsion droplets, multiple-emulsion droplets, and/or GUVs with PCR reagents and primers specific to the DNA sequence of interest. After amplification, the positive monodisperse single-emulsion droplets, multiple-emulsion droplets, and/or GUVs can be sorted into individual compartments, such as well plate arrays, using FACS or MACS. Individual compartments can then be subjected to further manipulation, such as either specific or non-specific amplification. The resulting amplicons can then be used to make libraries for next generation sequencing techniques, or as material used directly in Sanger sequencing. This technique would be useful, for example, in a method designed to identify genetic differences in a retroviral population, such as HIV, found in an individual patient.

As discussed above, methods described herein can be used for digital PCR and, related, microfluidic enrichment for sequencing analysis (MESA). In some embodiments, a sample including nucleic acids, viruses, cells, particles, etc., is partitioned in single or multiple emulsions as described herein. The droplets are collected into a reservoir, such as a PCR tube, and incubated under conditions suitable for amplification such as thermal cycling. Isothermal methods can also be used, such as MDA, MALBAC, LAMP, etc. A fluorescent reporter can be included in the droplets or added to the carrier phase to induce a difference in fluorescence between droplets containing the target nucleic acids and droplets which do not contain the target nucleic acids.

For example Sybr green can be added to the carrier phase such that it partitions into the single or multiple emulsion. Since Sybr becomes much more fluorescent in the presence of double stranded DNA, droplets that undergo amplification will be fluorescently brighter than those that do not. To quantitate the number of target molecules in the sample, the droplets can be subjected to flow cytometric analysis, or even fluorescence activated cell sorting (FACS).

As the droplets flow through the flow cytometer, information about their size and fluorescence can be recorded. In the instance that the target molecules are loaded at limiting dilution, some droplets will be detected as fluorescent, because they contained a target molecule, and others will be detected as dim, because they do not. The fraction of bright-to-dim droplets can be used, in accordance with a Poisson distribution to estimate the starting concentration of the target molecule in the original sample. By using a FACS to sort the droplets based on fluorescence, it is possible to recover the double emulsions that contain target molecules and, by breaking the double emulsions, to retrieve the target molecules. This can be used to screen large, heterogeneous populations of nucleic acids to selectively recover target sequences. The above method may also be performed using GUVs, where suitable, in place of multiple-emulsion droplets.

PCR Activated Cell Sorting (PACS) in Single-Emulsion Droplets, Multiple-Emulsion Droplets, and/or GUVs The MESA technology enables the enrichment of naked nucleic acids out of a solution, but a similar approach can be applied to nucleic acids contained within entities, such as within cells, viruses, spores, particles etc., wherein the process is largely the same. For example, the entities including the target nucleic acids can be encapsulated in monodisperse single-emulsion droplets, multiple-emulsion droplets, and/or GUVs, and subjected to conditions sufficient to amplify the target nucleic acids, as described above. The monodisperse single-emulsion droplets, multiple-emulsion droplets, and/or GUVs can then be sorted based on amplification, to recover entities that have the target.

An important consideration when applying this technique to biological entities, especially ones that have a membrane or protective shell, e.g., cells, is that the nucleic acids must be accessible to amplification reagents for specific detection to occur, which may necessitate specialized procedures. For example the entities can be encapsulated in the monodisperse single-emulsion droplets, multiple-emulsion droplets, and/or GUVs with agents that release nucleic acids, such as proteases, lysozyme, detergents, strong bases, etc. They may also be encapsulated in monodisperse single-emulsion droplets, multiple-emulsion droplets, and/or GUVs and then soaked in solution that contain the lysing agent, which may partition through the monodisperse single-emulsion droplets', multiple-emulsion droplets', and/or GUVs' shell to induce lysis. They may also be encapsulated for example in gel particles that can be soaked in lysing agent. Then, these gel particles which will contain the nucleic acids of the entities, can be encapsulated in the monodisperse single-emulsion droplets, multiple-emulsion droplets, and/or GUVs for the detection via amplification procedure. The gel can be selected such that, it does not inhibit the lysis or amplification reaction such as, for example, by ensuring that its pore size is sufficiently large so as to enable a reagent to diffuse through the gel while trapping nucleic acids, or by enabling it to melt upon heating of the monodisperse single-emulsion droplets, multiple-emulsion droplets, and/or GUVs, as when using agarose. The gel may also be functionalized, if desired, to attach desired cell compounds, such as RNA molecules that may otherwise leak out of the gels and be undetectable. Yet another procedure that can be implemented to enable access of synthesis reagents to target nucleic acids is to use electric current to lyse cells, viruses, particles, etc., as they are being encapsulated into the monodisperse single-emulsion droplets, multiple-emulsion droplets, and/or GUVs. This can be achieved by, for instance, flowing the cells through a channel in which an electric current flows, which can create pores in a cell membrane, for example, and facilitate cell lysis.

Live-Cell PCR Activated Cell Sorting (PACS)

The application of emulsion PCR and sorting to cells as described herein has included the lysis and, in most instances, death of the organism. However, by modifying the approach and using the methods described herein, it is also possible to recover live, intact cells. This can be accomplished by, for example, encapsulating living cells in monodisperse single-emulsion droplets, multiple-emulsion droplets and/or GUVs under conditions such that cell contents leak into the encapsulating monodisperse single-emulsion droplet, multiple-emulsion monodisperse droplet and/or GUV while maintaining the viability of the cell. This is possible by, for instance, flowing the cell through a channel in which an electric current also flows, which can induce pore formation in the cell membrane and allow cell lysate to leak out. When the cell passes out of this channel, its membrane may seal back up, while the lysate that leaked out still exists around the cell. For laminar flow conditions, this can be performed such that the lysate around the cell flows with the cell and is encapsulated in the same compartment, such as a monodisperse single-emulsion droplet, multiple-emulsion droplet and/or GUV. Reagents suitable for amplification of the cell nucleic acids or detection of other cellular components can also be included such that the lysate around the cell can interact with the reagents when in the droplet. The reaction can be designed such that a fluorescent signal is produced, enabling droplets that contain the target cell to be recovered via sorting, and allowing live recovery of the cells. This is a powerful use of the technology because it provides the benefits of PACS—the ability to differentiate between cells based on sequence biomarkers, such as molecules and RNA—while preserving cell life so that other reactions and analyses can be performed.

Mass Spectrometry Activated Cell Sorting (MS-ACS)

The methods described herein rely, in some embodiments, on the ability to compartmentalize reactions in monodisperse single-emulsion droplets, multiple-emulsion droplets, e.g., double emulsions, and/or GUVs, detect reaction products within the monodisperse single-emulsion droplets, multiple-emulsion droplets, and/or GUVs, and sort the droplets and/or GUVs to recover specific entities based on those products and perform suitable analyses. Many types of assays can be performed, such as enzymatic assays, e.g., PCR, to differentiate between different entities, such as cells and viruses. However, in some cases, enzymatic techniques may not be able to detect the analyte of interest. In these instances, other methods can be implemented, such as spectrographic methods. A very powerful detection method is mass spectrometry, because it is sensitive and general. However, a limitation of mass spectrometry is that it is a destructive technology, destroying the sample that it analyzes. If the goal is the recovery of information only, this may be acceptable, but in some instances it is desirable to additionally recover material from the system which, normally, would be destroyed by the mass spectrometer.

Using the methods described herein, mass spectrometry can be used to analyze a sample while still allowing recovery of the sample. For example, suppose that the objective is to identify cells expressing proteins involved in a pathway. The cells can be loaded into monodisperse single-emulsion droplets, multiple-emulsion droplets, e.g., double emulsions, and/or GUVs and cultured, so that there are many in each monodisperse single-emulsion droplet, multiple-emulsion droplet and/or GUV, and/or so that they are allowed to produce the products of the pathways, e.g., molecules, compounds, etc., which will fill the monodisperse single-emulsion droplet, multiple-emulsion droplet and/or GUV. The monodisperse single-emulsion droplets, multiple-emulsion droplets, and/or GUVs can then be flowed into a device that will split off a portion of the monodisperse single-emulsion droplets, multiple-emulsion droplets, and/or GUVs, capturing some of the material from the cells or cell secretions, which can be subjected to destructive mass spectrometry. The other portion can then be sorted. The mass spectrometer can be used to analyze the compounds in the sampled portion and this information can be used to determine how to sort the sister portion of the droplet. Using this method, it is possible to use very sensitive and general mass spectrometry to specifically sort cells, while allowing recover of whole cells or cell lysates.

Colony Growth and Lysis

The ability to encapsulate cells in monodisperse single-emulsion droplets, multiple-emulsion droplets, e.g., double emulsions, and/or GUVs, is valuable for culturing organisms, such as cells and viruses. For example, if cells are grown in a single, shared volume, competition between cells may result in certain cells taking over the population, such that they include the majority of cells after some culture time. By compartmentalizing the cells in monodisperse single-emulsion droplets, multiple-emulsion droplets, and/or GUVs and culturing them, competition can be controlled and/or mitigated. Moreover, the permeability of the monodisperse single-emulsion droplets, multiple-emulsion droplets, and/or GUVs can be set such that certain molecules are able to pass through while others are not. This allows, for example, signaling molecules or other molecules important for growth to pass freely through the monodisperse single-emulsion droplets, multiple-emulsion droplet and/or GUV shells, to better control culture conditions.

Multiplexing

In certain embodiments of the subject methods, multiple biomarkers may be detected and analyzed for a particular cell. Biomarkers detected may include, but are not limited to, one or more proteins, transcripts and/or genetic signatures in the cell's genome or combinations thereof. With standard fluorescence based detection, the number of biomarkers that can be simultaneously interrogated may be limited to the number of fluorescent dyes that can be independently visualized within each monodisperse single-emulsion droplet, multiple-emulsion droplet and/or GUV. In certain embodiments, the number of biomarkers that can be individually detected within a particular a monodisperse single-emulsion droplet, multiple-emulsion droplet and/or GUV can be increased. For example, this may be accomplished by segregation of dyes to different parts of a monodisperse single-emulsion droplet, multiple-emulsion droplet and/or GUV. In particular embodiments, beads (e.g. LUMINEX® beads) conjugated with dyes and probes (e.g., nucleic acid or antibody probes) may be encapsulated in a monodisperse single-emulsion droplet, multiple-emulsion droplet and/or GUV to increase the number of biomarkers analyzed. In another embodiment, fluorescence polarization may be used to achieve a greater number of detectable signals for different biomarkers for a single cell. For example, fluorescent dyes may be attached to various probes and a monodisperse single-emulsion droplet, multiple-emulsion droplet and/or GUV may be visualized under different polarization conditions. In this way, the same colored dye can be utilized to provide a signal for different probe targets for a single cell. The use of fixed and/or permeabilized cells (as discussed in greater detail below) also allows for increased levels of multiplexing. For example, labeled antibodies may be used to target protein targets localized to cellular components while labeled PCR and/or RT-PCR products are free within a monodisperse single-emulsion droplet, multiple-emulsion droplet and/or GUV. This allows for dyes of the same color to be used for antibodies and for amplicons produced by RT-PCR.

Digital Enzyme-Linked Immunosorbent Assay (ELISA)

In some embodiments, the disclosed methods and devices can be used to quantitate epitopes in a sample using a digital ELISA procedure. In some embodiments, for example, epitopes bound to a solid substrate, such as a planer substrate surface or the surfaces of beads, can be additionally bound with an affinity reagent labeled with an enzyme catalyst. The sample can be washed to remove unbound affinity reagents and enzymes. The labeled epitopes or a portion thereof can then be released in solution in a variety of ways. For ease, the enzyme catalyst may be bound to the affinity reagent through a bond that can be degraded chemically or with the application, for example, of heat or light. Alternatively, the interaction between the affinity reagent and the epitope can be broken, or the interaction between the epitope and the substrate can be broken. If the binding occurs on beads, then the beads can be suspended in solution after the washing step, thereby suspending the enzyme catalysts. The suspended enzyme catalysts can then be encapsulated in monodisperse single-emulsion droplets, multiple-emulsion droplets, e.g., double emulsions, and/or GUVs, with reagents sufficient to detect the enzyme catalyst, such as a substrate that the enzyme catalyst can convert into a fluorescent product. The monodisperse single-emulsion droplets, multiple-emulsion droplets, and/or GUVs can then be incubated under conditions suitable for catalysis, resulting in monodisperse single-emulsion droplets, multiple-emulsion droplets, and/or GUVs containing a large amount of reaction product when the catalyst is present and a low amount when it is not. The number of fluorescent monodisperse single-emulsion droplets, multiple-emulsion droplets, and/or GUVs can then be quantitated compared to the dim monodisperse single-emulsion droplets, multiple-emulsion droplets, and/or GUVs, providing a measure of the number of catalyst molecules present in the sample. This information can then be used to infer the concentration of epitopes in the original sample.

Using the multiplexing methods described herein, this can also be accomplished without the need to wash the sample after binding. For example, two antibodies detecting the same target can be introduced into the sample, each labeled with a different catalyst. The sample can then be encapsulated in monodisperse single-emulsion droplets, multiple-emulsion droplets, e.g., double emulsions, and/or GUVs. In the event that a target is present, it should be bound, in many instances, by both antibodies, as occurs in a typical "sandwich" ELISA, except in this case the molecules are free to diffuse in solution rather than being bound to a substrate. The results will be monodisperse single-emulsion droplets, multiple-emulsion droplets, and/or GUVs that, sometimes, contain just one of the antibodies or that contain both antibodies, which can be detected by monitoring the presence of the catalyst reactions in the droplets. Provided the dilutions are properly controlled so that most droplets are empty, it should be possible to ascribe the presence of both catalyst products to a target being present in the droplet, while the presence of just one of the catalyst products likely corresponds to an unbound antibody. By quantitating the fraction of double-positive droplets, it is possible to estimate the fraction of targets in solution without having to perform washing procedures.

Digital Oligo-Linked Immunosorbent Assay (dOLISA)

The methods described herein can be used for sensitive detection and absolute quantification of RNA molecules. Assay approaches of interest also include, but are not limited to, those described by Chang, et al., *J. Immuno. Methods.* 378(1-2), 102-15 (2012), the disclosure of which is incorporated herein by reference. This application is applied to extremely low concentrations of analytes and the binding characteristics can deviate from typical immunoassay or ELISA platforms. Theoretical analysis clarifies what performance metrics (detection sensitivity, assay speed, etc.) can be expected from a set of experimental parameters.

The method involves binding of target protein molecules to antibodies conjugated to a bead surface. The amount of bound proteins (capture efficiency) in equilibrium state is determined by the dissociation constant $K_D$, setting the upper bound for capture efficiency. The binding reaction is a dynamic process governed by the on and off rates ($k_{on}$ and $k_{off}$) and the time-dependent evolution of the system can be simulated by numerically solving the differential equation that describes the kinetics. Without the intention of being bound by any theory, the binding kinetics depends primarily on $k_{on}$ value while $K_D$ value has a negligible effect on it. The slow kinetics can be rescued if a higher concentration of antibodies can be provided for binding.

In some embodiments, $k_{on}$ rate dictates the required duration of incubation to achieve desired detection efficiency. In the case of dOLISA, the secondary antibody is conjugated with a DNA oligo. The ternary complex (Ab-Ligand-oligoAb) is encapsulated into 0.1-10 million droplets, e.g., monodisperse single-emulsion droplets, (5-50 pL each in volume) such that there are single DNA template molecules per droplet, droplet PCR amplification in the presence of a fluorogenic reagent is performed, and the fluorescent droplets are counted.

Core-Shell Microgel Formation Through PTE

Provided herein are methods of creating core-shell microgels using PTE. Such methods generally include combining a plurality of monodisperse template particles with a first fluid to provide a first mixture, wherein the first fluid comprises a plurality of target particles and a polymer component; combining the first mixture with a second fluid to provide a second mixture, wherein the second fluid is immiscible with the first fluid and the polymer component; and shearing the second mixture such that a plurality of the monodisperse template particles are encapsulated in a plurality of monodisperse droplets in the second fluid; thereby providing a plurality of monodisperse droplets comprising the first fluid, one of the monodisperse template particles surrounded by a shell of the polymer component, and one of the plurality of target particles.

The newly formed outer shell can be used to retain biological materials and reagents to broaden the range of applications for instant emulsion technology. In some embodiments, the shell may be formed after the shearing. In some embodiments, the shell of the polymer component may be solidified by incubating as a suitable temperature, e.g., at a temperature of about 0° C. to about 25° C., including about 1° C. to about 5° C., about 1° C. to about 10° C., about 1° C. to about 15° C., and about 1° C. to about 20° C. In some embodiments, an incubation temperature of 4° C. is used.

Such methods may be combined with targeted analysis through affinity-based particle-templated emulsification as described herein. For example, in some embodiments, the monodisperse template particles are functionalized with capture agents, e.g., antibodies or nucleic acid capture reagents, e.g., oligos.

Sorting

In practicing the methods as described herein, one or more sorting steps may be employed. Sorting approaches of interest include, but are not necessarily limited to, approaches that involve the use of membrane valves, bifurcating channels, surface acoustic waves, selective coalescence, dielectrophoretic deflection, flow control, and/or other stimulus used to selectively deflect monodisperse droplets. Sorting approaches of interest further include those described by Agresti, et al., PNAS vol. 107, no 9, 4004-4009; the disclosure of which is incorporated herein by reference. A population may be enriched by sorting, in that a population containing a mix of members having or not having a desired property may be enriched by removing those members that do not have the desired property, thereby producing an enriched population having the desired property.

Sorting may be applied before or after any of the steps described herein. Moreover, two or more sorting steps may be applied to droplets, e.g., monodisperse droplets and/or GUVs, e.g., about 2 or more sorting steps, about 3 or more, about 4 or more, or about 5 or more, etc. When a plurality of sorting steps is applied, the steps may be substantially identical or different in one or more ways (e.g., sorting based upon a different property, sorting using a different technique, and the like).

Droplets, including monodisperse droplets prepared as described herein, may be sorted based on one or more properties. Properties of interest include, but are not limited to, the size, viscosity, mass, buoyancy, surface tension, electrical conductivity, charge, magnetism, fluorescence, and/or presence or absence of one or more components. In certain aspects, sorting may be based at least in part upon the presence or absence of a cell in the monodisperse droplet. In certain aspects, sorting may be based at least in part based upon the detection of the presence or absence of nucleic acid amplification products such as amplification or synthesis products, e.g., as indicated by the detection of a fluorescent amplification product; or indicated by the detection of a surface antigen of an amplification product.

Monodisperse droplet sorting may be employed, for example, to remove monodisperse droplets in which no cells are present. Encapsulation may result in one or more monodisperse droplets, including a majority of the monodisperse droplets, in which no cell is present. If such empty monodisperse droplets were left in the system, they would be processed as any other monodisperse droplet, during which reagents and time would be wasted. To achieve the highest speed and efficiency, these empty monodisperse droplets may be removed with monodisperse droplets sorting. For example, a drop maker may operate close to the dripping-to-jetting transition such that, in the absence of a cell, 8 μm drops are formed; by contrast, when a cell is present the disturbance created in the flow will trigger the breakup of the jet, forming drops 25 μm in diameter. The device may thus produce a bi-disperse population of empty 8 μm drops and single-cell containing 25 μm drops, which may then be sorted by size using, e.g., a hydrodynamic sorter to recover only the larger, single-cell containing drops.

Passive sorters of interest include hydrodynamic sorters, which sort monodisperse droplets into different channels according to size, based on the different ways in which small and large monodisperse droplets travel through the microfluidic channels. Also of interest are bulk sorters, a simple example of which is a tube containing monodisperse droplets of different mass in a gravitational field. By centrifuging, agitating, and/or shaking the tube, lighter monodisperse droplets that are more buoyant will naturally migrate to the top of the container. Monodisperse droplets that have magnetic properties could be sorted in a similar process, except by applying a magnetic field to the container, towards which monodisperse droplets with magnetic properties will naturally migrate according to the magnitude of those properties. A passive sorter as used in the subject methods may also involve relatively large channels that will sort large numbers of monodisperse droplets simultaneously based on their flow properties.

Picoinjection can also be used to change the electrical properties of monodisperse droplets. This could be used, for example, to change the conductivity of the monodisperse droplets by adding ions, which could then be used to sort them, for example, using dielectrophoresis. Alternatively, picoinjection can also be used to charge the monodisperse droplets. This could be achieved by injecting a fluid into the monodisperse droplets that is charged, so that after injection, the monodisperse droplets would be charged. This would produce a collection of monodisperse droplets in which some were charged and others not, and the charged monodisperse droplets could then be extracted by flowing them through a region of electric field, which will deflect them based on their charge amount. By injecting different amounts of liquid by modulating the piocoinjection, or by modulating the voltage to inject different charges for affixed injection volume, the final charge on the monodisperse droplets could be adjusted, to produce monodisperse droplets with a different charge. These would then be deflected by different amounts in the electric field region, allowing them to be sorted into different containers.

Flow cytometry (FC) may be utilized as an alternative to on-chip monodisperse droplet sorting in any of the methods described herein. Such a method, along with devices which may be utilized in the practice of the method, are described in Lim and Abate, *Lab Chip,* 2013, 13, 4563-4572; the disclosure of which is incorporated herein by reference in its entirety and for all purposes. Briefly, monodisperse droplets may be formed and manipulated, e.g., using techniques like splitting and picoinjection as described herein, resulting in single emulsions. These single emulsions may then be double emulsified, e.g., to provide multiple-emulsion droplets and/or GUVs as described herein, e.g., using one or more devices as described herein or in Lim and Abate, *Lab Chip,* 2013, 13, 4563-4572. The double emulsions may then be analyzed via FC, e.g., FACS.

Droplets, e.g., monodisperse single-emulsion droplets or double-emulsion droplets, and/or GUVs, generated using the methods as described herein can be used to conduct a variety of encapsulated chemical and biological reactions including, for example, reactions involving enzymes, such as PCR. In many instances, the result of the reaction may be a product that may be of interest to detect. In addition, it may be of interest to recover monodisperse single-emulsion droplets, multiple-emulsion droplets and/or GUVs that have different levels of the product, or a combination of multiple products. This can be accomplished using the invention in a variety of ways. For example, reactions can be partitioned into the monodisperse single-emulsion droplet, multiple-emulsion droplet and/or GUV reactors such that different monodisperse single-emulsion droplets, multiple-emulsion droplets and/or GUVs react to different levels and have different final product concentrations. The monodisperse single-emulsion droplets, multiple-emulsion droplets and/or GUVs can then be interrogated using, for example, spectrographic techniques, such as optical or fluorescent imaging, flow cytometry, Raman spectroscopy, mass-spectrometry, etc. These methods, or combinations thereof, can be used to determine the concentrations of different compounds in the monodisperse single-emulsion droplets, multiple-emulsion droplets and/or GUVs. These methods can be combined with a mechanism for sorting monodisperse single-emulsion droplets, multiple-emulsion droplets and/or GUVs using, for example, microfluidic based sorting or flow cytometry in the case of double emulsions. The contents of the positively and negatively sorted monodisperse single-emulsion droplets, multiple-emulsion droplets and/or GUVs can be analyzed to identify different properties of these sorted pools.

Additionally, in some instances, it may be desirable to load individual positively sorted droplets into isolated wells for further study enabling, for example, additional, detailed individual analysis of each positively sorted droplet. As a non-limiting example, the methods and devices as described herein can be used to interrogate viruses containing a specific nucleic acid sequence. Viruses from a heterogeneous population can, for example, be loaded into monodisperse single-emulsion droplets, multiple-emulsion droplets, e.g., double emulsions, and/or GUVs with reagents sufficient for lysis and amplification of target nucleic acids. The monodisperse single-emulsion droplets, multiple-emulsion droplets and/or GUVs can then be analyzed and sorted, e.g., with flow cytometry for double emulsions, to detect and recover all droplets that underwent amplification of the target nucleic acids. These droplets can be sorted into a single positive pool or sorted individually into wells on a well plate array, for example. They may even be loaded in specific groups, if desired, so that each well on the array has a desired combination of positive events, which may all be the same or exhibit different amplification targets. The sorted droplets can then be subjected to additional analysis such as, for example, mass spectrometry or next generation sequencing.

In the pooled analysis case, the nucleic acids from all cells loaded into the positive container will be mixed together and analyzed as a whole. However, by loading single droplets into wells, the contents of each well can be analyzed individually such as, for example, by barcoding the nucleic acids in each well before pooling and sequencing. This permits, for example, the lysis of single viral genomes of the target species to not only detect the target species but recover individual genomes so that comparisons between different members of the same species can be obtained. Such an analysis is useful for a variety of applications such as metagenomics or for studying viral diversity.

In some embodiments of the invention, it is desirable to amplify the target molecules in addition to the amplification that is used for detection to enable, for example, additional analyses on sorted target nucleic acids. For example, in some applications, the target will include nucleic acids desirable for sequencing, but the quantity of nucleic acids provided by the target will be too small to enable sequencing. In these instances, an amplification procedure, such as a specific PCR and/or non-specific multiple displacement amplification can be applied, before or after sorting of the monodisperse single-emulsion droplets, multiple-emulsion droplets and/or GUVs. For example, in the case of a virus with a relatively small, linear genome, such as polio or HIV, a PCR can be performed prior to or post sorting to provide sufficient copies of each genome after sorting to enable sequencing analysis. For example individual genomes may be encapsulated in droplets and subjected to amplification of the whole or a portion of the genome. Simultaneous with or following this reaction, an additional amplification can be performed to identify the genome in the monodisperse single-emulsion droplets, multiple-emulsion droplets and/or GUVs, and the monodisperse single-emulsion droplets, multiple-emulsion droplets and/or GUVs sorted based on this information. These sorted single or multiple emulsions, now containing a large number of copies of the target nucleic acid, may then be more easily subjected to follow-on analyses.

Alternatively, individual genomes can be encapsulated and subjected to the detection amplification such that, for instance, each positive monodisperse single-emulsion droplets, multiple-emulsion monodisperse droplet and/or GUV contains just one copy of the full length target nucleic acid and a large number of the small detection region amplicons. Based on these amplicons, the monodisperse single-emulsion droplets, multiple-emulsion droplets and/or GUVs can be recovered as a pool, providing for each positive sorting event one full length copy of the target genome. To prepare a sequencing library, these positive genomes can then be amplified using a PCR that is specific and has primers that flank the regions desired or, alternatively, a non-specific method to amplify the entirety of the genome, such as multiple displacement amplification (MDA) or multiple annealing and looping based amplification cycles (MALBAC). In addition, if the positive monodisperse single-emulsion droplets, multiple-emulsion droplets and/or GUVs are not pooled, for example, if the positive monodisperse single-emulsion droplets, multiple-emulsion droplets and/or GUVs are sorted into a well plate array, and then subjected to amplification using a PCR that is specific and has primers that flank the region desired, the resulting individual amplicons can be used directly as material for Sanger sequencing.

A powerful advantage of the disclosed methods and devices is its ability to perform a large number of independent, isolated reactions and then apply a variety of spectrographic techniques to detect reaction products and sort to recover specific reactors that underwent a desired reaction. A challenge that may arise in the performance of the disclosed methods is that, in some instances, positive events that are desired for further analysis might be very rare. For example, if the disclosed methods are used to detect a specific virus in a large, diverse pool of viruses, in which the desired virus is present at a very low level, then a large number of individual viruses might need to be analyzed in order to recover the specific virus. And, if it is desirable to recover multiple instances of the species, then an even larger number of total viruses might need to be analyzed. Since the number of reactions that can be performed and sorted with the disclosed methods is finite, there may be instances in which the target is too rare to detect reliably.

In certain instances, the methods as described herein can be used in a tiered sorting process to recover extremely rare events, each sorting round providing an enrichment factor. By performing the sorting on the sample repeatedly, the sample can be enriched for targets so that the total enrichment becomes the multiplicative product of all of the individual enrichments. For example, suppose that a system as described herein is capable of generating, analyzing, and sorting at most 1 million monodisperse single-emulsion droplets, multiple-emulsion droplets and/or GUVs. Under ideal conditions, this means that an event that is present at, for example, 1 in a billion is unlikely to be detected with a straightforward usage of the system. However, by performing tiered sorting and enriching the target at each sorting round, such rare events can be recovered.

For example, in a first round, 10 billion entities for testing can be isolated in the million monodisperse single-emulsion droplets, multiple-emulsion droplets and/or GUVs such that each droplet and/or GUV contains about 10,000 entities. If the target entity is present at 1 in 1 billion, then in such a sample there will be at most 10 monodisperse single-emulsion droplets, multiple-emulsion droplets and/or GUVs that contain the target and are thus positive. These will be sorted, each providing 10,000 entities, yielding a total number of 100,000 entities in which the 10 desired are mixed. In some instances, this enrichment may be sufficient, but in others, it may be desirable to enrich further, even to 100% purity. In this case, the tiered sorting approach can be used, loading the 100,000 entities into 1 million droplets such that, for example, 1 in 10 droplets contains 1 entity, loading in accordance with a Poisson distribution. In this instance, the majority of droplets that are determined to be positive for the target will contain only that target entity, although due to the random nature of Poisson loading, some will also contain negative off-target entities that happened to be co-encapsulated with a positive.

When the 1 million droplets are analyzed and sorted, 10 will again be determined to contain the target entity and will be recovered with sorting, providing a highly enriched population that is almost completely pure for the target. To enrich further, additional round of sorting can be performed.

The power of tiered sorting is that in this instance the final enrichment is the multiplicative product of the individual enrichments. For example, if the method is able to enrich a maximum of 10^3 in one round, then by performing the sorting twice on the same sample the final enrichment will become 10^3×10^3=10^6, while another round will provide a final enrichment of, for example, 10^9. Additionally, the enrichments can be similar in each round or different, depending on the desires of the user. For example, a first round with a small number of relations can be used to provide an enrichment of, for instance, 10^3, and then a more intensive round can be used to perform an enrichment of 10^6, yielding again a 10^9 final enrichment. These values can be adjusted as needed to optimize for the particular application but the tiered sorting methods generally provide the very powerful advantage of being able to enrich extremely rare events out of massive populations even with finite enrichment power.

When using the disclosed methods to enrich with PCR activated sorting, special considerations may need to be taken to ensure that each enrichment is successful and increases the concentration of the target in the solution. For example, if the goal is to detect a very rare virus in a large population, then in the first round, amplification primers can be generated against a specific sequence in the viral genome. These will yield many copies of that region which will be collected into the sorted chamber. If this same region is used in additional sorting rounds, then the product amplicons of earlier rounds will be detected and sorted, leading to a large number of positive events that will erode the power of the method for achieving large enrichments. In this instance, the primers in later rounds can be modified so as to not detect amplification products from earlier rounds. This can be achieved in a number of ways including, for example, using a nested PCR approach in which the primers in later rounds amplify from beyond the region that is used in the early rounds so that products from early rounds cannot be amplified in later rounds. Alternatively, completely distinct regions can be targeted in later rounds, such as different portions of the same gene or different genes altogether. Combinations of these methods can also be used to achieve highly enriched samples.

Suitable Subjects and/or Samples

The subject methods may be applied to biological samples taken from a variety of different subjects. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects (that is, in "non-human subjects") such as, but not limited to, birds, mice, rats, dogs, cats, livestock and horses. Accordingly, it is to be understood that any subject in need of assessment as described herein is suitable.

Moreover, suitable subjects include those who have and those who have not been diagnosed with a condition, such as cancer. Suitable subjects include those that are and are not displaying clinical presentations of one or more cancers. In certain aspects, a subject may one that may be at risk of developing cancer, due to one or more factors such as family history, chemical and/or environmental exposure, genetic mutation(s) (e.g., BRCA1 and/or BRCA2 mutation), hormones, infectious agents, radiation exposure, lifestyle (e.g., diet and/or smoking), presence of one or more other disease conditions, and the like.

As described more fully above, a variety of different types of biological samples may be obtained from such subjects. In certain embodiments, whole blood is extracted from a subject. When desired, whole blood may be treated prior to practicing the subject methods, such as by centrifugation, fractionation, purification, and the like. The volume of the whole blood sample that is extracted from a subject may be 100 mL or less, e.g., about 100 mL or less, about 50 mL or less, about 30 mL or less, about 15 mL or less, about 10 mL or less, about 5 mL or less, or about 1 mL or less.

The subject methods and devices as described herein are compatible with both fixed and live cells. In certain embodiments, the subject methods and devices are practiced with live cells. In other embodiments, the subject methods and devices are practiced with fixed cells. Fixing a cellular sample allows for the sample to be washed to extract small molecules and lipids that may interfere with downstream analysis. Further, fixing and permeabilizing cells allows the cells to be stained with antibodies for surface proteins as well as intracellular proteins. Combined with the nucleic amplification methods as described herein, such staining can be used to achieve high levels of multiplexing because the antibodies are localized to the cell sample, while the nucleic amplification products are free within a monodisperse single-emulsion droplet, multiple-emulsion monodisperse droplet, and/or GUV. Such a configuration allows for dyes of the same color to be used for antibodies and for amplicons produced by nucleic acid amplification. Any suitable method can be used to fix cells, including but not limited to, fixing using formaldehyde, methanol and/or acetone.

Detecting Proteins or DNA with Enzyme-Linked Probes

The methods and devices as described herein can be used in a variety of ways for detecting and sorting entities in a heterogeneous solution. Some embodiments described thus far accomplish this using nucleic acid amplification performed in monodisperse single-emulsion droplets or multiple-emulsion droplets, e.g., double emulsions, and/or GUVs, but other methods are also enabled as described herein. When the disclosed methods and devices are used to detect nucleic acids, this can be accomplished by, for example, encapsulating individual nucleic acid entities in the monodisperse single-emulsion droplets, multiple-emulsion droplets and/or GUVs and then subjecting them to amplification with primers specific for target nucleic acids, detecting the target amplicons, and then sorting based on amplification. However, other detectable signals can be generated using other means, such as by binding affinity reagents to the targets. For example, if the target is a nucleic acid, probes specific to the target can be synthesized that can hybridize to the target when present; these probes may be labeled with dyes or, in some cases, catalysts, such as enzyme based or non-enzyme based catalysts. The targets, now bound by their probes, can be subjected to purification to remove unbound probes and, the remaining material can be encapsulated in the droplets and/or GUVs using the methods as described herein.

In the case of a catalyst-linked probe, the substrate for the catalyst may also be included in the monodisperse single-emulsion droplets or multiple-emulsion droplets and/or GUVs. In this instance, monodisperse single emulsions or multiple emulsions that contain targets will be bound with probes and, thus, will include catalysts, resulting in catalysis of the substrate and the generation of a product, which may, for example, be fluorescent. Over time, this will cause the monodisperse single-emulsion droplets or multiple-emulsion droplets and/or GUVs to fill with fluorescent product. By contrast, monodisperse single-emulsion droplets or multiple-emulsion droplets and/or GUVs that are empty or that contain off-target molecules will not contain catalysts, resulting in no product generation and, hence no detectable signal. The result of such an approach is a large collection of monodisperse single-emulsion droplets or multiple-emulsion droplets and/or GUVs, some of which are fluorescent and others dim, enabling recovery of the targets by sorting the encapsulating fluorescent monodisperse single-emulsion droplets or multiple-emulsion droplets and/or GUVs. This procedure can also be applied to other kinds of targets, such as biomolecules, viruses, cells, etc., that can be bound with affinity reagents, such as antibodies. In this case, affinity reagents would, for example, be bound with a catalyst, and the procedure would be performed as described above for nucleic acid targets bound by nucleic acid probes.

In both of these examples, washing may be implemented to remove unbound catalysts, which would otherwise be encapsulated in monodisperse single-emulsion droplets or multiple-emulsion droplets and/or GUVs and yield false positives. However, if washing to remove unbound catalysts is not desirable or possible, then an alternative approach would be to use a multiplexed assay in which, for example, the localization of two signals is used to identify a positive event. For example, if the goal is to detect a nucleic acid target that is in a solution, the probes for two different sequences on the target can be synthesized, each bound with a different catalyst that performs, for example, a reaction that yields a fluorescent product. In one embodiment, the fluorescent products for the distinct catalysts can be different colors, for example one yielding a green fluorescent product and the other a red fluorescent product. The probes can be bound to the targets, as normal. In this instance, while there will be many unbound probes in solution, in the majority of instances, the probes corresponding to the first type of catalyst will not be physical bound to the second probe with a different catalyst unless they are both bound to the same target nucleic acid.

The solutions can also be diluted as necessary to perform the hybridization at a high concentration. The concentration can then be reduced such that any given droplet-equivalent volume of solution will contain just one probe or a target with both bound probes. This solution can then be encapsulated with the substrates for the catalysts, incubated, detected, and sorted. In this embodiment, many monodisperse single-emulsion droplets or multiple-emulsion droplets and/or GUVs will contain just a red or green catalyst, but others will contain both a red and a green—the ones that are bound to the target. This will allow droplets containing the target nucleic acid to be differentiated from those that just contain catalysts by detecting the droplets that emit fluorescence at both wavelengths, without the need to wash.

Again, a false positive may occur when unbound probes of both catalysts happen to be co-encapsulated in the same droplet, but this can be mitigated by diluting the solution sufficiently to ensure that this event is substantially rarer than the presence of the targets, so that the double-positive monodisperse single-emulsion droplets or multiple-emulsion droplets and/or GUVs identified can most often be associated with the presence of a target. Similar techniques can be applied to other kinds of targets like cells or proteins using different kinds of affinity reagents, such as binding molecules like antibodies, which can again be bound with catalysts of different reactivity, etc.

Detecting Cancer

Methods as described herein also involve methods for detecting cancer. Such methods may include encapsulating in a monodisperse single-emulsion droplet, multiple-emulsion droplet and/or GUV oligonucleotides obtained from a biological sample from the subject, wherein at least one oligonucleotide is present in the monodisperse single-emulsion droplet, multiple-emulsion droplet and/or GUV; introducing polymerase chain reaction (PCR) reagents, a detection component, and a plurality of PCR primers into the monodisperse single-emulsion droplet, multiple-emulsion droplet and/or GUV and incubating the monodisperse single-emulsion droplet, multiple-emulsion droplet and/or GUV under conditions allowing for PCR amplification to produce PCR amplification products, wherein the plurality of PCR primers include one or more primers that each hybridize to one or more oncogenes; and detecting the presence or absence of the PCR amplification products by detection of the detection component, wherein detection of the detection component indicates the presence of the PCR amplification products.

Detection of one or more PCR amplification products corresponding to one or more oncogenes may be indicative that the subject has cancer. The specific oncogenes that are added to the droplet may vary. In certain aspects, the oncogene(s) may be specific for a particular type of cancer, e.g., breast cancer, colon cancer, and the like.

Moreover, in practicing the subject methods the biological sample from which the components are to be detected may vary, and may be based at least in part on the particular type of cancer for which detection is sought. For instance, breast tissue may be used as the biological sample in certain instances, if it is desired to determine whether the subject has breast cancer, and the like. In practicing the methods for detecting cancer, any variants to the general steps described herein, such as the number of primers that may be added, the manner in which reagents are added, suitable subjects, and the like, may be made. The above method may also be performed using single-emulsion droplets in place of multiple-emulsion droplets.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-73 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method for generating a monodisperse emulsion, the method comprising:
    combining a plurality of monodisperse template particles with a first fluid to provide a first mixture, wherein the first fluid comprises a plurality of target particles;
    combining the first mixture with a second fluid to provide a second mixture, wherein the second fluid is immiscible with the first fluid; and
    shearing the second mixture such that a plurality of the monodisperse template particles are encapsulated in a plurality of monodisperse droplets in the second fluid, thereby providing a plurality of monodisperse droplets comprising the first fluid, one of the monodisperse template particles, and one of the plurality of target particles.

2. The method of 1, wherein combining the plurality of monodisperse template particles with the first fluid to provide the first mixture comprises causing a portion of the first fluid to be absorbed by the monodisperse template particles.

3. The method of 1, comprising removing excess first fluid from the first mixture after causing the portion of the first fluid to be absorbed by the monodisperse template particles.

4. The method of 1, wherein combining the plurality of monodisperse template particles with the first fluid to provide the first mixture comprises flowing a portion of the first fluid into the monodisperse template particles.

5. The method of any one of 1-4, wherein the monodisperse template particles comprise a hydrogel.

6. The method of 5, wherein the hydrogel is selected from agarose, a polyethylene glycol (PEG), a polyacrylamide (PAA), and combinations thereof.

7. The method of any one of 1-6, wherein the first fluid comprises an aqueous phase fluid.

8. The method of any one of 1-7, wherein the second fluid comprises an oil.

9. The method of 8, wherein the oil comprises a fluorocarbon oil, a hydrocarbon oil, or a combination thereof 10. The method of any one of 1-9, wherein the second fluid comprises a surfactant soluble in the second fluid.

11. The method of any one of 1-10, wherein the first fluid comprises a surfactant soluble in the first fluid.

12. The method of 11, wherein the surfactant soluble in the first fluid comprises octylphenol ethoxylate and/or octylphenoxypolyethoxyethanol.

13. The method of any one of 1-12, wherein the method does not utilize microfluidics.

14. The method of any one of 1-13, wherein, after shearing, the second fluid comprises a plurality of droplets that do not comprise one of the monodisperse template particles.

15. The method of 14, comprising enriching for monodisperse droplets comprising monodisperse template particles relative to droplets that do not comprise one of the monodisperse template particles.

16. The method of 15, wherein one or more droplets that do not comprise one of the monodisperse template particles are removed from the monodisperse emulsion by filtration or centrifugation.

17. The method of any one of 14-16, wherein the monodisperse droplets have an average diameter and the plurality of droplets that do not comprise one of the monodisperse template particles have an average diameter which is smaller than the average diameter of the monodisperse template particles.

18. The method of any one of 1-17, wherein the shearing comprises flowing the second mixture through a pipette tip, shaking the second mixture with a homogenizer, or shaking the second mixture with a bead beater.

19. The method of any one of 1-18, comprising swelling the monodisperse template particles encapsulated in the monodisperse droplets.

20. The method of any one of 1-19, wherein the target particles are DNA molecules.

21. The method of 20, wherein the DNA molecules are genomic DNA molecules.

22. The method of any one of 1-19, wherein the target particles are RNA molecules.

23. The method of any one of 1-22, wherein the target particles are cells.

24. The method of 23, wherein the monodisperse droplets comprise one or more cells per droplet.

25. The method of 23, wherein the monodisperse droplets do not comprise more than one cell per droplet.

26. The method of any one of 1-25, further comprising incorporating a cell lysis reagent into the monodisperse droplets.

27. The method of 26, wherein the cell lysis reagent is present in the first mixture prior to encapsulation of the plurality of the monodisperse template particles in the plurality of monodisperse droplets.

28. The method of 26 or 27, wherein the cell lysis reagent does not comprise a detergent.

29. The method of any one of 26-28, wherein the cell lysis reagent comprises proteinase K.

30. The method of any one of 1-29, further comprising sorting the monodisperse droplets.

31. The method of 30, wherein the sorting is performed by dielectrophoretic deflection, selective coalescence, fluorescence activated cell sorting (FACS), electrophoresis, acoustic separation, magnetic activated cell sorting (MACS), flow control, or other stimulus used to selectively deflect monodisperse droplets.

32. The method of any one of 1-31, wherein the target particles are nucleic acids and wherein the first fluid comprising the plurality of target particles further comprises nucleic acid synthesis reagents, and wherein the nucleic acid synthesis reagents are encapsulated in the monodisperse droplets.

33. The method of 32, comprising subjecting one or more of the monodisperse droplets comprising the first fluid and one or more of the plurality of target particles to nucleic acid synthesis conditions.

34. The method of 32, wherein the nucleic acid synthesis reagents comprise nucleic acid amplification reagents.

35. The method of any one of 1-34, comprising subjecting one or more of the monodisperse droplets comprising the first fluid and one or more of the plurality of target particles to nucleic acid amplification conditions.

36. The method of any one of 1-34, comprising isolating nucleic acids from one or more of the plurality of monodisperse droplets.

37. The method of 36, comprising isolating nucleic acid synthesis and/or amplification products from one or more of the plurality of monodisperse droplets.

38. The method of any one of 1-37, comprising sequencing nucleic acids and/or nucleic acid synthesis and/or amplification products isolated from one or more of the plurality of monodisperse droplets.

39. The method of 34, wherein the nucleic acid amplification reagents comprise Polymerase Chain Reaction (PCR) reagents or Multiple Displacement Amplification (MDA) reagents, and the nucleic acid amplification conditions comprise PCR conditions or MDA conditions, respectively.

40. The method of 34, wherein the nucleic acid amplification reagents comprise isothermal nucleic acid amplification reagents and the nucleic acid amplification conditions comprise isothermal nucleic acid amplification conditions.

41. The method of any one of 1-40, wherein the first fluid comprising the plurality of target particles comprises nucleic acid detection reagents, which are encapsulated in the monodisperse droplets.

42. The method of 41, comprising detecting one or more of the target particles, a portion thereof, a nucleic acid synthesis product thereof, and/or a nucleic acid amplification product thereof by detecting one or more of the detection reagents.

43. The method of any one of 1-42, comprising attaching one or more of the target particles, the nucleic acid synthesis reagents, and the nucleic acid detection reagents to one or more of the monodisperse template particles.

44. The method of 43, wherein one or more of the target particles, the nucleic acid synthesis reagents, and the nucleic acid detection reagents are attached to the monodisperse template particles via one or more tethering moieties positioned on or in the monodisperse template particles.

45. The method of 44, wherein the one or more tethering moieties are oligonucleotides which are bound on or in the monodisperse template particles.

46. The method of 44, wherein the one or more tethering moieties are functionalized beads which are encapsulated in the monodisperse template particles.

47. The method of any one of 1-46, wherein each of the monodisperse droplets comprise a separate compartment containing a reagent.

48. The method of 47, comprising releasing the reagent from the separate compartment.

49. The method of any one of 1-48, wherein the monodisperse template particles have an average volume, and wherein the method comprises shrinking the monodisperse template particles to decrease the average volume.

50. The method of any one of 1-49, wherein the monodisperse template particles are a first type of particle, and wherein the method comprises encapsulating one or more of a second type of particle in a droplet with one or more of the first type of particle.

51. The method of any one of 1-50, comprising removing excess second fluid from the second mixture following the shearing of the second mixture.

52. The method of 51, wherein removing excess second fluid from the second mixture comprises centrifuging the mixture and removing the supernatant.

53. The method of any one of 1-52, comprising combining a third fluid with the second mixture, following the shearing of the second mixture, to produce a third mixture, wherein the third fluid is immiscible with the second fluid.

54. The method of any one of 1-52, comprising combining a third fluid with the second mixture, following the shearing of the second mixture, to produce a third mixture, wherein the third fluid is immiscible with the first and second fluids.

55. The method of 53, wherein the third fluid comprises an aqueous phase fluid.

56. The method of 49 or 54, wherein the third fluid comprises an oil.

57. The method of any one of 53-56, wherein the third fluid comprises a surfactant soluble in the third fluid.

58. The method of any one of 53-57, comprising shearing the third mixture to encapsulate the monodisperse template particles in double-emulsion droplets in the third fluid.

59. The method of any one of 53-53, comprising shearing the third mixture to encapsulate one or more of the monodisperse droplets, with or without the monodisperse template particles, in one or more droplets in the third fluid to provide one or more double-emulsion droplets.

60. The method of any one of 53-59, wherein the third fluid comprises a gelling agent.

61. The method of any one of 1-60, wherein 75% or more of the monodisperse droplets comprise one, and not more than one, monodisperse template particle.

62. The method of any one of 1-60, wherein 85% or more of the monodisperse droplets comprise one, and not more than one, monodisperse template particle.

63. The method of any one of 1-60, wherein 95% or more of the monodisperse droplets comprise one, and not more than one, monodisperse template particle.

64. The method of any one of 1-62, wherein 75% or more of the monodisperse template particles are encapsulated in monodisperse droplets in the second fluid.

65. The method of any one of 1-62, wherein 90% or more of the monodisperse template particles are encapsulated in monodisperse droplets in the second fluid.

66. The method of any one of 1-65, wherein the monodisperse template particles comprise a lipophilic polymer.

67. A method, comprising:

combining a plurality of monodisperse template particles with a first fluid to provide a first mixture, wherein the first fluid comprises a plurality of cells and a cell-lysis reagent;

combining the first mixture with a second fluid to provide a second mixture, wherein the second fluid is immiscible with the first fluid;

shearing the second mixture such that a plurality of the monodisperse template particles are encapsulated in a plurality of monodisperse droplets in the second fluid, thereby providing a plurality of monodisperse droplets comprising the first fluid, one of the monodisperse template particles, the cell-lysis reagent, and one of the plurality of cells;

maintaining the cell-lysis reagent at a temperature sufficient to prevent activation of the cell lysis reagent until after the plurality of monodisperse droplets are provided; and following the provision of the plurality of monodisperse droplets, incubating the plurality of monodisperse droplets at a temperature sufficient for activation of the cell-lysis reagent and lysis of the one of the plurality of cells.

68. The method of 67, wherein the cell-lysis reagent comprises proteinase K.

69. The method of 67 or 68, wherein the cell-lysis reagent does not comprise a detergent.

70. The method of any one of 67-69, comprising rupturing the plurality of monodisperse droplets.

71. The method of any one of 67-70, wherein the first fluid comprises a plurality of RNA-capture beads.

72. The method of any one of 67-70, wherein the monodisperse template particles comprise one or more RNA-capture beads incorporated therein.

73. The method of 71 or 72, comprising sequencing RNA molecules captured by the RNA-capture beads.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

The following materials and methods generally apply to the results presented in the Examples described herein except where noted otherwise.

Monodisperse Hydrogel Particle Preparation

Monodisperse polyacrylamide (PAA) particles were generated using 6.2% acrylamide (Sigma-Aldrich), 0.18% N,N'-Methylenebisacrylamide (Sigma-Aldrich) and 0.3% ammonium persulphate (Sigma-Aldrich). Polyethylene glycol (PEG) particles were generated using 14% (w/v) 8-arm PEGSH (Creative PEGworks) in 100 mM $NaHCO_3$ and PEGDA(6 kDA) (Creative PEGworks) in 100 mM $NaHCO_3$. Agarose particles were generated using 1% low melting temperature agarose (Sigma-Aldrich). Agarose suspension was warmed with a space heater during emulsification to prevent solidification. Agarose and PEG solutions were injected into a droplet maker device (FIG. 1) with oil (HFE-7500 fluorinated oil supplemented with 5% (w/w) deprotonated Krytox 157 FSH) using syringe pumps (New Era, NE-501). The PAA solution was injected into the droplet generation device with the fluorinated oil supplemented with 1% tetramethylethylenediamine (TEMED) The hydrogel solution and oil were loaded into separate 1-mL syringes (BD) and injected at 300 and 500 µl, respectively, into the droplet generation device using syringe pumps, controlled with a Python script, see example the website located by placing "https://" in front of "github.com/Abate-Lab/Pump-Control-Program". The PAA and PEG droplets were collected and incubated for 1 hour at room temperature for gelation. The agarose droplets were incubated on ice for gelation. After gelation, the gelled droplets were transferred to an aqueous carrier by destabilizing them in oil with addition of an equal volume of 20% (v/v) perfluoro-1-octanol in HFE-7500. The particles were washed twice with hexane containing 2% Span-80 (Sigma-Aldrich) to remove residual oil. Following the hexane wash, the particles were washed with sterile water until oil was removed. Droplets were imaged using the EVOS Cell Imaging System (Thermo Fisher). Images were taken under a 4× and 10× objective using EVOS FITC LED light sources.

Device Fabrication

The polydimethylsiloxane (PDMS) device used for making monodisperse hydrogel particles was fabricated by pouring uncured PDMS (10:1 polymer-to-crosslinker ratio) over a photolithographically-patterned layer of photoresist (SU-8 3025, MicroChem) on a silicon wafer. The device was cured for 1 hour in an 80° C. oven, excised with a scalpel and inlet ports were punched using a 0.75 mm biopsy puncher (World Precision Instruments, #504529). The device was bonded to a glass slide using oxygen plasma and the inner surface of the channels treated with Aquapel (PPG Industries) to render them hydrophobic. The sealed device was baked at 80° C. for 10 min.

dPCR

Monodisperse PAA particles or commercial PAA particles (Bio-Rad) were washed with 0.5% Triton-X100 (Sigma-Aldrich) in sterile water. 33 µL of washed PAA particles were mixed with 17 µL of PCR reagents to make a total reaction of 50 µL. The 50 µL mixture included 1× LongAmp Taq Reaction Buffer (NEB), 2 units of LongAmp Taq DNA Polymerase (NEB), 0.6 µM of forward and reverse primers (IDT), 0.6 µM of TaqMan® probe (IDT), 300 µM of dNTPs (Fisher Scientific) and a varying amount of budding yeast *Saccharomyces cerevisiae* genomic DNA (Milipore). For the multiplexed ddPCR, an additional 0.6 µM of forward and reverse primers and TaqMan® probe for lambda virus DNA were included. The sequence of the primers and probes used were Yeast FWD: 5'-GCAGACCAGACCAGAACAAA-3' (SEQ ID NO:1), Yeast REV: 5'-ACACGTATGTATCTAGCCGAATAAC-3' (SEQ ID NO:2), Yeast Probe: 5'-/56-FAM/ATATGTTGT/ZEN/TCACTCGCGCCTGGG/3IABkFQ/-3' (SEQ ID NO:3), Lambda FWD: 5'-GTGGCATTGCAGCAGATTAAG-3' (SEQ ID NO:4), Lambda REV: 5'-GGCAGTGAAGCCCA-GATATT-3' (SEQ ID NO:5), Lambda Probe: 5'-/Cy5/TATCCGTCAGGCAATCGACCGT TG/3IAbRQSp/-3' (SEQ ID NO:6). The mixture was incubated for 15 min to allow PCR reagent to diffuse into the particles, and centrifuged for 1 min at 6,000 g. Excess aqueous phase was removed with a micropipette. 20 µL of particles and 25 µL of HFE-7500 oil supplemented with 2% (w/w) PEG-PFPE amphiphilic block copolymer surfactant (008-Fluoro-surfactant, Ran Technologies) were mixed well by tapping in a 1.7 mL Eppendorf tube. The mixture was agitated at 2,300 rpm for 30 s with a vortexer (VWR). After transferring the emulsion to PCR tubes, the oil under the buoyant droplets was removed with a pipette and replaced with FC-40 oil (Sigma-Aldrich) containing 5% (w/w) PEG-PFPE amphiphilic block copolymer surfactant. This oil/surfactant combination yielded greater thermostability during PCR. The emulsion was transferred to a T100 thermocycler (Bio-Rad) and subjected to the following program: 94° C. for 30 s, followed by 45 cycles of 94° C. for 30 s, 53° C. for 60 s and 65° C. for 50 s, followed by a final extension of 10 min at 65° C. and held at 12° C. The droplets were imaged using the EVOS Cell Imaging System (ThermoFisher Scientific) under a 10× and 20× objective with EVOS GFP and FITC LED light sources.

Cell Culture

A budding yeast *Saccharomyces cerevisiae* strain expressing yellow fluorescent protein (YSP) fluorescent was grown at 30° C. in a standard rich media (YPD) and the cell density measured using NanoDrop (ThermoFisher Scientific). PAA particles were washed with 0.5% Triton in YPD and centrifuged to remove excess aqueous. Diluted yeast suspension was prepared to achieve Poisson-distributed cell occupancy per droplet. 1 µL of yeast suspension, 20 µL of particles and 25 µL of HFE-7500 oil with 2% (w/w) PEG-PFPE amphiphilic block copolymer surfactant were mixed well by tapping in a 1.7 mL Eppendorf tube. The mixture was vortexed at 2,300 rpm for 30 seconds. Holes were punched on the tube lid for oxygen exchange for yeast cells and 1 mL of YPD media was added. Cells were incubated at 30° C. for 10 h and imaged using the EVOS Cell Imaging under 20× objective with EVOS RFP and FITC LED light sources.

Scaling-Up the Generation of Monodisperse Emulsions

Emulsions were generated by resuspending monodisperse PAA particles in 0.3% IGEPAL and adding 20 μL of the resuspended PAA particles to each well of a 96-well plate. The combined mixture was vortexed at 2900 rpm for 1 min, or alternatively, pipetted 30 times, to yield 96 monodisperse emulsions.

Double Emulsion (Liposome) Generation Through PTE

Single emulsions were formed through vortexing at speed 10 on a table top vortexer (from VWR) for 1 min with polyacrylamide beads in an inner aqueous phase of 10 mM TrisHCl pH8, 137 mM NaCl, 2.7 mM KCl, 10 mM EDTA and 0.01% TritonX100. Liposomes were formed by adding an outer aqueous solution of 5 mM TrisHCl pH8 and 0.01% TritonX100, followed by vortexing at speed 7 on a table top vortexer (from VWR) for 20 s. Liposomes, a type of double emulsion, were formed with additional fluorescent lipid in oil phase of s Squalane mixture containing 5% (w/v) of glyceryl monooleate and 5 mg/ml of Dipalmitoylphosphatidylcholine (DPPC).

High Throughput scRNA-Seq Through PTE

The new technology expanded the capacity of scRNA-seq by increasing the throughput and simplifying the protocol described in Chemgene (see. e.g., the Chemgenes website). Drop-seq beads were encapsulated into BAC polyacrylamide hydrogel using Bis(acryloyl)cystamine as a crosslinker for polyacrylamide bead synthesis. Cells, proteinase K, and hybridization buffer were mixed along with BAC polyacrylamide beads at 4° C. Oil presaturated with 2-Mercaptoethanol was added. The mixture was vortexed for emulsification. During droplet hydrogel dissociation, 2-Me diffused into the droplet and led to dissociation of the BAC polyacrylamide particle and release of the Drop-seq beads. Cell lysis was performed by proteinase K incubation at 55° C. for 15 min. RNA was captured onto the Drop-seq beads. Drop-seq beads were recovered. Reverse transcriptase sequencing and data analysis were performed.

Species-Mixing Experiment

Mouse 3T3 cells and human HEK293 cells were washed, resuspended and mixed at a 1:1 ratio and stored in PBS buffer. Polyacrylamide particles with Drop-seq beads were synthesized using same protocol for polyacrylamide particle synthesis with Drop-seq beads added to the solution as described in greater detail below. The synthesized particles were 125 μm in diameter.

Hydrogel Beads Synthesis

The BAC hydrogel mixture used for hydrogel particle synthesis was as follows: Tris pH7.5 10 mM, EDTA 1 mM, NaCl 15 mM, Acrylamide 6.2%, BAC (BisAcroylcystamine (BAC) dissolved in ethanol at 2%) 0.54%, Ammonium persulfate 0.3% and oil comprising HFE 2% Weitz with 1% TEMED.

A standard Drop-seq device was used for hydrogel synthesis (block cell inlet channel with a piece of silver solder). Drop-seq beads were resuspended at a concentration of 100/μl with the aim of attaining 1 bead per 10 droplets in the BAC hydrogel synthesis mix. Flow rate was 2000 μl/h aqueous and 3200 μl/h oil. After droplet generation, the droplets were left at room temperature for 4 hours before de-emulsification. The same wash protocol with TBEST buffer was followed and stored at TBEST buffer at 4° C.

The size of the beads (usually about size of the droplet) and Drop-seq loading efficiency were checked. To increase the portion of beads with Drop-seq loaded, 40% Ficoll could be used for resuspending the hydrogel followed by centrifugation (500 g for 2 min). This step was repeated as needed for attaining better loading efficiency.

Instant Emulsion Formation

Single cell suspensions were prepared and diluted to the appropriate concentration. The BAC hydrogel beads were washed with PTE-seq buffer (Drop-seq lysis buffer without sarkosyl, without DTT, with 500 mM NaCl) to exchange the buffer completely.

The hydrogel beads were closely packed by centrifugation and Proteinase K (from NEB) at 20× was used. The mixture was incubated on ice for 5 min for equilibration. bME-oil was prepared by adding bME to 5% Weitz HFE oil (0.2%). The mixture was vortexed for 1 min at max speed, mixed well and stored on ice.

The concentration of close-packed beads is about 300 hydrogel beads per μl. The number of cells needed for shaking emulsion was calculated based on the number of hydrogel beads. Cell input was targeted to be 10% of the hydrogel beads number. Cells were added to the close-packed hydrogel beads and mixed gently. At least 2 volumes of the bME-oil hydrogel beads volume was added followed by vortexing at speed 7 for 30 s. The emulsion quality was examined using microscopy and the emulsions were vortexed more if necessary. Hydrogel dissociation was performed at room temperature for 15 min and cells were lysed at 55° C. for 20 min and then put on ice for 20 min for RNA capture.

Drop-Seq Protocol 30 ml of 6×SSC was added with an additional 5 μl of 10% sarkosyl on top of the emulsion and the emulsion was broken with 1 ml of PFO. The protocols from Drop-seq for Drop-seq beads clean up and RT reaction and sequencing analysis were followed according to the protocols listed at the website located by placing "http://" in front of "mccarroll-lab.com/dropseq/".

Core-Shell Microgel Formation Through PTE and Targeted Analysis

Polyacrylamide beads were conjugated with oligonucleotides, which were used as primers during PCR. Beads were soaked in PCR reagent. Excess aqueous solution was removed. Agarose, Triton and cells were added, followed by oil. PTE was performed as described herein. The oil was transferred and thermocycling was performed. The emulsions were broken and washed. FACS was used and positive beads collected before recovering the genome.

Polyacrylamide beads were modified with oligo (MH075, 2 μM final). *B. subtilis* (strain 168) were captured and MH 100 and 101 were used for PCR. The fraction with fluorescence positive droplets corresponded with *B. subtilis* (strain 168) template concentration. Fluorescence positive droplets were sorted using the FACSAria II from BD and observed under a microscope. The sorted beads were fluorescent and were surrounded by agarose shell after FACS. qPCR was performed to see the genome recovery in the agarose shell. Four primer sets in different loci were used. Signals were observed after 35 cycles and genomic DNA was encapsulated in agarose shell.

MH075:

(SEQ ID NO: 7)
/5Acryd//iSpPC/ATATTACTCTTTCCCTACACGACGCTCTTC

MH100:

(SEQ ID NO: 8)
CTCTTTCCCTACACGACGCTCTTCCGATCACGAACTGGACAAGAA

MH101:

(SEQ ID NO: 9)
/56-FAM/ATGGAGCGTTCAAGGTTCTCAA

Example 1: Generating Monodisperse Single Emulsions Using Particle-Templated Emulsification (PTE)

Results

Hydrogel particles that were greater than 95% aqueous were used for the templating, so that the final droplet was mostly aqueous, as needed for performing biochemical reactions in the resultant droplets. The particles were added to the solution to be encapsulated, with oil and surfactant, and the mixture vortexed (FIG. 2, Panels A-C and FIG. 3, Panels A-E). The hydrogel particles were permeable to molecules with hydraulic diameters smaller than the pore size, like small molecules, but were impermeable to large molecules, such as genomic DNA, which remained within the thin layer of aqueous solution surrounding the particles in the droplets. During vortexing, the particles were dispersed into continually smaller droplets until each droplet contained just one particle and a thin shell of aqueous solution, as illustrated in (FIG. 3, Panel E). Beyond this, further droplet breakup was suppressed because it required fracturing the solid particles. The result was an emulsion in which the droplets were of a similar size to the original monodisperse particles and, thus, themselves monodisperse.

PTE encapsulated any reagents present in the initial solution in the droplets, allowing them to perform compartmentalized reactions similar to what is normally achieved with microfluidics. Compounds smaller than the hydrogel pore size were absorbed before emulsification and were thus present in the final droplet containing the hydrogel. Larger compounds ended up in the thin layer of aqueous solution surrounding the hydrogel, as illustrated in FIG. 3, Panel E. Vortexing for PTE was used due to its reproducibility, although other agitation techniques were compatible, like pipetting and tube flicking.

Example 2: Optimizing Particle Templated Emulsification

Results

Figure 4:
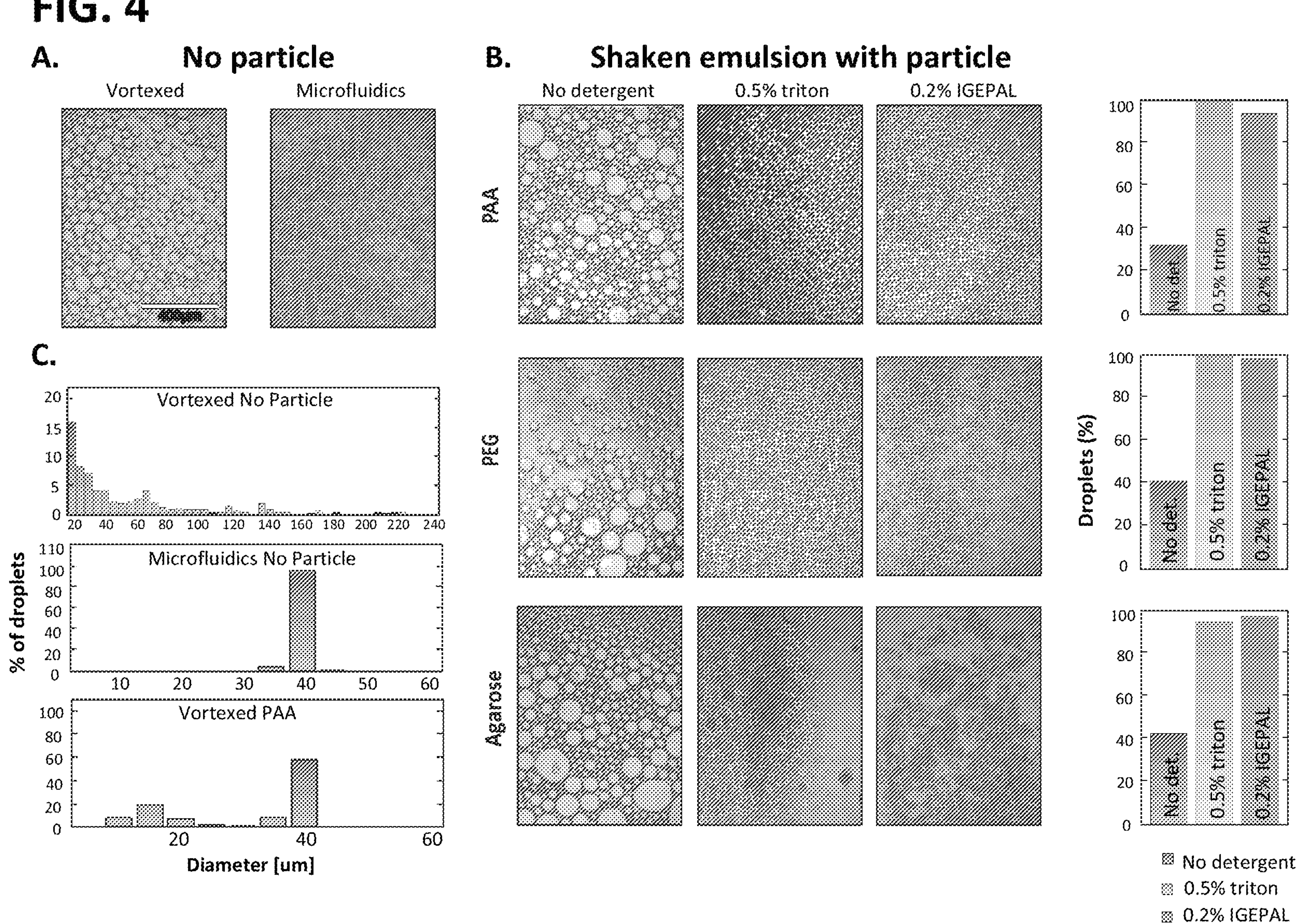
FIG. 4 provides images comparing monodispersity of droplet sizes generated by PTE relative to monodispersity of droplet sizes generated using a microfluidics device. Panel A depicts images of droplets generated without monodisperse template particles. Emulsions were generated by vortexing (left) or using a microfluidics device (right). Panel B depicts monodisperse emulsions generated using PTE with different particle compositions and aqueous-soluble detergents. Panel C depicts droplet size distribution with different emulsification methods.

While emulsions prepared by vortexing in the absence template particles were easily prepared, such emulsions were polydisperse and of limited value for precision biology (FIG. 4, Panel A). As shown in FIG. 4, Panel A (left), vortexed emulsions with no particles generated polydisperse droplets having varied size distribution, 8-218 μm in diameter (n=561) and 4.3% of droplets are 35-40 μm. On the other hand, microfluidic emulsions required specialized devices and skill, but exhibited superior monodispersity and were highly valuable (FIG. 4, Panel A). As shown in FIG. 4, Panel A (right), microfluidics emulsion generated monodisperse droplets: 95.7% of droplets are 35-38 μm in diameter (n=816). An improved method for sample encapsulation would, thus, combine the simplicity of vortexing with the quality of microfluidics.

PTE accomplished this by exploiting the rigidity of particles to resist droplet breakup below the particle size, even with vortexing. As shown in FIG. 4, Panel C, PTE generated similar size to original PAA particles, 58.2% of the droplets are 35-40 μm (n=1421) in diameter. The time to reach the final droplet size and the monodispersity of the resultant emulsion depended on fluid and particle properties. For example, particle properties like size and self-affinity, and solution properties like viscosity and interfacial tension, affected the droplet templating process. To characterize the impact of these parameters on emulsion quality, PTE was performed with different hydrogel materials and solution interfacial tensions (FIG. 4, Panel B). Particle size, carrier oil, and oil-soluble surfactant, were fixed since these properties were usually dictated by the needs of the biological reactions and less flexible.

Figure 5:
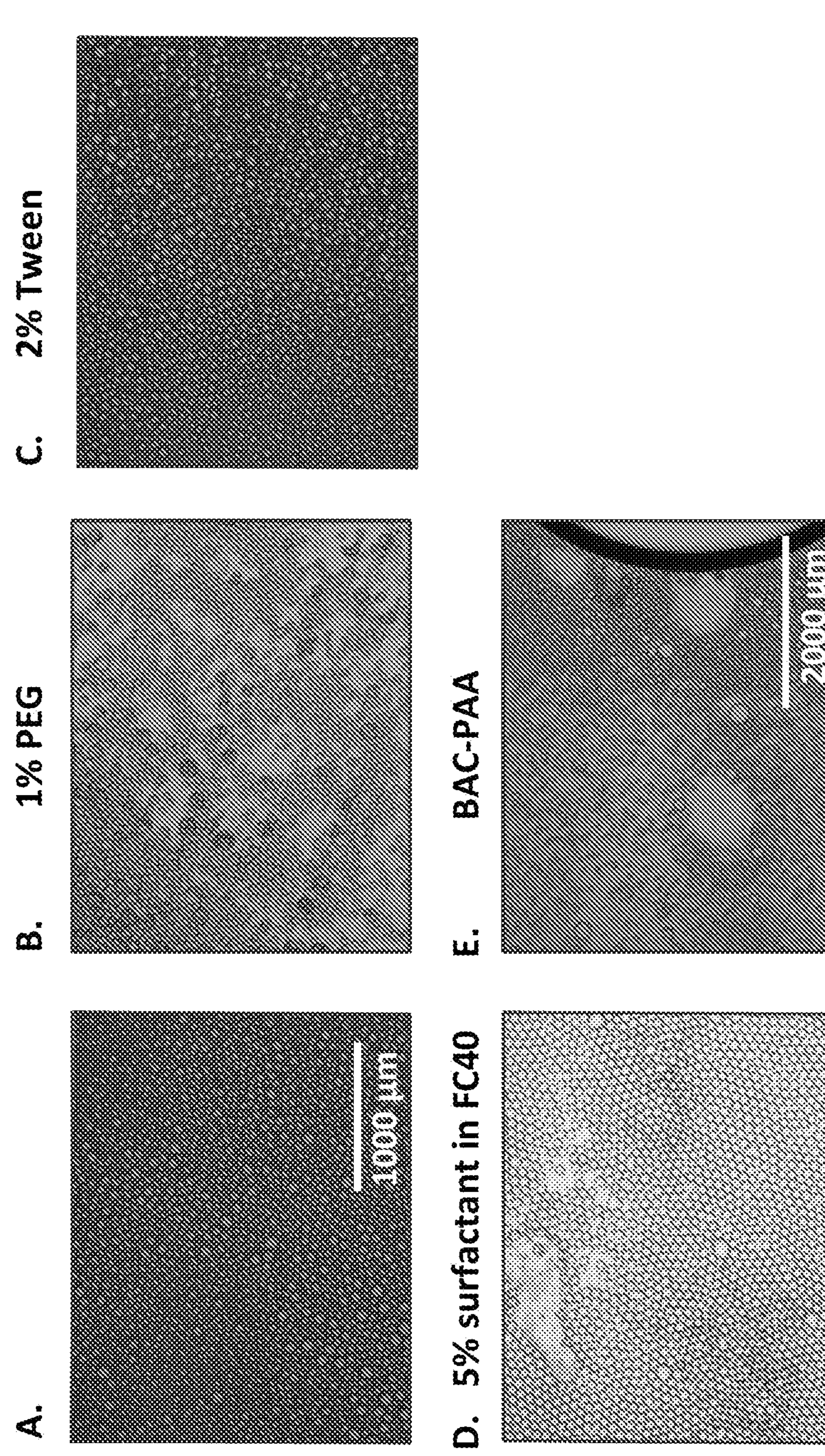
FIG. 5 provides images of droplets prepared under different PTE conditions as described in Example 2. Panel A depicts droplets prepared by vortexing PAA particles (without aqueous-phase surfactant) for 20 min. Panel B depicts droplets prepared by vortexing PAA particles with 1% Polyethylene glycol (Sigma-Aldrich) for 3 min. Panel C depicts droplets prepared by vortexing PAA particles with 2% Tween 20 (Sigma-Aldrich) for 3 min. Panel D depicts droplets prepared by mixing PAA particles with 0.5% Triton with FC-40 with 5% fluorosurfactant and vortexing for 3 min. Panel E depicts droplets prepared using PAA particles with 0.18% N,N'-bisacryloylcystamine as a crosslinker and vortexing the PAA particles with 0.5% Triton for 30 sec.
Figure 6:
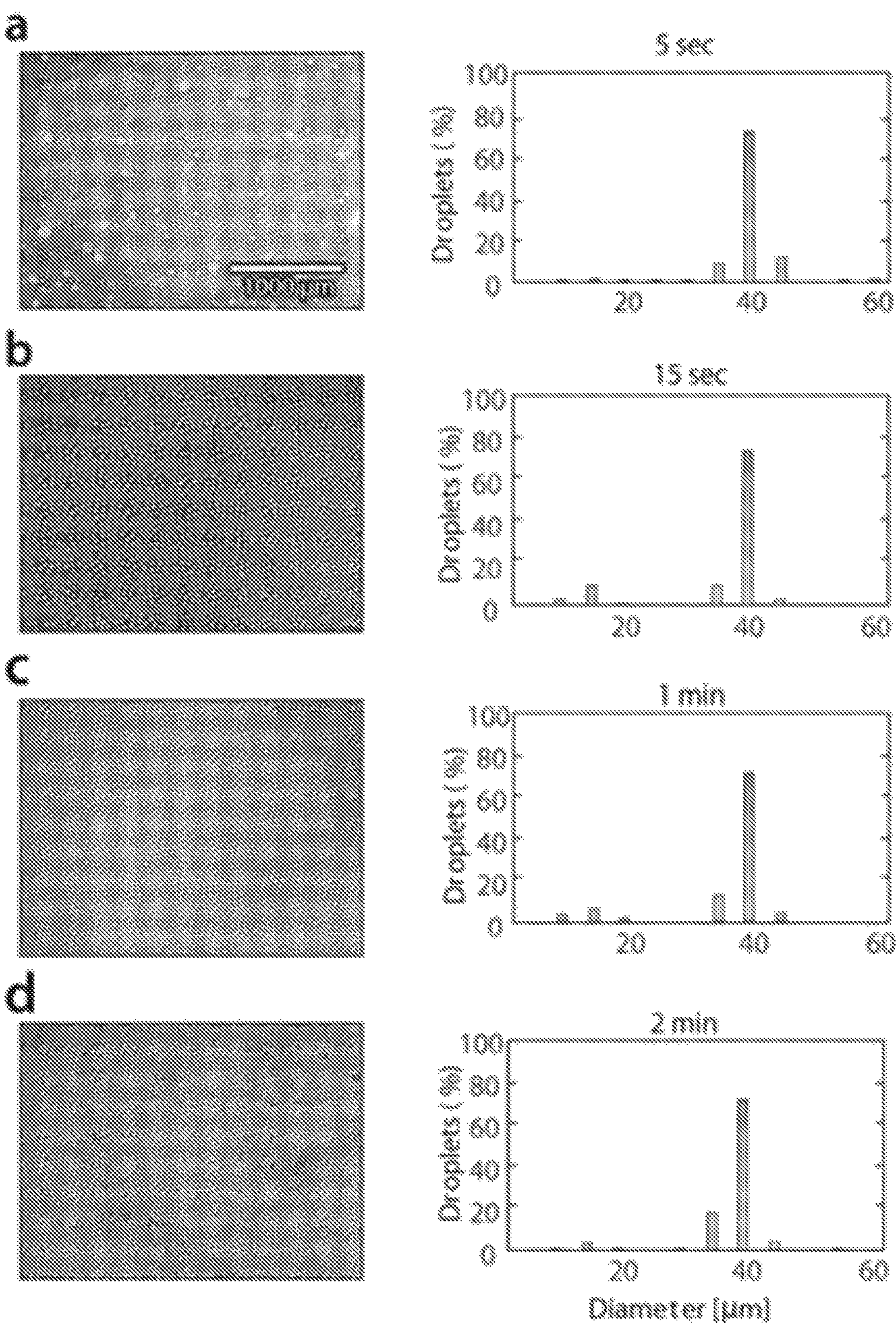
FIG. 6 provides images and histograms of droplets generated with different vortexing times. Panel A depicts images and histograms with a vortexing time of 5 sec. Panel B depicts images and histograms with a vortexing time of 15 sec. Panel C depicts images and histograms with a vortexing time of 1 min. Panel D images and histograms with a vortexing time of 2 min.

To modulate interfacial tension, aqueous-soluble surfactants were added to the droplet phase, which is compatible with most biochemical reactions. When the aqueous-phase surfactant was omitted, the vortexed droplets were polydisperse for all hydrogel types (FIG. 4, Panel B); without intending to be bound by any particular theory, this may be due to inter-particle affinity and high interfacial tension preventing breakup of large, non-uniform, multi-core droplets. Increasing vortexing up to 20 min did not appreciably change emulsion quality. Multi-core emulsions were observed and the emulsion was polydisperse (FIG. 5, Panel A). By contrast, when surfactants were included in the aqueous phase, particle affinity and interfacial tension were reduced; monodispersed single-core droplets were generated with 30 s of vortexing (FIG. 4, Panel B), longer vortexing durations did not substantially alter the appearance of the resultant emulsion (FIG. 6, Panels A-D). PAA particles with 0.5% Triton in HFE oil with 2% fluorosurfactant were used and vortexed for 5 sec (FIG. 6, Panel A), 15 sec (FIG. 6, Panel B), 1 min (FIG. 6, Panel C), and 2 min (FIG. 6, Panel D). Histograms showed the droplet size distribution with different vortexing times.

As shown in FIG. 4, Panel B, PAA, PEG or agarose particles were used as templates and emulsified with different surfactants. Monodisperse droplets were generated with an aqueous phase surfactant (Triton and IGEPAL). Of the particles tested, droplets formed from polyacrylamide (PAA) and polyethylene glycol methacrylate (PEG) particles yielded the most uniform emulsions (FIG. 4, Panel B). Agarose-particle emulsions were less uniform. Without intending to be bound by any particular theory, this may be due to their self-affinity. Other aqueous-phase surfactants were also used, although the requisite vortexing parameters and emulsion quality differed (FIG. 5, Panels B-E).

Figure 7:
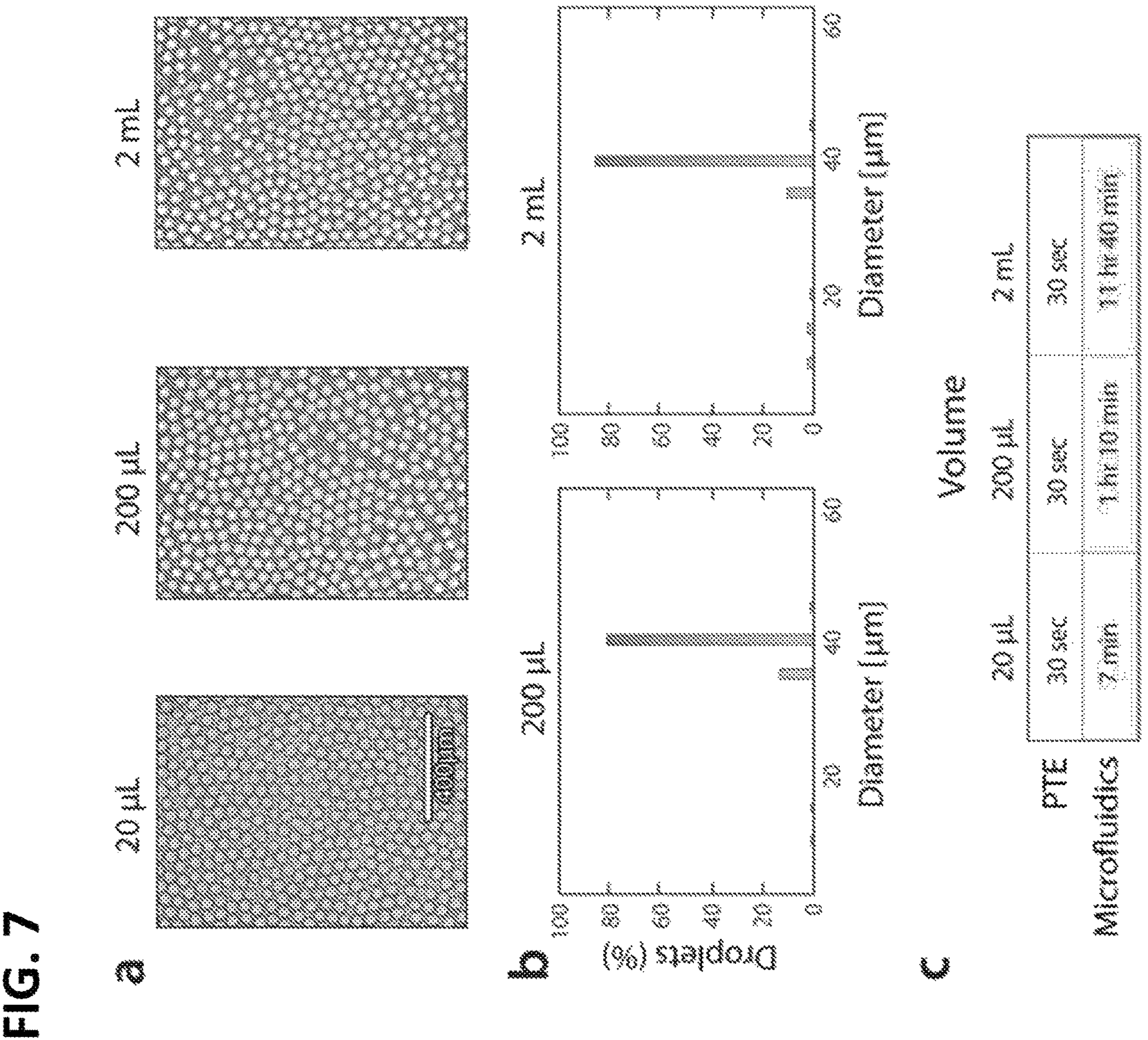
FIG. 7 provides results of a demonstration indicating that PTE allows for the production of monodispersed emulsions from microliter to milliliter scales. Panel A depicts images of PTE emulsions of different total volumes. Panel B depicts histograms of the droplet size distribution for 200 μL and 2 mL emulsions. Panel C provides a table comparing droplet generation time of PTE and microfluidics-based generation methods.

PTE was scalable, because the time required to generate an emulsion did not depend on the volume of the emulsion (FIG. 7, Panels A and B). PTE allowed for rapid and facile production of monodispersed emulsions from microliter to milliliter scales. The samples comprised PAA particles with 0.5% Triton suspended in 1.25 volume of HFE oil with 2% (20 μL) or 5% (200 μL and 2 mL) fluorosurfactant (FIG. 7, Panel A). All emulsions, independent of the total volume were vortexed for 30 s to generate the droplets. Histograms of the droplet size distribution for the 200 μL and 2 mL emulsions demonstrated equivalent monodispersity (FIG. 7, Panel B).

These results differed from conventional microfluidic emulsification where generation time scaled with volume. Droplet generation times of PTE and microfluidics were compared for a typical droplet generation rate of 1 kHz. With PTE, generating 20 μL of emulsion required the same time as generating 2 mL of emulsion (FIG. 7, Panel C, top), while generating 2 mL of emulsion required about 11 hours (FIG. 7, Panel C, bottom) using microfluidics. The scalability of PTE was an advantage for applications requiring emulsification of large volume samples. Moreover, because the emulsion generation occurred in the sample reservoir and did not require shuttling samples to and from a microfluidic instrument, PTE was also scalable for emulsifying large numbers of samples.

Hydrogels having a diameter of about 30 μm to about 80 μm were used with similar results, with data for 50 μm hydrogels shown, but other particle types may be compatible with the method, including different sizes, hydrogel chemistries, and porosities. While fluorinated oil and surfactant were used for the carrier phase, other formulations may be compatible, including silicon and hydrocarbon oils and surfactants. Other polar phases could also be used, provided they formed stable emulsions, which may be valuable for generating core-shell structures. These properties may provide the needed flexibility for extending PTE to other areas, such as cost-effective and scalable encapsulation of compounds in double emulsions.

In addition to the desired monodispersed droplets with size similar to the templating particles, PTE generated tiny "satellite droplets" containing no particles. The number of satellite droplets depended on the amount of excess aqueous solution surrounding the particles, emulsion interfacial tension, and vortexing time and power. To reduce their number, excess aqueous solution can be removed from the particle-sample mixture prior to vortexing. Nevertheless, while aesthetically unpleasing, satellite droplets contributed negligibly to biological reactions performed in the emulsions, because they usually comprised a relatively small fraction of the total sample volume (<3%).

The engulfed volume could be predicted after considering vortex power, surface tension and particle size, etc. Vortexing generated a distribution of velocities in the sample, and each droplet experienced a random sample of these velocities during emulsification. Vortexing was a reasonably controlled method for agitating fluids and, thus, it was possible to identify a power that yielded predominantly single core droplets with uniform engulfment volumes, as shown herein.

A common challenge in droplet microfluidics was the need to efficiently encapsulate discrete entities, like beads and cells. Microfluidic techniques normally encapsulated these entities randomly, resulting in inefficient Poisson loading in which only a small fraction of the droplets was properly loaded. A unique and valuable property of PTE was that every droplet of the appropriate size contained one templating particle (FIG. 4, Panel B). If these particles were an essential component of the reaction, most droplets contained what was needed. Other components, however, such as cells, beads, and DNA molecules, were loaded randomly. Indeed, efficient hydrogel encapsulation was a key step in recently reported single cell sequencing technologies and exploited in commercial instruments (Zhu Z, Yang CJ (2017), Hydrogel Droplet Microfluidics for High-Throughput Single Molecule/Cell Analysis, Acc Chem Res 50(1): 22-31).

Example 3: PTE Enabled Accurate DNA Quantification with Digital Droplet PCR (ddPCR)

Results

Figure 8:
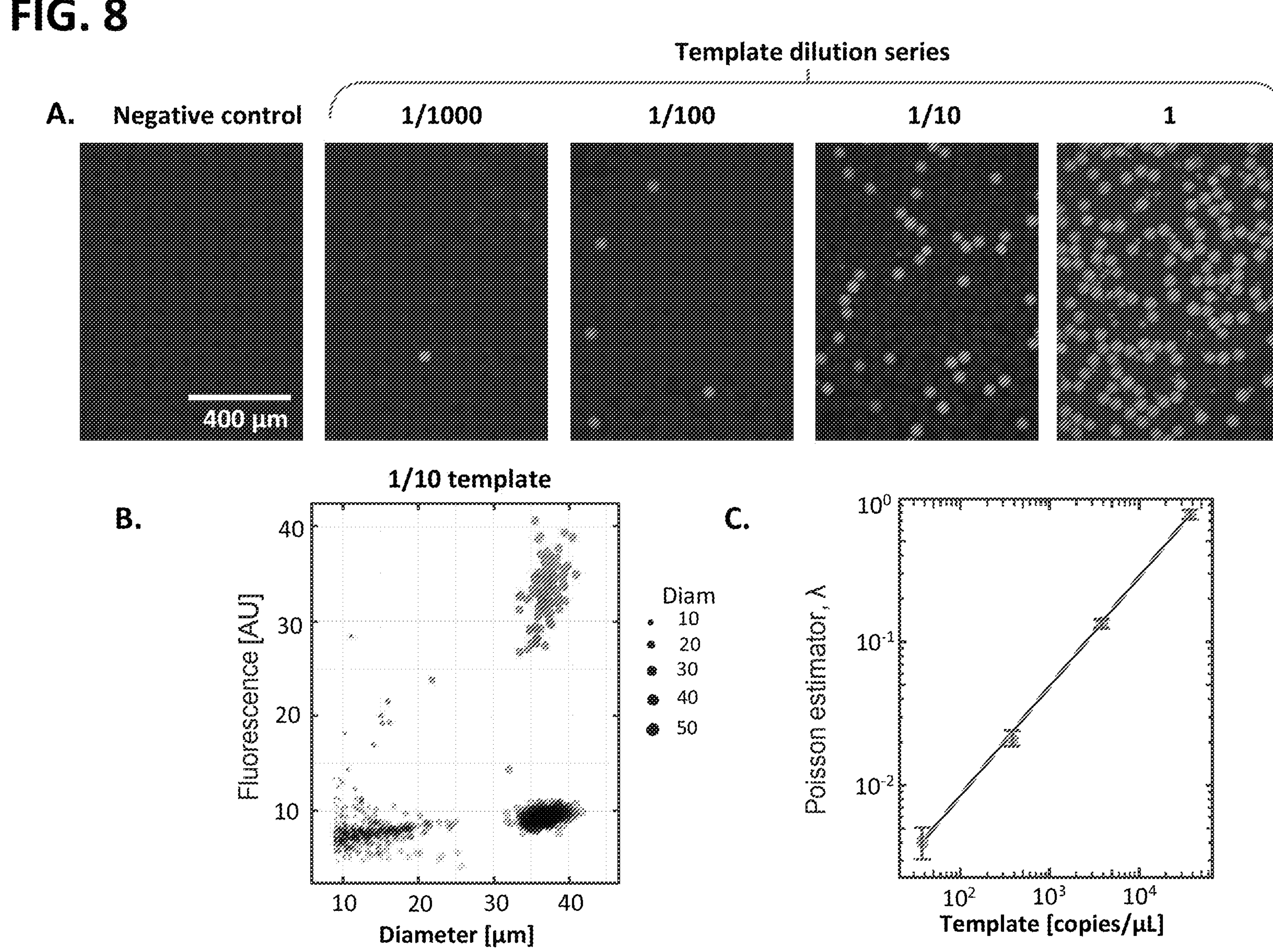
FIG. 8 provides images of PTE-digital droplet PCR (ddPCR) and quantification using monodisperse template particles. Panel A depicts fluorescence images of droplets after PCR amplification with TaqMan® probes and primers for yeast genomic DNA templates at varying dilution factors (A.U.=0, 0.001, 0.01, 0.1, 1.0). The fractions of observed fluorescence-positive droplets correspond with the template concentrations. Panel B depicts a scatter plot showing the size and fluorescence distribution from a sample in the dilution series. The population with low fluorescence (<20 AU) and small diameter (<30 μm) is composed of droplets containing no hydrogel particles. The population with expected diameter (30-40 μm) consists of single-hydrogel-core droplets. This population forms two tight clusters: high fluorescence (PCR-positive) and low fluorescence (PCR-negative, no-template droplets). Panel C depicts the average template copy number per droplet estimated by assuming a Poisson distribution scales with the controlled template concentrations over the tested three-decade range ($R^2$=0.9994 and error bars depict standard deviation).

PTE allowed facile, microfluidics-free ddPCR. To illustrate this, PTE was used to encapsulate several DNA samples at different concentrations of a target molecule (FIG. 8, Panel A). Just as in microfluidic ddPCR, increasing target concentration increased the number of fluorescent droplets. To determine whether this allowed concentration estimation, conventional ddPCR analysis was followed and droplet fluorescence quantified using imaging, plotting the results as fluorescence versus diameter (FIG. 8, Panel B). Three droplet populations were visible, at low fluorescence and small diameter (satellite droplets), at the expected 30-40 μm diameter and low fluorescence (PCR-negative), and a similar size range but high fluorescence (PCR-positive). The satellite droplets were ignored and the target concentration for the correctly-sized droplets modelled via Poisson statistics, $\lambda=-\ln(1-p)$, where $\lambda$ is the template copy number per droplet and p is the fraction positive.

Figure 9:
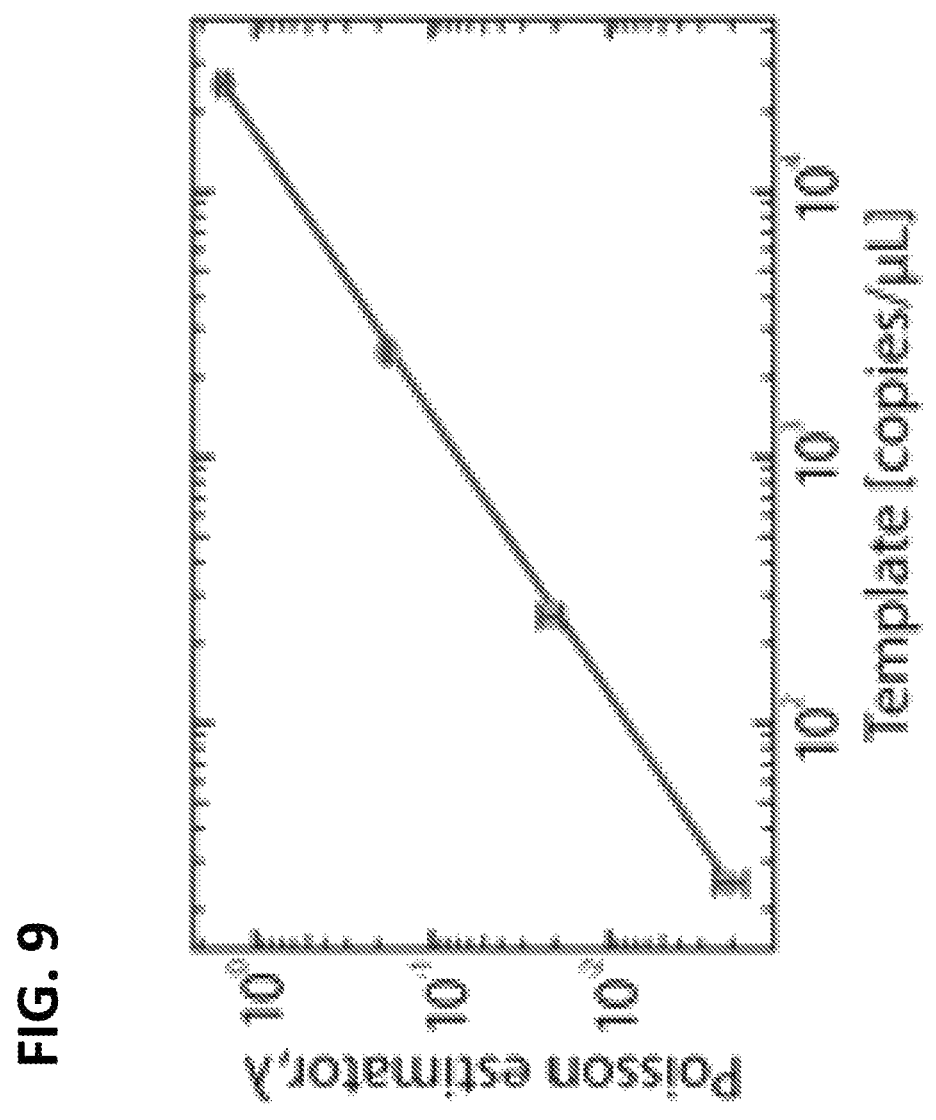

The measured concentration followed the expected scaling over the three-decade tested range, demonstrating that PTE-based ddPCR (FIG. 8, Panel C) performed like microfluidics-based ddPCR (FIG. 9). The PTE method utilized hydrogel particles that templated the droplets, which were made using microfluidics. Even with microfluidically-made particles, PTE represented a substantial simplification for ddPCR, since one large batch of synthesized particles could be used for many analyses runs.

Figure 10A:
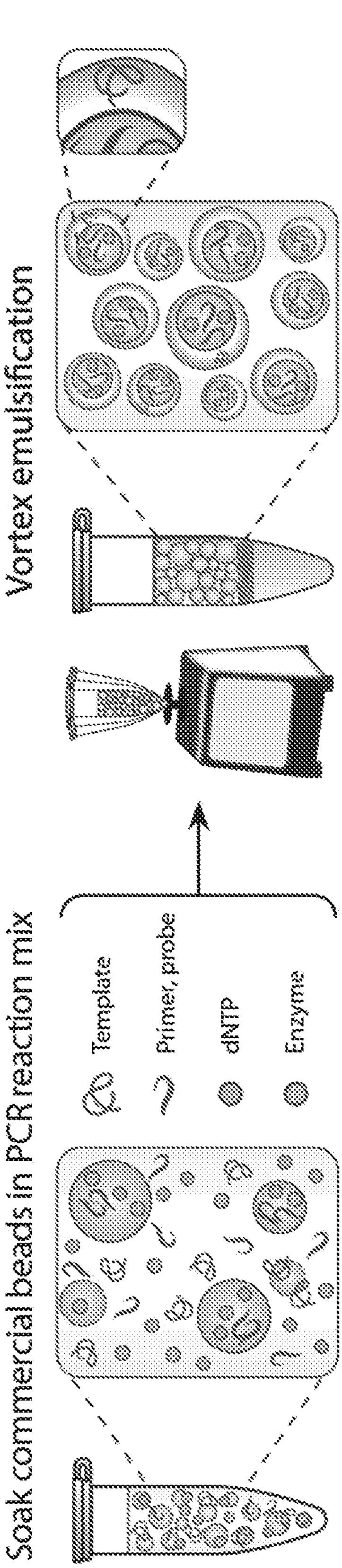
FIGS. 10A and 10B provide schematics, images, and graphs of PTE-based ddPCR and quantification with commercially-available particles.
Figure 10B:
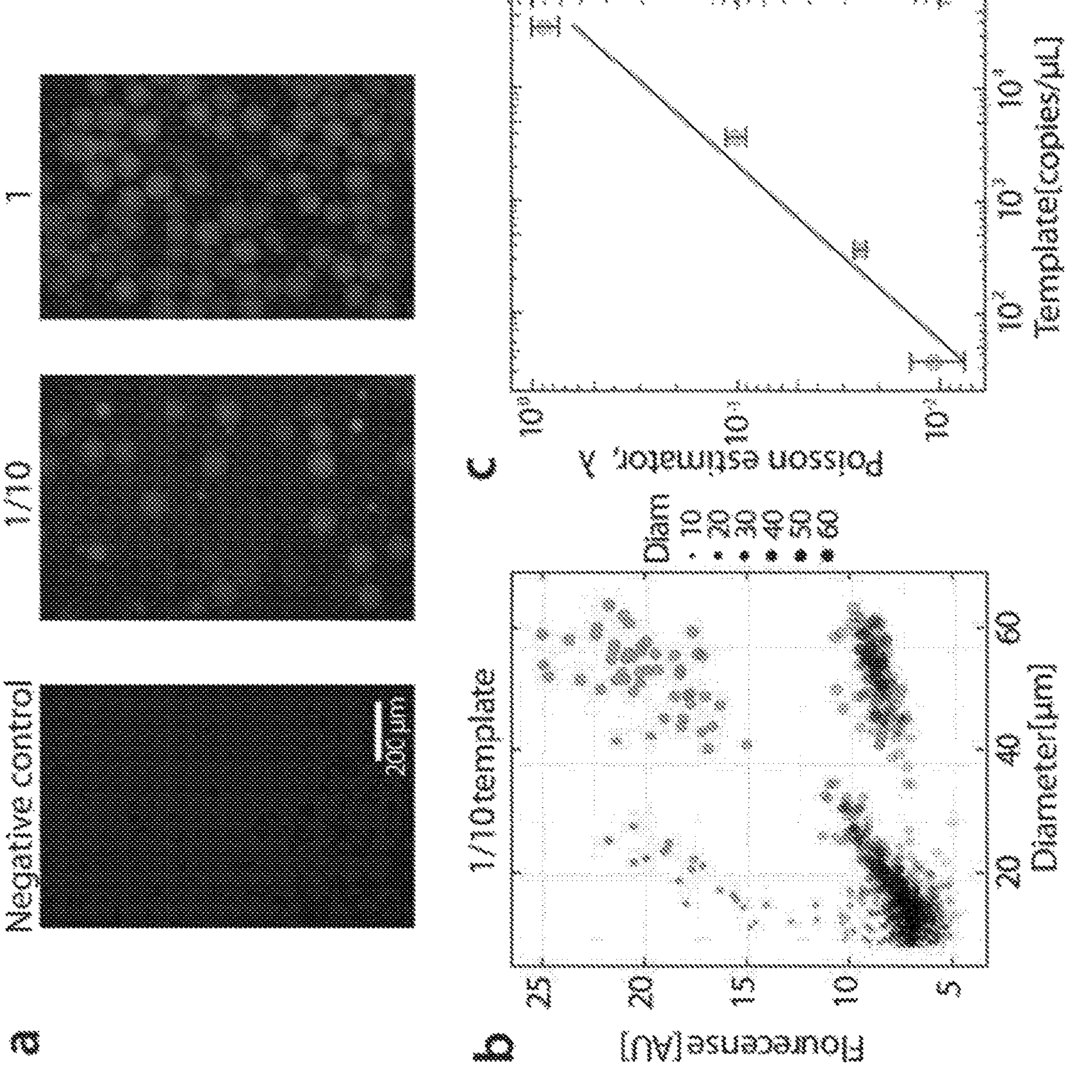

Hydrogel microspheres with a variety of compositions, sizes, and uniformity could be purchased from commercial vendors. These spheres were usually sold as components for purification columns and, thus, quality-controlled and free of contaminants that could interfere with droplet reactions. To show that PTE could be performed with commercial monodisperse template particles (FIGS. 10 A and 10B), monodispersed PAA spheres ranging from 45-90 μm in diameter were purchased; this size distribution was larger than for particles made with microfluidics, typically below 5%, but was acceptable for most applications, including ddPCR. To demonstrate this, the particles were used to perform ddPCR with PTE, and similar droplet fluorescence properties were observed (FIG. 10B, Panel A). The larger diameter distribution resulted in a broader scatter in the plot, both in size and fluorescence, but the PCR positive and negative populations were nevertheless discernable (FIG. 10B, Panel B). Target concentration was varied and standard ddPCR analysis was performed, achieving accurate measurements over the same range (FIG. 10B, Panel C). When the variability in droplet size was included by using multiple Poisson distributions weighted by droplet volume, the correction factors for estimated copy numbers were small, ranging from 0.1% (for the lowest concentration) to 4.5% (for the highest concentration).

Microfluidically-made particles were used to characterize PTE, since they were monodispersed and thus allowed accurate measurement of droplet volume variation. However, as shown herein, commercially available beads that were relatively uniform sufficed for many applications.

Example 4: Multiplexed PTE-ddPCR

Results

Figure 11:
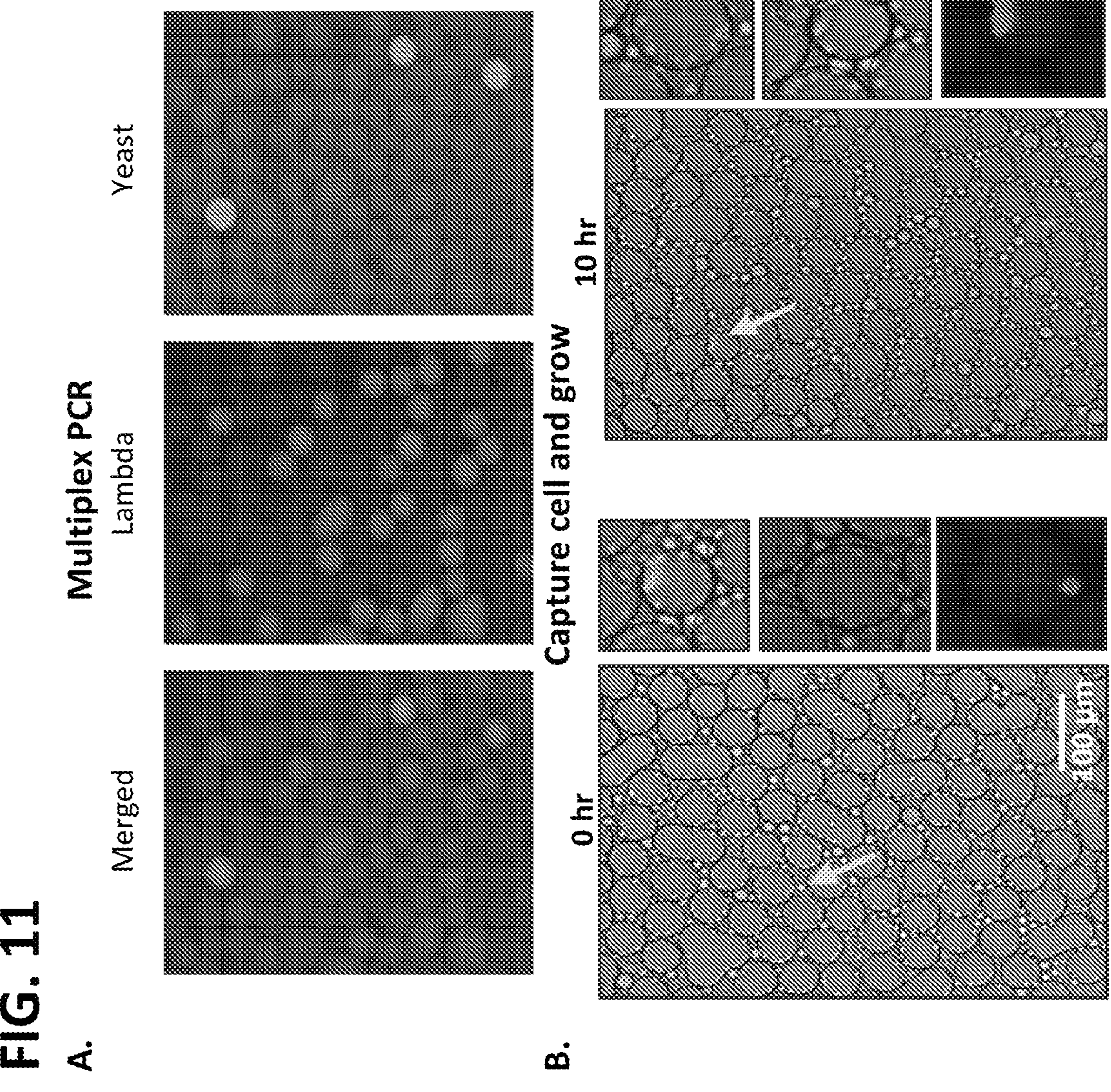
FIG. 11 provides images showing multiplex PTE-based ddPCR of mixed lambda virus and yeast DNA. Panel A depicts the probes targeting lambda virus or yeast are fluorescently labeled with Cy®5 dye (red) (CAS number 144377 May 9; IUPAC name 3-12-[(1E,3E,5E)-5-[1-(5-carboxypentyl)-3,3-dimethylindol-2-ylidenelpenta-1,3-dienyl]-3,3-dimethylindol-1-ium-1-yl]propane-1-sulfonate) and carboxy-fluorescein (FAM) (green), respectively. Panel B depicts yeast cells growing in droplets prepared by PTE. After 10 hours of incubation, colonies grown from single encapsulated cells can be detected by endogenous yellow fluorescent protein (YFP) fluorescence.

To demonstrate that PTE-based ddPCR could be multiplexed, a mixture of Lambda virus and *S. cerevisiae* genomic DNA was analyzed. TaqMan probes targeting either the Lambda virus (red) or yeast (green) genomes were used. The DNA of both organisms was mixed together, and the sample emulsified with PTE. Many droplets were either pure red or green, indicating that they contained either Lambda or yeast genomic DNA, respectively (FIG. 11, Panel A). However, in rare instances, a droplet contained one of each target and, thus, was double-positive, appearing yellow (FIG. 11, Panel A, merged). Since these nucleic acids did not physically associate, the likelihood of a double positive could be described by a Poisson double-encapsulation process. Deviations from Poisson statistics thus represented associations of sequences.

Example 5: PTE Used in Yeast Cells

Results

PTE was used to encapsulate single yeast cells using hydrogel spheres to template droplet generation. The PAA monodisperse template particles were added to a suspension of yeast and the mixture was emulsified by vortexing. The cells were suspended at a low concentration so that most droplets were empty, but a small fraction contained single cells, just as with microfluidic cell encapsulation. Because the micron-scale yeast could not diffuse into the nanometer pores of the monodisperse template particles, they ended up in the aqueous shell near the periphery of the droplets (FIG. 11, Panel B). The number of yeast encapsulated per droplet could be modulated by cell concentration in the sample.

The droplet environments were compatible with yeast growth. Without intending to be bound by any particular theory, this may be because PAA is a biologically inert hydrogel that comprises greater than 95% aqueous. Consequently, when the encapsulated yeast cells were incubated for 10 hr, they grew into clonal microcolonies (FIG. 11, Panel B).

Example 6: RNAseq (Prophetic)

Polyacrylamide hydrogel beads are first synthesized with more than 10^9 single stranded oligonucleotides bonded to it, followed by wash and re-suspension. The bead fabrication procedure is performed with a "split and pool" method for barcode synthesis onto the beads. The finished barcode beads contain uniquely barcoded single stranded DNA with other components including polyT tail and a T7 promoter sequence. These single stranded DNA can be released from the hydrogel beads upon UV exposer. The beads, cells and RT mix are combined and PETE is performed as described herein to encapsulate single cell in droplets with reverse transcription reaction mix. The emulsion is exposed to UV light followed by heating up to 50° C. to perform the reverse transcription reaction. During the process, single strand DNA on beads is released to function as RT primers and the RNA from the cell is released to function as templates. The emulsion was is then broken and cDNA is recovered followed by standard in vitro transcription and library preparation for next generation sequencing to collect the data of single cell gene expression profile analysis.

Example 7: Scaling-Up the Generation of Monodisperse Emulsions

Results

Figure 12:
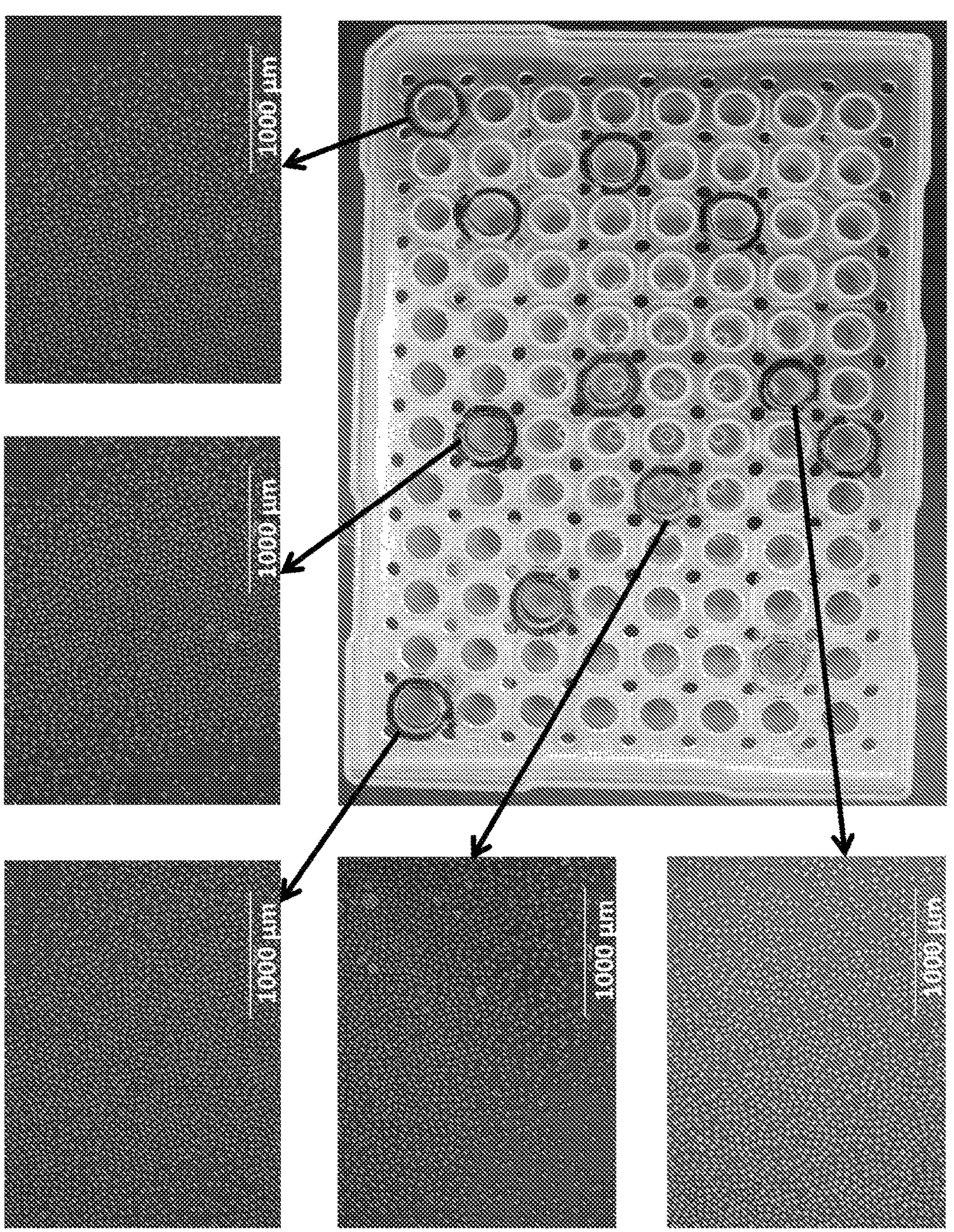
FIG. 12 provides images of monodisperse emulsions prepared in a 96 well plate format as discussed in Example 7.

Monodisperse polyacrylamide particles were first synthesized according to the methods disclosed herein, and then washed with IGEPAL. The monodisperse particles were added into a 96-well plate. PTE was performed according to the disclosure to create 96 uniform, single-cell emulsions simultaneously (FIG. 12).

Example 8: Generating Double Emulsions Using Particle-Templated Emulsification (PTE)

Results

Figure 13:
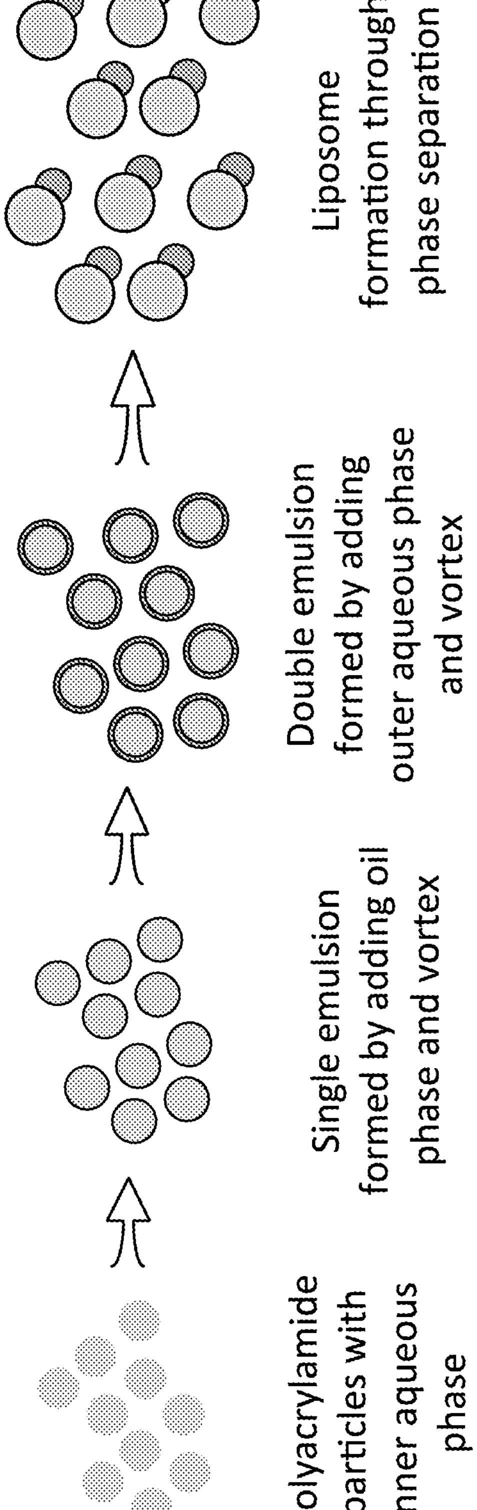
FIG. 13 provides a schematic and related images of a workflow for generating double emulsions and GUVs (i.e., liposomes) through PTE. Panel A depicts a schematic workflow of the instant liposome generation method. Panel B depicts a single emulsion formed through vortexing with polyacrylamide beads. Panel C depicts an image of a liposome formed by adding an outer aqueous solution followed by vortexing. Scale bar=400 μm. Panel D depicts a fluorescent image of a formed liposome with additional fluorescent lipid in the oil phase.
Figure 13:
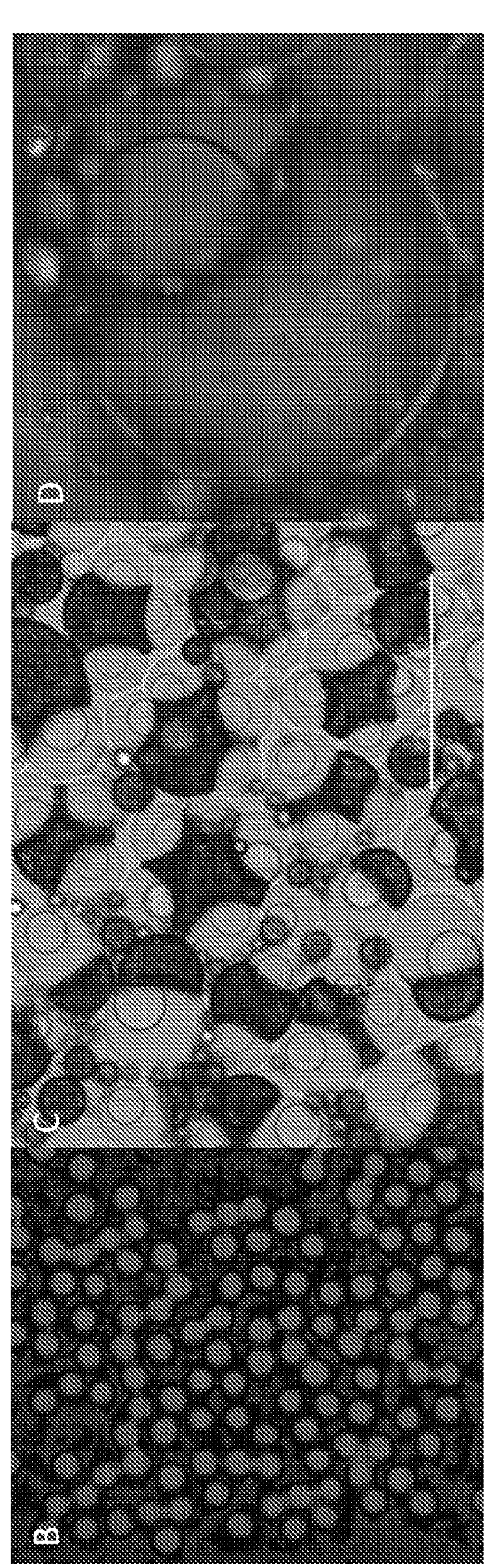

The technology described herein enabled production of liposomes, one type of double emulsion, with precise control. As shown in FIG. 13, Panel A, polyacrylamide particles were provided in an inner aqueous phase (10 mM TrisHCl pH8, 137 mM NaCl, 2.7 mM KCl, 10 mM EDTA, and 0.01% TritonX100) were used to generate double emulsions (or liposomes) through PTE. As shown in FIG. 13, Panel B, single emulsions were first formed by adding an oil phase (Squalane mixture containing 5% (w/v) of glyceryl monooleate and 5 mg/ml of DPPC. As shown in FIG. 13, Panel C, double emulsions were generated by adding an outer aqueous phase containing 5 mM TrisHCl pH8 and 0.01% TritonX100 and vortexing. Liposomes were formed through phase separation. As shown in FIG. 13, Panel D, the formed liposomes with additional fluorescent lipid in oil phase were imaged with an EVOS fluorescent microscope.

Example 9: High Throughput RNAseq Through PTE

As shown in FIGS. 14A-14C, a protocol enabling microfluidics-free single cell RNAseq (scRNA-seq) was developed, which allowed profiling of the transcriptome from thousands of single cells with simple reagents. A combination of proteinase-based lysis approach, chemical triggered hydrogel depolymerization and barcoded RNA capture beads was utilized to achieve the droplet formation, cell lysis and RNA capture in one single step. The technology expanded the capacity of scRNA-seq by increasing the throughput and simplifying the conventional protocol.

Figure 15:
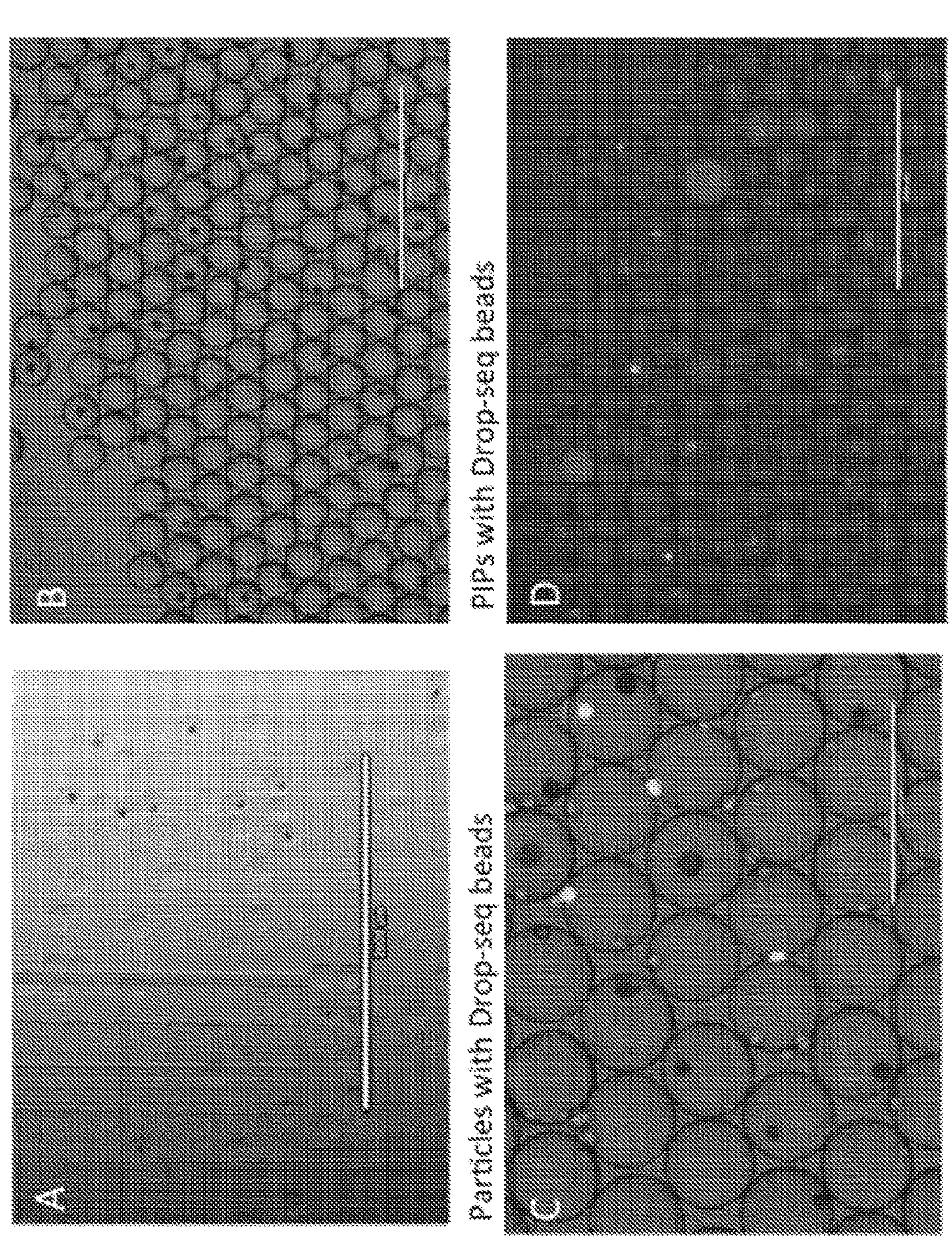
FIG. 15 provides image results from experiments performing high throughput scRNA-seq through PTE, a microfluidics-free scRNA-seq. Panel A depicts a microscopic image of particles with Drop-seq beads, having a scale bar of 2000 μm. Panel B depicts a microscopic image of emulsions with Drop-seq beads, having a scale bar of 1000 μm. Panel C, with a scale bar of 400 μm, and Panel D, with a scale bar of 1000 μm, depict microscopic images of calcein green stained cells encapsulated into droplets before and after lysing. Panel E provides a graph depicting data from a human-mouse mixed cell experiment.
Figure 15:
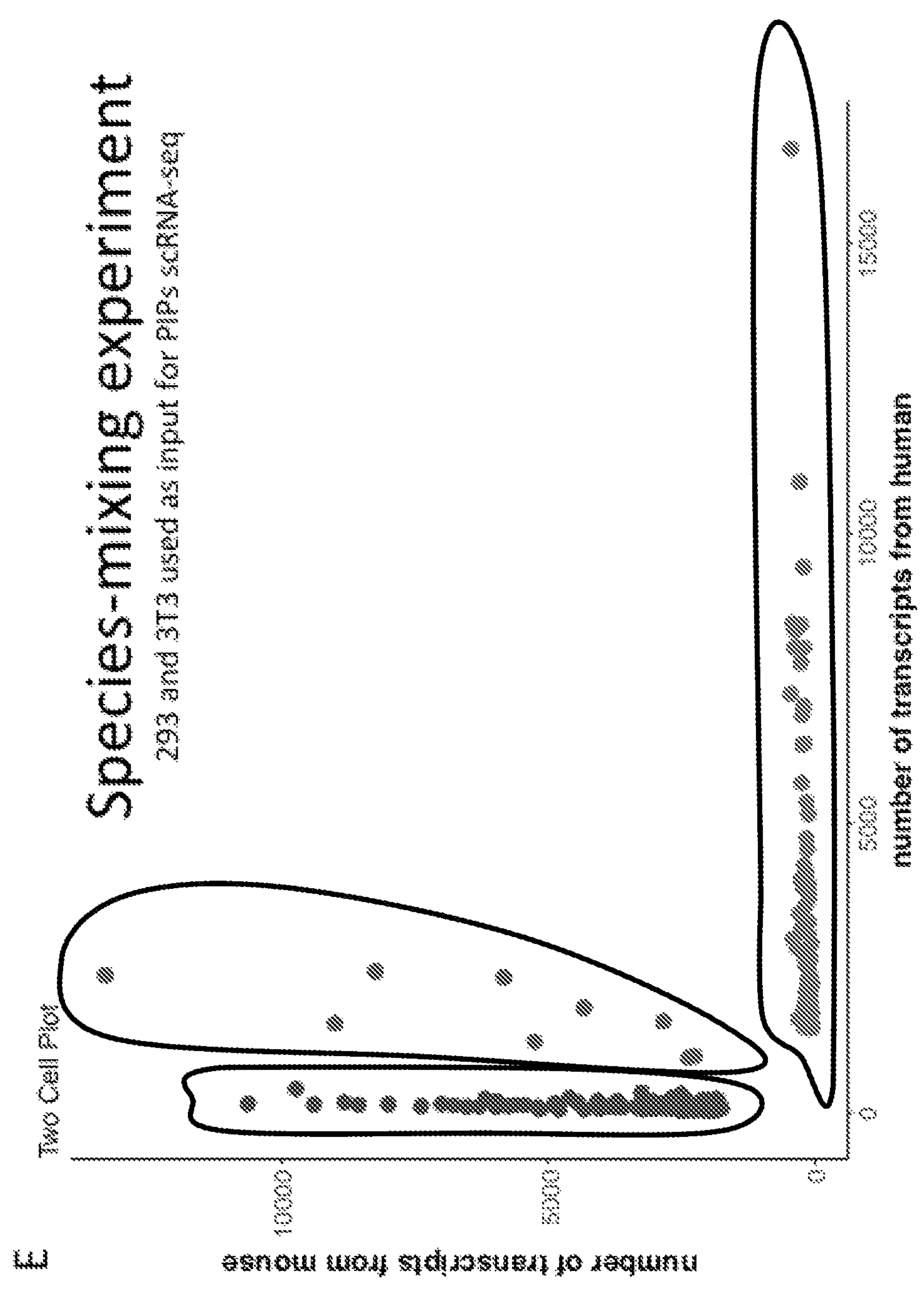

Drop-seq beads (FIG. 14 A; FIG. 15, Panel A) were first encapsulated into BAC polyacrylamide hydrogel using Bis (acryloyl)cystamine (BAC) as crosslinker for polyacrylamide bead synthesis, followed by wash and re-suspension. The beads, cells, proteinase K and hybridization buffer were combined. Oil pre-saturated with 2-Mercaptoethanol (2-Me) was added and PTE was performed as described herein to encapsulate single cells in droplets (FIG. 14B; FIG. 15, Panel B). The cells were lysed by proteinase K. Detergent was not used for cell lysis so as to avoid lysis prior to the formation of droplets. Proteinase K required a longer time and higher temperature to lyse the cells efficiently and was thus well suited to the method. Following the addition of proteinase K and the formation of droplets, the temperature was elevated from 4° C. to 55° C. to facilitate proteinase K activation and cell lysis. After cell lysis and RNA capture, the emulsions were broken, the proteinase K was washed out, and the Drop-seq beads were recovered (FIG. 14C.

In FIG. 15, microscopic images depict calcein green strained cells encapsulated into droplets before lysing (FIG. 15, Panel C) and after lysing (FIG. 15, Panel D). Data from a human-mouse mixed cell experiment illustrated the effectiveness of the scRNA-seq workflow described herein (FIG. 15, Panel E).

Example 10: Core-Shell Microgel Formation Through PTE and Targeted Analysis

Figure 16:
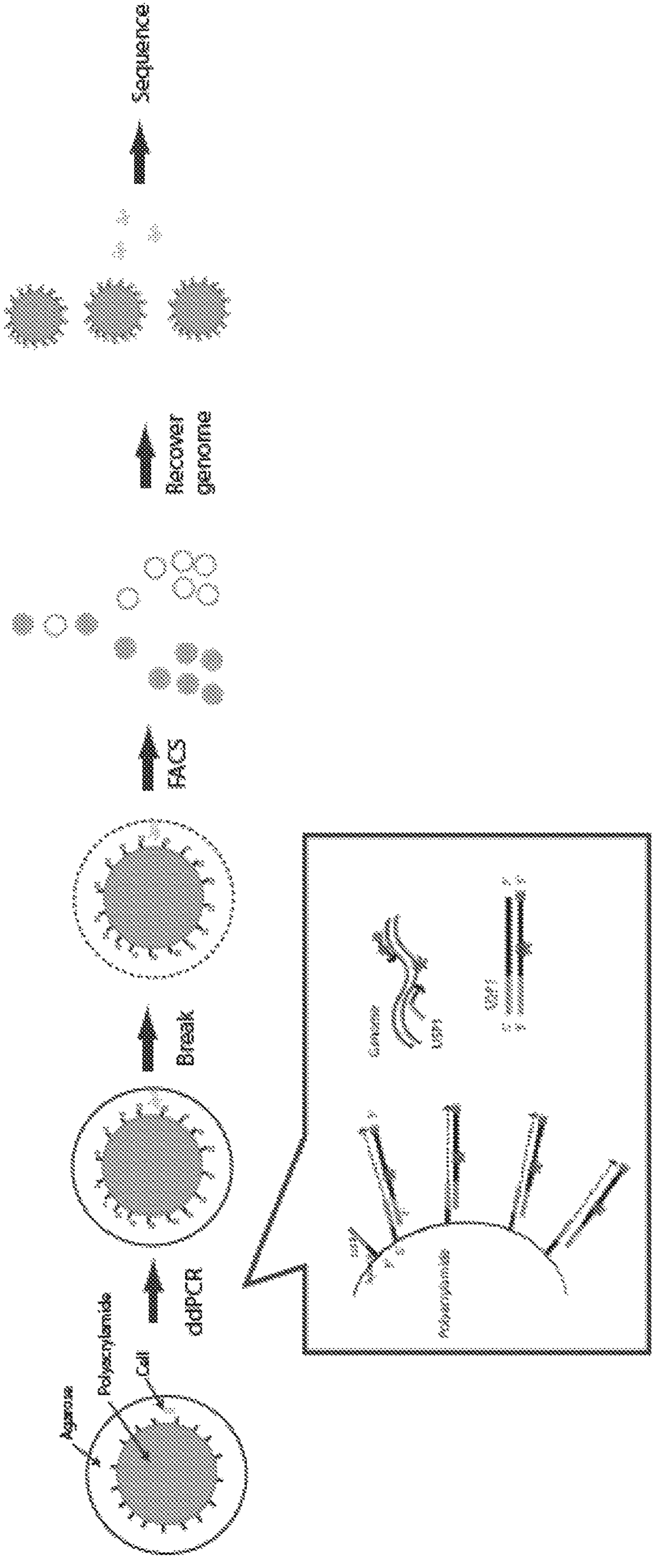
FIG. 16 provides a schematic diagram of an embodiment of a workflow to create a core-shell microgel using instant emulsion technology, which combines affinity-based PTE with targeted analysis.
Figure 17:
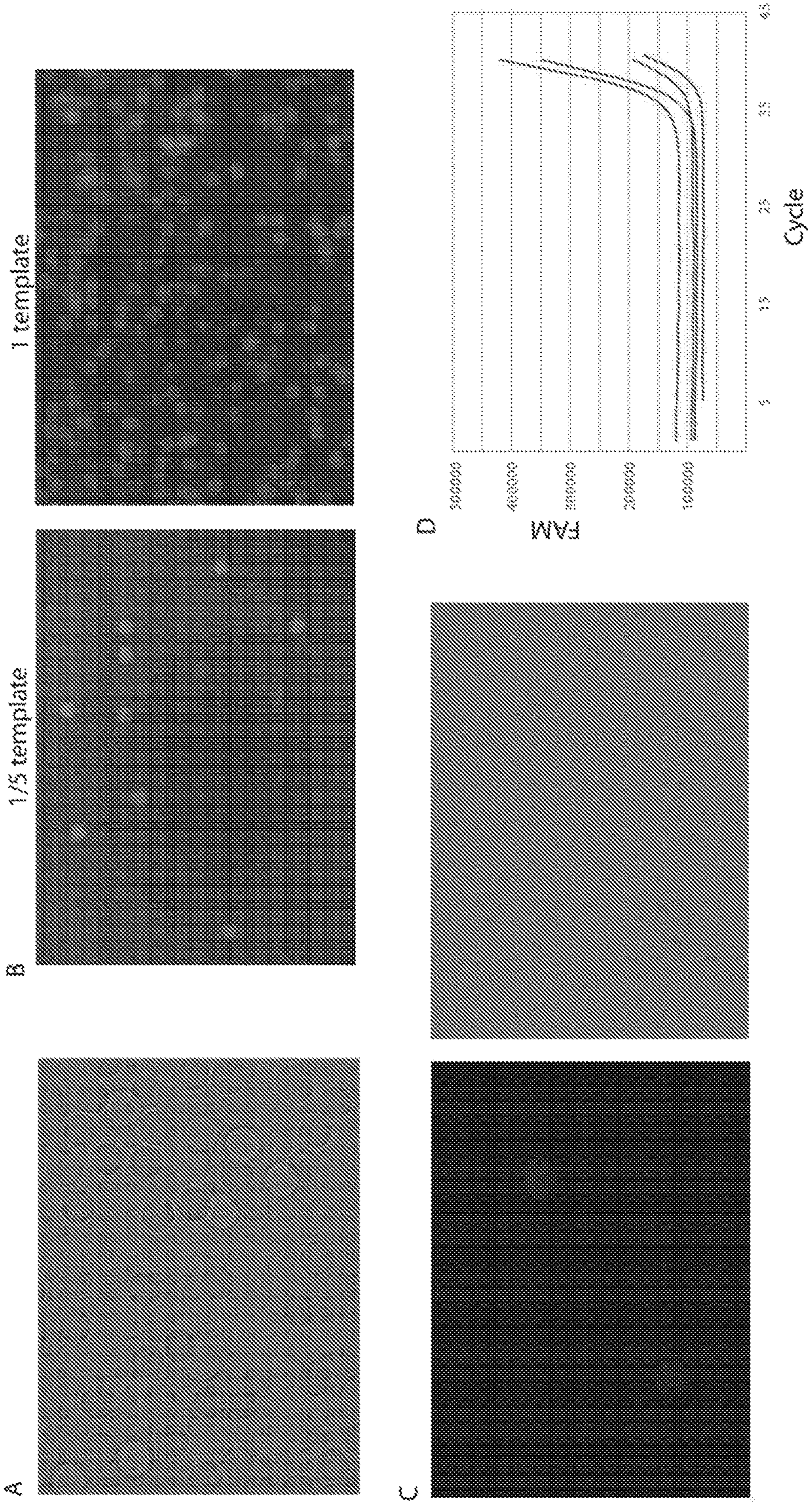
FIG. 17 provides images of polyacrylamide core beads with an agarose shell. Panel A depicts the polyacrylamide core beads surrounded by agarose shell after droplets are broken. Panel B depicts ddPCR in polyacrylamide core beads with agarose shell at two dilution factors. Panel C depicts images of the droplets after FACS. Panel D depicts the qPCR result.

As shown in FIG. 16, a method to create core-shell microgel using instant emulsion technology was developed, which combined affinity-based PTE with targeted analysis. it is contemplated that the core-shell microgel created using the instant emulsion technology could be used to retain a variety of biological material and reagents to broaden the range of applications for the instant emulsion technology. Polyacrylamide beads (FIG. 17, Panel A) were conjugated with oligonucleotides, which were used as primers during PCR. Such targeted analysis with instant emulsion technology by functionalizing the template particle with DNA enables a wide range of applications such as targeted (towards a specific cell type) scRNA-seq from a heterogeneous population of cells. While the present example utilized beads functionalized with oligos, other functionalizations, e.g., with antibodies or binding fragments thereof, may be readily envisioned by one of ordinary skill in the art. Beads were soaked in PCR reagent. Excess aqueous solution was removed. Agarose, Triton and cells were added, followed by oil. PTE was performed as described herein. The oil was transferred and thermocycling was performed. ddPCR in polyacrylamide core beads with agarose shell was performed at two dilution factors (FIG. 17, Panel B). The fraction with fluorescence positive droplets correspond with template concentration. The image of polyacrylamide core beads with agarose shell showed polyacrylamide core beads surrounded by agarose shell after droplets were broken and washed. As shown in FIG. 17, Panel C, depicting images of the droplets after FACS, fluorescence positive droplets were sorted, collected, and observed under a microscope. The sorted beads were fluorescent and were surrounded by agarose shell after FACS. qPCR was performed to examine the genome recovery in the agarose shell (FIG. 17, Panel D). Four primer sets in different loci were used. Signals were observed after 35 cycles and genomic DNA was encapsulated in the agarose shell.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. Costa, L. da F.; Rodrigues, F. A.; Cristino, A. S. Complex networks: The key to systems biology. *Genet. Mol. Biol.* 2008, 31, 591-601.
2. Blainey, P. C.; Quake, S. R. Dissecting genomic diversity, one cell at a time. *Nat. Methods* 2014, 11, 19-21.
3. Civelek, M.; Lusis, A. J. Systems genetics approaches to understand complex traits. *Nat. Rev. Genet.* 2014, 15, 34-48.
4. Weaver, W. M. et al. Advances in high-throughput single-cell microtechnologies. *Curr. Opin. Biotechnol.* 2014, 25, 114-123.
5. Fritzsch, F. S. O.; Dusny, C.; Frick, O.; Schmid, A. Single-Cell Analysis in Biotechnology, Systems Biology, and Biocatalysis. *Annu. Rev. Chem. Biomol. Eng.* 2012, 3, 129-155.
6. Soon, W. W.; Hariharan, M.; Snyder, M. P. High-throughput sequencing for biology and medicine. *Mol. Syst. Biol.* 2013, 9, 640.
7. Macosko, E. Z. et al. Highly parallel genome-wide expression profiling of individual cells using nanoliter droplets. *Cell* 2015, 161, 1202-1214.
8. Mazutis, L. et al. Single-cell analysis and sorting using droplet-based microfluidics. *Nat. Protoc.* 2013, 8, 870-891.
9. Kimmerling, R. J. et al. A microfluidic platform enabling single-cell RNA-seq of multigenerational lineages. *Nature Commun.* 2016, 7, 10220.
10. Kim, J. H. et al. Droplet Microfluidics for Producing Functional Microparticles. *Langmuir* 2014, 30, 1473-1488.
11. Guo, M. T.; Rotem, A.; Heyman, J. A.; Weitz, D. A. Droplet microfluidics for high-throughput biological assays. *Lab Chip* 2012, 12, 2146-2155.
12. Joanicot, M.; Ajdari, A. Droplet control for microfluidics. *Science* 2005, 309, 887-888.
13. Tran, T. M.; Lan, F.; Thompson, C. S.; Abate, A. R. From tubes to drops: droplet-based microfluidics for ultrahigh-throughput biology. *J. Phys. D. Appl. Phys.* 2013, 46, 114004.
14. Abate, A. R. et al. DNA sequence analysis with droplet-based microfluidics. *Lab Chip* 2013, 13, 4864-4869.
15. Autour, A.; Ryckelynck, M. Ultrahigh-throughput improvement and discovery of enzymes using droplet-based microfluidic screening. *Micromachines* 2017, 8, 128.
16. Mashaghi, S.; Abbaspourrad, A.; Weitz, D. A.; van Oijen, A. M. Droplet microfluidics: A tool for biology, chemistry and nanotechnology. *TrAC—Trends Anal. Chem.* 2016, 82, 118-125.
17. Abbaspourrad, A. et al. Label-free single-cell protein quantification using a drop-based mix-and-read system. *Sci. Rep.* 2015, 5, 12756.
18. Baker, M. Digital PCR hits its stride. *Nat. Methods* 2012, 9, 541-544.
19. Kolodziejczyk, A. A.; Kim, J. K.; Svensson, V.; Marioni, J. C.; Teichmann, S. A. The Technology and Biology of Single-Cell RNA Sequencing. *Mol. Cell* 2015, 58, 610-620.
20. Zilionis, R. et al. Single-cell barcoding and sequencing using droplet microfluidics. *Nat. Protoc.* 2017, 12, 44-73.
21. Spencer, S. J. et al. Massively parallel sequencing of single cells by epicPCR links functional genes with phylogenetic markers. *ISME J.* 2016, 10, 427-436.
22. Tamminen, M. V.; Virta, M. P. J. Single gene-based distinction of individual microbial genomes from a mixed population of microbial cells. *Front. Microbiol.* 2015, 6, 195.
23. Katepalli, H.; Bose, A. Response of Surfactant Stabilized Oil-in-Water Emulsions to the Addition of Particles in an Aqueous Suspension. *Langmuir* 2014, 30, 12736-12742.
24. Abate, A. R.; Chen, C.-H.; Agresti, J. J.; Weitz, D. A. Beating Poisson encapsulation statistics using close-packed ordering. *Lab Chip* 2009, 9, 2628-2631.
25. Yan, K. S. et al. Intestinal Enteroendocrine Lineage Cells Possess Homeostatic and Injury-Inducible Stem Cell Activity. *Cell Stem Cell* 2017, 21, 78-90.e6.
26. Spies, N. et al. Genome-wide reconstruction of complex structural variants using read clouds. *Nat. Methods* 2017, 14, 915-920.
27. Hindson, B. J. et al. High-throughput droplet digital PCR system for absolute quantitation of DNA copy number. *Anal. Chem.* 2011, 83, 8604-8610.
28. Pinheiro, L. B. et al. Evaluation of a droplet digital polymerase chain reaction format for DNA copy number quantification. *Anal. Chem.* 2012, 84, 1003-1011.
29. Taly, V. et al. Multiplex picodroplet digital PCR to detect KRAS mutations in circulating DNA from the plasma of colorectal cancer patients. *Clin. Chem.* 2013, 59, 1722-1731.
30. Elnifro, E. M.; Ashshi, A. M.; Cooper, R. J.; Klapper, P. E. Multiplex PCR: Optimization and Application in Diagnostic Virology. *Clin. Microbiol. Rev.* 2000, 13, 559-570.
31. Lance, S. T.; Sukovich, D. J.; Stedman, K. M.; Abate, A. R. Peering below the diffraction limit: robust and specific sorting of viruses with flow cytometry. *Virol J* 2016, 13, 201.
32. Collins, D. J.; Neild, A.; deMello, A.; Liu, A-Q.; Ai, Y. The Poisson distribution and beyond: methods for microfluidic droplet production and single cell encapsulation. *Lab Chip* 2015, 15, 3439-3459.

33. Halldorsson, S.; Lucumi, E.; Gomez-Sjoberg, R.; Fleming, R. M. T. Advantagesand challenges of microfluidic cell culture in polydimethylsiloxane devices. *Biosens. Bioelectron.* 2015, 63, 218-231.

34. Bjork, S. M.; Sjostrom, S. L.; Andersson-Svahn, H.; Joensson, H. N. Metabolite profiling of microfluidic cell culture conditions for droplet based screening. *Biomicrofluidics* 2015, 9, 044128.

35. Brouzes, E. et al. Droplet microfluidic technology for single-cell high-throughput screening. *Proc. Natl. Acad. Sci. U.S.A* 2009, 106, 14195-14200.

36. Zhu, Z.; Yang, C. J. Hydrogel Droplet Microfluidics for High-Throughput Single Molecule/Cell Analysis. *Acc. Chem. Res.* 2017, 50, 22-31.

37. Shembekar, N.; Chaipan, C.; Utharala, R.; Merten, C. A. Droplet-based microfluidics in drug discovery, transcriptomics and high-throughput molecular genetics. *Lab Chip* 2016, 16, 1314-1331.

38. Gielen, F. et al. Ultrahigh-throughput-directed enzyme evolution by absorbance-activated droplet sorting (AADS). *Proc. Natl. Acad. Sci. U.S.A* 2016, 113, E7383-E7389.

39. Romero, P. A.; Tran, T. M.; Abate, A. R. Dissecting enzyme function with microfluidic-based deep mutational scanning. *Proc. Natl. Acad. Sci. U.S.A* 2015, 112, 7159-7164.

40. Sukovich, D. J.; Lance, S. T.; Abate, A. R. Sequence specific sorting of DNA molecules with FACS using 3dPCR. *Sci. Rep.* 2017, 7, 39385.

41. Lim, S. W.; Abate, A. R. Ultrahigh-throughput sorting of microfluidic drops with flow cytometry. *Lab Chip* 2013, 13, 4563-4572.

42. Griffiths, A. D.; Tawfik, D. S. Miniaturising the laboratory in emulsion droplets. *Trends Biotechnol.* 2006, 24, 395-402.

43. Sandberg, J.; Stahl, P. L.; Ahmadian, A.; Bjursell, M. K.; Lundeberg, J. Flow cytometry for enrichment and titration in massively parallel DNA sequencing. *Nucleic Acids Res.* 2009, 37, e63.

and water that is in contact with and surrounds each target particle and each monodisperse template particle, wherein 99% or more of the plurality of monodisperse template particles vary in diameter by less than a factor of 10, wherein the monodisperse template particles comprise polyethylene glycol (PEG) or agarose;

(iii) combining the first mixture with a second fluid in the absence of a microfluidic channel to provide a second mixture, wherein the second fluid is immiscible with the first fluid; and (iv) shearing the second mixture by vortexing in the absence of a microfluidic channel such that a plurality of the monodisperse template particles are encapsulated in a plurality of monodisperse droplets ranging from 0.1 to 1000 microns in diameter in the second fluid, thereby providing a plurality of monodisperse droplets comprising one of the monodisperse template particles, one of the plurality of target particles, and water that is in contact with and surrounds both the one monodisperse template particle and the one target particle, wherein each monodisperse droplet further comprises a surfactant membrane comprising the surfactant, wherein the surfactant membrane is in contact with both the water inside the monodisperse droplet and the second fluid outside the droplet, wherein the surfactant membrane is in contact with and surrounds the water that is in contact with and surrounds both the one monodisperse template particle and the one target particle, wherein the plurality of monodisperse droplets have a variation in diameter of less than a factor of 10, wherein the one target particle is not immobilized on the one monodisperse template particle, wherein the second fluid is 2-(trifluoromethyl)-3-ethoxydodecafluorohexane fluorinated oil.

2. The method of claim 1, wherein combining the plurality of monodisperse template particles with the first fluid to

```
                              SEQUENCE LISTING


<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1

atcgatcgat cgatcgatcg                                                   20
```

provide the first mixture comprises causing a portion of the first fluid to be absorbed by the monodisperse template particles.

What is claimed is:

1. A method for generating an emulsion, the method comprising:

(i) providing a first fluid comprising a plurality of target particles, water that surrounds each target particle, and a surfactant selected from the group consisting of octylphenol ethoxylate and octylphenoxypolyethoxyethanol (IGEPAL);

(ii) combining a plurality of monodisperse template particles with the first fluid to provide a first mixture comprising the plurality of target particles, the surfactant, the plurality of monodisperse template particles,

3. The method of claim 1, comprising removing excess first fluid from the first mixture after causing the portion of the first fluid to be absorbed by the monodisperse template particles.

4. The method of claim 1, wherein combining the plurality of monodisperse template particles with the first fluid to provide the first mixture comprises flowing a portion of the first fluid into the monodisperse template particles.

5. The method of claim 1, further comprising removing one or more droplets that do not comprise one of the monodisperse template particles by filtration or centrifugation.

6. The method of claim 5, wherein the monodisperse droplets have an average diameter and the one or more droplets that do not comprise one of the monodisperse template particles have an average diameter which is smaller than the average diameter of the monodisperse template particles.

7. The method of claim 1, wherein the target particles are one or more of DNA molecules, RNA molecules, or cells.

8. The method of claim 7, wherein the target particles are cells, and wherein a majority of the monodisperse droplets do not comprise more than one cell per droplet.

9. The method of claim 7, wherein the target particles are cells, further comprising incorporating a cell lysis reagent into the monodisperse droplets, wherein the cell lysis reagent is present in the first mixture prior to encapsulation of the plurality of the monodisperse template particles in the plurality of monodisperse droplets.

10. The method of claim 1, further comprising sorting the monodisperse droplets.

11. The method of claim 10, wherein the sorting comprises one or more steps selected from the group consisting of dielectrophoretic deflection, selective coalescence, fluorescence activated cell sorting (FACS), electrophoresis, acoustic separation, magnetic activated cell sorting (MACS), flow control, or other stimulus used to selectively deflect monodisperse droplets.

12. The method of claim 1, wherein the target particles are nucleic acids, wherein the first fluid further comprises nucleic acid synthesis reagents, wherein the monodisperse droplets further comprise the nucleic acid synthesis reagents, and wherein the method further comprising subjecting one or more of the monodisperse droplets to nucleic acid synthesis conditions.

13. The method of claim 12, further comprising sequencing nucleic acids and/or nucleic acid synthesis and/or amplification products from one or more of the plurality of monodisperse droplets.

14. The method of claim 13, further comprising detecting one or more of the target molecules, a portion thereof, a nucleic acid synthesis product thereof, and/or a nucleic acid amplification product thereof by detecting one or more of detection reagents encapsulated in the monodisperse droplets.

15. The method of claim 1, wherein the monodisperse template particles are a first type of particle, and wherein the method further comprises encapsulating one or more of a second type of particle in a droplet with one or more of the first type of particle.

16. The method of claim 1, wherein the surfactant is octylphenoxypolyethoxyethanol (IGEPAL).

* * * * *